US009643152B2

(12) United States Patent
Cronin

(10) Patent No.: US 9,643,152 B2
(45) Date of Patent: May 9, 2017

(54) METHODS FOR THE PREPARATION OF REACTION VESSELS

(71) Applicant: The University Court of the University of Glasgow, Glasgow (GB)

(72) Inventor: Leroy Cronin, Glasgow (GB)

(73) Assignee: The University Court of the University of Glasgow (GB)

( * ) Notice: Subject to any disclaimer, the term of this patent is extended or adjusted under 35 U.S.C. 154(b) by 291 days.

(21) Appl. No.: 14/379,105

(22) PCT Filed: Feb. 18, 2013

(86) PCT No.: PCT/GB2013/050389
§ 371 (c)(1),
(2) Date: Aug. 15, 2014

(87) PCT Pub. No.: WO2013/121230
PCT Pub. Date: Aug. 22, 2013

(65) Prior Publication Data
US 2015/0010461 A1 Jan. 8, 2015

(30) Foreign Application Priority Data
Feb. 17, 2012 (GB) .................................. 1202737.1

(51) Int. Cl.
*A61Q 15/00* (2006.01)
*B01J 19/02* (2006.01)
*B01L 3/00* (2006.01)
*B29C 67/00* (2017.01)
*B01J 19/00* (2006.01)
*C01G 51/00* (2006.01)
*C07D 471/04* (2006.01)
*C07F 19/00* (2006.01)
*B29K 23/00* (2006.01)
*B29K 105/00* (2006.01)
*B29L 31/00* (2006.01)

(52) U.S. Cl.
CPC .......... *B01J 19/02* (2013.01); *B01J 19/0053* (2013.01); *B01L 3/52* (2013.01); *B29C 67/0051* (2013.01); *B29C 67/0059* (2013.01); *C01G 51/006* (2013.01); *C07D 471/04* (2013.01); *C07F 19/005* (2013.01); *B01L 2200/12* (2013.01); *B01L 2200/16* (2013.01); *B29K 2023/12* (2013.01); *B29K 2105/0014* (2013.01); *B29K 2995/0058* (2013.01); *B29L 2031/712* (2013.01)

(58) Field of Classification Search
CPC .............................. C01G 25/006; A61Q 15/00
USPC .......................................................... 423/463
See application file for complete search history.

(56) References Cited

U.S. PATENT DOCUMENTS

| 2005/0058573 A1 | 3/2005 | Frost, III |
| 2007/0012891 A1 | 1/2007 | Maltezos et al. |
| 2010/0044320 A1 | 2/2010 | Weber et al. |

FOREIGN PATENT DOCUMENTS

| DE | 20206371 U1 | 6/2002 |
| EP | 2404672 A1 | 1/2012 |
| WO | 2005040348 A2 | 5/2005 |
| WO | 2009013751 A2 | 1/2009 |
| WO | 2009042671 A1 | 4/2009 |
| WO | 2011094572 A2 | 8/2011 |

OTHER PUBLICATIONS

Kaigala et al., "Rapid Prototyping of Microfluidic Devices with a Wax Printer" Lab Chip, The Royal Society of Chemistry, vol. 7, 2007, pp. 384-387.
GB Search Report for GB1202737.1 dated Jun. 15, 2012.
International Search Report for PCT/GB2013/050389, dates Jun. 5, 2013.
Ahn et al.., "Omnidirectional Printing of Flexile, Stretchable, and Spanning Silver Microelectrodes" Science, vol. 323, 2009, pp. 1590-1593.
Browne, et al. "Self-Division of Macroscopic Droplets: Partitioning of Nanosized Cargo into Nanoscale Micelles" Angew Chem Int. Ed., vol. 49, 2010, pp. 6756-6759.
Cohen, et al., "Direct Freeform Fabrication of Seeded Hydrogels in Arbitrary Geometries" Tissue Engineering, vol. 12, No. 5, 2006, pp. 1325-1335.
Cook, et al., "Solar Energy Supply and Storage for the Legacy and Nonlegacy Worlds", Chem. Rev., vol. 110, 2010, pp. 6474-6502.
Cooper et al., "Modular Redox-Active Inorganic Chemical Cells: iCHELLs" Inorganic Chemical Cells, Angew. Chem. Int. Ed., vol. 50, 2011, pp. 10373-10376.
Farrugia "WinGX Suite for Small-Molecule Single-Crystal Crystallography", Journal of Applied Crystallography, vol. 32, 1999, pp. 837-838.

(Continued)

*Primary Examiner* — Edward Johnson
(74) *Attorney, Agent, or Firm* — Tarolli, Sundheim, Covell & Tummino LLP

(57) ABSTRACT

Provided are methods for preparing and using reaction vessels obtained or obtainable by 3D-printing methods, including a method for preparing a product compound, the method comprising the steps of: (i) providing a reaction vessel that is obtained by a 3-D printing method, wherein the reaction vessel has a reaction space; (ii) providing one or more reagents, optionally together with a catalyst or a solvent, for use in the synthesis of the product compound; and (iii) permitting the one or more reagents to react in the reaction space, optionally in the presence of the catalyst and the solvent, in the reaction vessel, thereby to form the product compound.

19 Claims, 13 Drawing Sheets

(56) References Cited

OTHER PUBLICATIONS

Geissler et al., "Paterning: Principles and Some New Developments" Adv. Mater. vol. 16, 2004, pp. 1249-1269.

Gershenfeld et al., "Intelligent Infrastructure for Energy Efficiency" Science, vol. 327, 2010, pp. 1086-1088.

Gratson et al., "Direct Writing of Three-Dimensional Webs" Nature, vol. 428, 2004, p. 386.

Hanson et al., "3D Microperiodic Hydrogel Scaffolds for Robust Neuronal Cultures" Adv. Funct. Mater., vol. 21, 2011, pp. 47-54.

Ilievski et al., "Soft Robotics for Chemists" Angew Chem. Int. Ed., vol. 50, 2011—pp. 1890-1895.

Kaigala et al., "Rapid Prototyping of Microfluidic Devices with a Wax Printer", Lab Chip, vol. 7, 2007, pp. 384-384.

Kortz et al., "A Large, Novel Polyoxotungstate: [As6IIIW65O217(H2O)7]26" Angew. Chem. Int. Ed. vol. 40, No. 18, 2001, pp. 3384-3386.

Lee et al., "Enhanced Cell Ingrowth and Proliferation through Three-Dimensional Nanocomposite Scaffolds with Controlled Pore Structures" Biomacromolecules, vol. 11, 2010, pp. 682-689.

Lewis "Direct Ink Writing of 3D Functional Materials" Adv. Funct. Mater., vol. 16, 2006, 2193-2204.

Maldonado et al., "Predictiver Modeling in Homogeneous Catalysis: a Tutorial", Chem. Soc. Rev., vol. 39, 2010, pp. 1891-1902.

Malone et al., "Freeform Fabrication of Zinc-Air Batteries and Electromechanical Assemblies" Rapid Prototyping Journal, vol. 10, No. 1, 2004, pp. 58-69.

Malone et al., "Fab@Home: The Personal Desktop Fabricator Kit" Rapid Prototyping Journal, vol. 13, No. 4, 2007, pp. 245-255.

Marks "Flying on Printed Wings" NewScientist, vol. 17, 2011, pp. 17-20.

Martinez et al. "Three-Dimensional Microfluidic Devices Fabricated in Layered Paper and Tape" PNAS. vol. 105, No. 50, 2008, pp. 19606-19611.

Nakamura et al., "Biomatrices and Biomaterials for future Developments of Bioprinting and Biofabrication" IOP Publishing, vol. 2, 2010, pp. 1-6.

Parenty et al., "General One-Pot, Three-Step Methodology Leading to an Extended Class on N-Heterycyclic Cations: Spontaneous Nucleophilic Addition, Cyclization, and Hydride Loss" J. Org. Chem., vol. 69, 2004, pp. 5934-5946.

Pearce et al., "3-D Printing of Open Source Appropriate Technologies for Self-Directed Sustainable Development, Journal of Sustainable Development", vol. 3, No. 4, 2010, pp. 17-29.

Richmond et al., "Fine Tuning Reactivity: Synthesis and Isolation of 1,2,312b-Tetrahydroimidazo[1,2-f]phenanthridines" J.Org. Chem., vol. 74, 2009, pp. 8196-8202.

Sheldrick "Phase Annealing in Shelx-90: Direct Methods for Larger Structures" Acta. Cryst., vol. A46, 1990, pp. 467-473.

Sheldrick "A Short History of Shelx" Acta Cryst., vol. A64, 2008, pp. 112-122.

Stampfi et al., "New Materials for Rapid Prototyping Applications", Macromol. Chem. Phys., vol 206, 2005, pp. 1253-1256.

Stoddart et al., "Chemical Synthesis gets a Fillip from Molecular Recognition and Self-Assembly Process" PNAS, vol. 99, No. 8, 2002, pp. 4797-4800.

Tanaka et al., "Voltammetric and Spectroelectrochemical Studies of 12-Molybdophosphoric Acid in Aqueous and Water-Dioxane at a Gold-Minigrid Optically Transparent Thin-Layer Electrode", Inorg. Chem., vol. 21, 1982, pp. 1662-1666.

Therriault et al., "Chaotic Mixing in Three-Dimensional Microvascular Networks Fabricated by Direct-White Assembly" Nature Materials vol. 2, 2003, pp. 265-271.

Vilbrandt et al., "Fabricating Nature" C. Technoetic. Arts., vol. 7, 2009, pp. 165-174.

Yager et al., "Microfluidic Diagnostic Technologies for Global Public Health" Nature, vol. 442, 2006, pp. 412-418.

Rhino3D, NURBS Modeling for Windows, http://www.rhino3d.com.

METHODS FOR THE PREPARATION OF REACTION VESSELS

CROSS-REFERENCE TO RELATED APPLICATIONS

This application is the U.S. national phase entry of PCT/GB2013/050389, with an international filing data of Feb. 18, 2013, which claims priority to and the benefit of GB 1202737.1 filed on 17 Feb. 2012, the contents of which are hereby incorporated by reference in their entirety.

FIELD OF THE INVENTION

The present invention relates to methods for the preparation of reaction vessels for use in chemical, including biological, synthesis. The invention also provides the reaction vessels obtainable or obtained by such methods, and their use in chemical, including biological, synthesis. Also provided is apparatus for preparing a reaction vessel.

BACKGROUND TO THE INVENTION

Chemical and biological discovery and chemical optimisation projects typically require an extensive and expensive range of laboratory infrastructure. The technology that is required to identify a new lead compound or to optimise a synthesis may make such projects unfeasible for small laboratories and small commercial enterprises. For chemists and biologists working in locations outwith the developed world, and far from large commercial suppliers of laboratory infrastructure, the development of new and optimised chemical and biological methodologies may be hampered by the lack of readily available reactionware, or a lack of choice in such reactionware. In these scenarios it is desirable to have access to technologies that are sustainable, decentralised (i.e. not reliant on close proximity to commercial operations in developed countries) and readily available.

Recent developments in chemical and biological reaction planning and reactionware have included work on, for example, microfluidic technologies and solid-phase reagents. However, these technologies do not necessarily lend themselves well to smaller laboratory environments, as the laboratory apparatus underpinning such work may be complex and may not be easily useable by those with access to a limited range of analytical and preparative tools.

The present inventor has looked to provide a system for the easy and ready preparation of reactionware, which system is easily and readily adapted as required. The present inventor has sought to provide a system that allows a user to bring chemical engineering to a standard laboratory work bench.

SUMMARY OF THE INVENTION

In a general aspect the present invention provides a method for the preparation of a reaction vessel using 3-D printing techniques. Also provided is a vessel obtained or obtainable by the method.

3-D printing techniques are highly versatile, adaptable and relatively simple, and are well suited to the preparation of reaction vessels. By virtue of the design and printing processes, the resultant reaction vessels are highly adapted for the intended chemical, including biological, reaction to be conducted within. The printing techniques offer a user the potential to create bespoke and elaborate reactionware quickly and with little effort. In addition, the present invention may include computer-aided design of the reaction vessel, and in particular computer-automated reactionware design (CARD).

Furthermore, the reaction vessels of the present invention may be used as an active input that is capable of influencing a reaction outcome, such as a reaction yield or the identity of a reaction product. Indeed, the reaction vessels of the invention may facilitate, select or promote one reaction pathway over, possible pathways.

Thus, the reaction vessel architecture may be designed to influence the reaction outcome. Additionally or alternatively, the reaction vessel walls may be provided with a reagent or catalyst for interaction with species held within the vessel. Such reagents and catalysts may therefore provide a direct input to a chemical synthesis or an analysis.

In one aspect there is provided the use of a 3-D printed object as a reaction vessel for a chemical reaction. The chemical reaction may be a biological reaction.

In a further aspect there is provided a method for preparing a product compound, the method comprising the steps of:

(i) providing a reaction vessel that is obtained or obtainable by a 3-D printing method, wherein the reaction vessel has a reaction space;

(ii) providing one or more reagents, optionally together with a catalyst or a solvent, for use in the synthesis of the product compound; and (iii) permitting the one or more reagents to react in the reaction space, optionally in the presence of the catalyst and the solvent, in the reaction vessel, thereby to form the product compound.

In one embodiment, the reaction vessel is obtained by a 3-D printing method. Thus, the step of printing the reaction vessel constitutes a step in the method for preparing a product compound.

In a further aspect there is provided a method for analysing the outcome of a reaction, the method comprising the steps of:

(i) performing a reaction in the reaction space of a first reaction vessel, and determining a reaction outcome;

(ii) preparing a second reaction vessel using a 3-D printing method, wherein the second reaction vessel differs from the first reaction vessel;

(iii) performing a reaction in the reaction space of the second reaction vessel, and determining a reaction outcome;

(iv) comparing the reaction outcomes from step (i) and step (ii).

In one aspect there is provided a method for preparing a reaction vessel, the method comprising the steps of;

(i) providing a programmable 3-D printer, wherein a printing head of the 3-D printer is provided with a material for printing;

(ii) printing a vessel according to a printing schedule, thereby to obtain a reaction vessel.

Also provided is a method for preparing a reaction vessel, the method comprising the steps of:

(i) providing a programmable 3-D printer, wherein a printing head of the 3-printer is provided with a material for printing;

(ii) printing a vessel according to a printing schedule, thereby to obtain a reaction vessel; and (iii) providing the vessel with a reagent, a catalyst or a solvent for use in a reaction, wherein the a reagent, a catalyst or a solvent is printed onto or into the reaction vessel by the 3-D printer.

In another aspect of the invention there is provided the use of a reaction vessel as a reagent or a catalyst in a reaction, wherein the reaction vessel is obtained by a 3-D printing method, and the reaction vessel has a reagent or catalyst contained within a wall of the vessel and exposed to a reaction space of the vessel.

In another aspect, there is provided a reaction vessel obtained or obtainable by the methods described herein.

The present invention also provides a computer suitably programmed to prepare a vessel as described herein, for example using as a method as described herein. The computer may be connected to a printer capable of 3-D printing.

Also provided is a memory device, such as a disk, holding a programme that is suitable for the preparation of a vessel as described herein.

In alternative aspects of the invention there are provided methods suitable for the preparation of formulations in a reaction vessel of the invention.

DESCRIPTION OF THE FIGURES

FIG. 1 (B) is a close-up photograph of the fabricator printing a vessel of the invention;

FIG. 1 (C) is a schematic of a vessel according to one embodiment of the invention.

FIG. 4 also includes a partial $^1H$ NMR spectrum (400 MHz, $d_6$-DMSO, 298 K) of the product heterocycle 3. The product crystal structure is represented in ball and stick mode.

FIG. 5(D) is a cyclic voltamagram recorded using the reactionware shown in FIG. 5(A)-(C) for the electrochemical cycling of an acidic PMA solution (5 mM in 0.1M $H_2SO_4$) at a scan rate of 0.1 $Vs^{-1}$. FIG. 5 (E) is a partial UV-visible spectrum taken during the electrochemical cycling of the PMA solution (dashed line=before reduction, solid line=after partial reduction). Relative absorbances are normalised at 500 nm. The active surface area of the ITO working electrode was 2.0 $cm^2$.

FIG. 12 (A) is the reaction vessel from above, showing the two conductive carbon-black-based electrodes. The working electrode (upper line) had an area of approximately 0.8×0.1 $cm^2$ and the reference/counter electrode rail (lower line) had an area of 1.0×0.2 $cm^2$. FIG. 12 (B) is the connected cell filled with 1 mL 5 mM PMA in 0.1M $H_2SO_4$ before electrochemical reduction; FIG. 12 (C) is the same cell after reduction at −2.5 V for 4500 seconds. FIG. 12 (D) shows the relationship between charge passed and time for the reduction process, showing the current to be constant over the time course of the experiment.

DETAILED DESCRIPTION OF THE INVENTION

Figure 1:
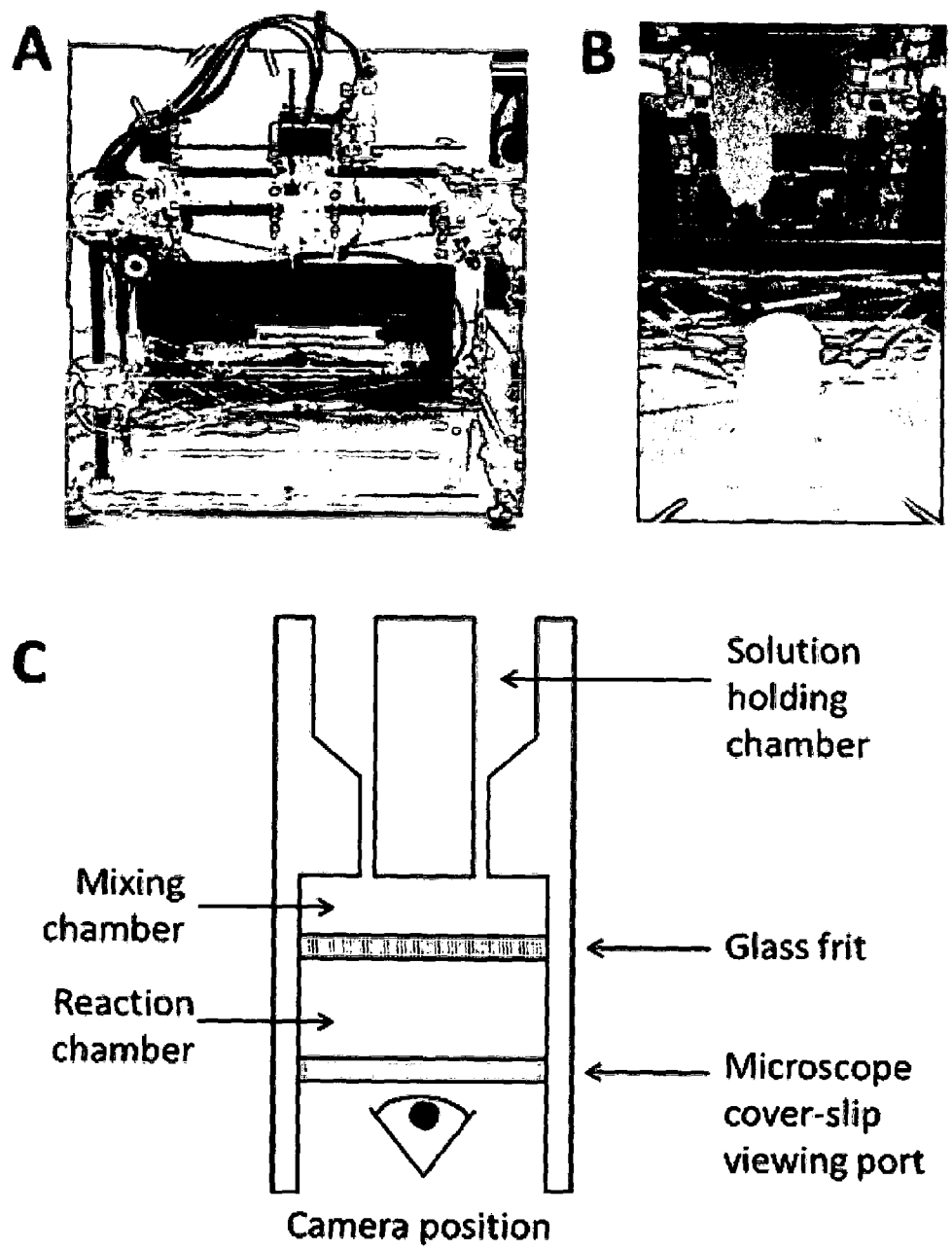
FIG. 1 (A) is a photograph of the Fab@Home Version 0.24 RC6 freeform fabricator.

The present inventor has established that 3-D printing technologies may be used to prepare vessels that are suitable for holding a wide range of components, such as chemical and biological reagents, and which is capable of acting as a reaction vessel for those components. Such vessels may also incorporate, or may interact with, analytical apparatus, such as spectrometers, and may incorporate or may interact with service devices i.e. devices that are capable of providing inputs such as heat, light, and electrons to a reaction mixture contained in the vessel. Examples of such service devices include heating elements and electrodes. The service devices may also be adapted to remove outputs, which may be heat and electrons from a reaction mixture. As such, the reaction vessels of the invention are suitable for use in a wide range of chemical and chemical engineering projects.

In some embodiments, the reaction vessel provides an input to a reaction, either through the influence of the reaction vessel architecture (shape) or through reagents or catalysts that are suitably provided at the surfaces of the reaction vessel walls. Such reaction vessels may be regarded as having an active role in the reaction, rather than the traditional passive role of the reaction vessel. Thus, the reaction vessel may be regarded as having been inserted into the reaction.

The vessels of the invention may be prepared rapidly, repeatedly, accurately and cheaply, and they may be readily modified as required. The method is well suited for automation, and automation may be used to extend the present methods of preparation to the evolvable generation of new reaction vessels, which new vessels may alter the reaction outcome of a reaction. Analysis of reaction outcomes may be used to screen reaction vessel architectures for an optimal vessel configuration.

Thus, the methods of the present invention allow the preparation of vessels having an advantageous influence on a reaction outcome. In this way, the vessels and the methods of the present invention may be used to advantage in a chemical engineering setting and uniquely combine both the chemical engineering, chemical design and allow the exploitation of emergent effects hitherto not exploitable in a reliable way.

The present inventor has developed production methods for the evolvable synthesis of bespoke reaction vessels, which are reusable and optionally may also be self-healing. The preparation of such reactionware would be extremely difficult to realise without the aid of so-called robocasting techniques. Digital technology may be used to design and manufacture the reaction vessel and advantageously such technology may also be used to prepare reaction mixtures, initiate reactions, monitor reactions in situ, and collect and purify products. The methods of the present invention, along with the apparatus of the present invention, provide an attractive alternative to traditional, passive-vessel approaches to chemical reaction planning.

Until now the design of new chemical methodologies has paid little attention to the reactor design. The present inventor has demonstrated that reaction vessels may be prepared that link the reactor design to the reaction process takes. Examples include the production of active reactors (reactionware) that have reagents, sensors and actuators embedded within the vessel walls. Furthermore the alteration of reaction vessel topologies may be used to alter reaction outcomes, especially if the vessel walls have an active surface that can change in response to pH, ionic strength, ligand binding, and impurity development, and so on.

The utility of the vessels and the methods of the invention is demonstrated by the present inventor through a series of chemical syntheses and analyses. Indeed, the present inventor has shown that the vessels and the methods of the invention may be used in discovery chemistry to synthesise new chemical entities.

Using the methods of the invention it is possible to create a reaction vessel that is capable of controlling reagent mixing sequences, reagent flow rates and methods of purification. The features that allow such control may be built into the reactor vessel design, combining the disciplines of synthetic chemistry, molecular modeling, and chemical engineering in a low-cost, reconfigurable and highly accessible format. The vessel and methods described herein may be deployed safely in laboratory and non-laboratory environments, thereby providing a chemical discovery platform that makes techniques from chemical engineering accessible to standard synthetic laboratories, and even individuals.

The present invention integrates design software and printing hardware to control chemical outcomes. Thus, chemistry that is relevant to molecular nanotechnology, catalyst optimization, natural chemical processes, and drug design can be explored using the present invention.

3-D printing techniques have previously been used in the multistage syntheses of microfluidic devices. For example, Therriault et al. describe the use of 3-D printing and casting techniques to form microvascular networks. Here, however, the 3-D printing technique is only the initial stage of a more elaborate synthesis of a fluidic device. The printing step is used to prepare a scaffold to which a layer of material is added to form fluidic channels. The channels are then filled with a photocurable resin. Photolithography is used to cure specific portions of the resin, thereby to block the channels in these regions. Uncured resin is drained from the structure to provide open channels. Thus, the printing sequence does not directly provide a vessel through which active components may be passed. It is also a complex preparation, not well suited to a small laboratory.

Moreover, Therriault et al. do not suggest that the structure described could or should be used as a reaction vessel. Rather, the authors look at fluid flow in the microfluidic channels, and in particular the degree to which two (mutually unreactive) components may be chaotically mixed in the 3-D channels.

3-D printing techniques have also been used to prepare batteries and electrochemical assemblies, including the work of, for example, Malone et al. (*Rapid Prototyping Journal* 2004, 10, 58). Such products are not reaction vessels, for they do not permit material to be added and removed from a reaction space contained within.

3-D Printing

The use of 3-D printing technologies by small laboratories and individuals promises to bypass sophisticated manufacturing centres and revolutionise every part of the way that materials are turned into functional devices, from design through to operation. However, apart from the utilisation of 3-D printing for tissue-growth scaffolds and large-scale industrial prototyping, applications of this technology remain limited. Recently, 3D-printing has been used to produce highly specialised electronic and pneumatic devices. 3-D printing techniques have also been used to prepared scaffolds upon which, for example, microfluidic devices may be built (such as described above). However, the potential for using 3-D printed reaction vessels as an accessible and readily-reconfigurable chemical discovery tool has not been addressed.

The inventor foresees that a user may obtain a design for a product from an internet source, either commercial or open source. The user may wish to modify the basic product design for an intended purpose, and then look to rapidly produce any number of items at low cost on a (preferably) portable and robust device. The present inventor has been motivated to develop a new technology that is based on the use of a basic, easily modifiable 3-D printing apparatus for use in methods of preparing products for use in chemical technologies.

Accordingly, the inventor has developed strategies for producing packages combining a 3-D printer, design-software and chemistry. Such packages provide a user with access to chemistry and chemical discovery without the need for expensive laboratory infrastructure. This places traditionally expensive chemical engineering technology within reach of typical laboratories and small commercial enterprises. Moreover, these packages could revolutionise access to healthcare and the chemical sciences in the developing world, allowing diagnosis and treatment preparation to occur in a sustainable, decentralised and timely fashion. As shown herein, the present invention utilises printer hardware of minimal cost together with a comparatively broad range of potential printable materials.

As well as simply providing an alternative reaction ware for the chemist and biologist, the present invention also provides those same chemists and biologists with the design freedom to create reactionware that is tailored to a particular reaction. The design freedom also allows the user to design and prepare parts of a reaction vessel that control or influence the delivery of reagents and solvent into a reaction chamber, or control or influence the formation of product, and its purification and isolation from a reaction mixture.

The present invention is also a simple alternative to traditional methods of reactionware preparation. Glass blowing techniques, for example, are used to construct reactionware comprising flasks linked to reservoirs and the like. The present invention allows the preparation of reaction vessels through a straight forward printing procedure.

Reaction Vessel

The present invention provides a reaction vessel. The reaction vessel is obtained or obtainable by a 3-D printing method as described herein. The reaction vessel may take the form of a conventional flask or it may take the form of a fluidic device, such as a substrate that is suitably adapted for flow chemistries. The vessel may be adapted, as appropriate to interact with services for the delivery of material, such as reagents and solvent, to the vessel, and/or the delivery of material from the vessel.

The reaction vessel may be adapted for collaboration with analytical apparatus suitable for monitoring physical and chemical parameters within the vessel, for example during a reaction. Such embodiments are described in further details below.

In general, the reaction vessel is provided with walls that define a reaction space suitable for containing reagents within. In one embodiment, the reaction space may be suitable for holding the reagents. In this embodiment, the reaction space is capable of holding the reagents without flow of the material out of that space. Here, the reaction space may be referred to as a chamber. In this embodiment the reaction space, or chamber, may be contrasted with a fluid flow channel, which is incapable of holding material. Rather, the material in a flow channel is permitted to move along the channel, for example by gravity or by fluid pressure. Thus material in a flow channel has a negligible residency time.

A reaction space for holding reagents is typically provided with a base attached to a wall (or walls) to provide a suitable chamber for holding material within. The reaction space may have one or more apertures, but these are such that allow material to enter into the chamber and reside there.

In other embodiments, the reaction space is a flow channel, through which reagents may flow and react. A reaction vessel may have both of these reaction spaces. A flow channel is typically elongate with open ends.

In one embodiment the vessel defines a reaction space suitable for holding reagents within. The reaction space is suitable for holding liquids within. The preferred reactions for use with the reaction vessel are those involving a liquid reaction mixture. The liquid may be an aqueous or organic reaction mixture.

The reaction vessel may be provided with an aperture. The aperture may be an opening in the vessel wall to the reaction space. Reagents may be added through the aperture to the reaction space. The aperture may be provided as an opening through which components of the reaction mixture may be removed, for example for collection or analysis. The opening may be present in order to provide access for part of an analytical device to the reaction space. The opening may also be present in order to provide access for services to the reaction space. These services may include the provision of a gas, such as a reaction gas or an inert gas, or light, or cabling for an electrical device provided in the reaction space (such as an analytical device contained within the reaction space or for a device providing an input to the reaction, such as light or electricity.

In one embodiment, the reaction space does not have an opening or a fluid passage through the vessel wall. Here, the reaction space may be sealed from the outer environment. It is possible to add reagents or solvent and the like to the reaction vessel during the reaction vessel preparation. For example, such material may be printed into the reaction vessel in line with the reaction vessel printing steps. The final stages of the reaction vessel preparation may then seal the reaction vessel.

The vessel may also be provided with one or more channels, which are in fluid communication with the reaction space. A channel may serve as a conduit to deliver a reagent to the reaction space. A channel may also serve as a conduit to remove a product or a by-product from the reaction space, for example for collection and analysis. A channel may be used for delivery and/or removal of material from the reaction space.

The channel path is not particularly limited and 1-D (linear), 2-D and/or 3-D channel paths may be provided.

The vessel may also include a reservoir for holding a reagent until it is required. The reagent may be delivered from the reservoir to the reaction vessel via a connecting fluid channel.

In one embodiment, the reaction vessel has a plurality of reaction spaces, such as a plurality of reaction chambers. In one embodiment, the reaction spaces are in fluid communication. The reaction vessel may have two, three, four or more reaction spaces. The reaction spaces may be in series. The reaction chambers may be fluidly connected by channels that open to an aperture in respective reaction spaces.

Where a plurality of reaction spaces is arranged in series, a reaction mixture contained in a first reaction space may be transferable to a second reaction space. The reaction mixture may be permitted to react further in the second reaction space, for example with reagents or catalysts added into or present in the second reaction spaces. Where the reaction vessel is provided with further reaction spaces, such as a third reaction space, the reaction mixture from the second reaction space may be transferred into the third reaction space, for further reaction.

Accordingly, as described herein, one or more reagents are permitted to react in a first reaction space, optionally in the presence of the catalyst and the solvent, in the reaction vessel, thereby to form a first product compound. This first product may be subsequently transferred from the first reaction space to a second reaction space. One or more further reagents, optionally together with a further catalyst and/or further solvent, for use in the synthesis of a second product compound may then be provided and may be permitted to react with the first product in the second reaction space, thereby to form a second product compound.

In one embodiment a reaction space in a plurality of serially linked reaction spaces has an inlet aperture and outlet aperture. The inlet aperture allows for delivery of material (e.g. reagents, catalysts, and more generally a reaction mixture) into the reaction space. The outlet aperture allows material to exit the reaction space, for example to exit the reaction vessel or to transfer to the next reaction space in the series.

In one embodiment, a plurality of reaction spaces arranged in series may have a direct fluid connection between the first reaction space in the series and the last reaction space in the series. Thus, a product may be transferred directly (i.e. not via intermediate reaction spaces) from the last to the first reaction space. In this way a multi-step synthesis may be conducted using a small number of reaction spaces, and it is not necessary that a reaction chamber be provided for each step in a multistep synthesis. Nevertheless, it is preferred that a reaction chamber be provided for each step in a multistep synthesis, as this provided for simpler management of the reaction sequence.

In one embodiment an inlet or outlet may be provided with a filter to prevent certain materials, such as catalysts or insolubles, from passing from one reaction space to another.

The inlet and outlet apertures of a reaction space may be arranged orthogonally. Thus, the outlet and inlets are provided at locations that allow material to be added into the reaction space via the inlet without that material flowing out of the reaction space via the outlet. Similarly, material may be removed from the reaction space via the outlet without the material flowing out of the reaction space via the inlet.

As shown herein, the layout of the reaction spaces within the reaction vessel may be such as to allow material to be transferred from one space to another by simple rotation of the reaction vessel. A rotation of the vessel may provide an outlet at a lower portion of a reaction space. Material within the reaction space will then flow out of the reaction space via that outlet under gravity. Similarly, rotation of the device may provide an inlet at an upper portion of the reaction space, thereby to allow material to be added to the reaction space via that inlet, under gravity. Where a reaction vessel is provided with a plurality of reaction spaces in series, the inlets and outlets of the first and second reaction spaces are arranged such that a rotation of the device permits material in the first reaction space to flow from the first reaction space to the second reaction space, from the outlet of the first reaction space to the inlet of the second reaction space. The rotation does not allow material to flow out of the first reaction space via the inlet of the first reaction space. The rotation does not allow material to further flow out of the second reaction space via the outlet.

In one embodiment, a reaction vessel has a plurality of reaction spaces, such as reaction chambers, that are not in fluid communication. Here a reaction space may be used entirely independently from other reaction spaces present. Thus the reaction vessel may be used to conduct a plurality of reactions in parallel. In one embodiment, each of the reaction chambers may be individually sealed with reagents and solvent therein. In this way, the sealed chambers are suitable for performing parallel solvothermal and hydrothermal reactions, including crystallisations.

In one embodiment, the reaction spaces may be placed in fluid communication by e.g. inserting a needle between a wall of neighbouring reaction vessels, thereby to generate a fluid passage therebetween.

The reaction space may be isolable from the environment. Thus, the reaction vessel walls may provide a barrier that is substantially impermeable to air. Such a vessel is suitable for performing reactions under reduced or increased pressure. The vessel may also be useful for performing reactions where an inert atmosphere is required, for example excluding oxygen and excluding water.

Where there is an aperture in the reaction vessel it may also serve as an exit port for gases evolved during the reaction. The reaction space may be under reduced or increased pressure (with respect to standard atmospheric pressure). The aperture may therefore allow communication with the compressor or pressurizing gas that is provided to change the reaction space pressure. The aperture may also allow communication of the reaction space with an inert gas supply.

The size and the shape of the reaction space are not particularly limited. The shape of the reaction space may be similar to those shapes provided by traditional reaction glassware, such as round-bottomed flasks (a substantially spherical reaction space), a conical flask (a substantially conical or frustoconical reaction space), a vial (a substantially cylindrical reaction space) or a cuvette (a substantially cuboid reaction space), amongst others.

In one embodiment, the volume of the reaction space is at least 0.1 mL, at least 0.5 mL or at least 1.0 mL.

In one embodiment, the volume of the reaction space is at most 10 mL at most 25 at most 50 mL, at most 100 mL, at most 250 mL, at most 500 mL or at most 1,000 mL. In one embodiment, the volume of the reaction space is in a range where the lower and upper limits are selected from the values given above. For example, the volume of the reaction space is in the range 1 to 25 mL.

The walls defining the reaction space may include recesses and protrusions. Such may be provided to perturb the reaction mixture, or to increase the surface area of the vessel walls in the reaction space. In some embodiments the recesses and protrusions may include components for use in the reaction as described below.

The vessel may be provided with heating or cooling fluid channels running through the vessel. These channels are not in communication with the reaction space, or with any reservoirs or channels that are present. The heating or cooling fluid channels may be provided for the passage of heating or cooling fluid through the vessel, thereby to heat or cool the vessel walls which in turn heat or cool the reaction mixture contained within the reaction space.

The vessel may also be placed in a heating or cooling bath in order to heat or cool the contents of the reaction vessel. The thickness of the walls and the choice of wall material may be appropriately selected for the type of cooling method to be employed.

The vessel may itself include components for use in a chemical or biological reaction. During construction the material may be assembled around such components to give the product vessel. Additionally or alternatively, the components may be incorporated into the vessel during pre-programmed pauses in the printing schedule, or may be incorporated into the vessel after the printing is complete.

In one embodiment, the component is a part of an apparatus for supplying a service to the reaction space. The service may be a source of light or heat or cold, or the service may be an electrode for receiving or donating electrons.

Such apparatus may be added to the reaction vessel after the printing procedure in complete. Alternatively, parts of the apparatus may be added during the construction of the reaction vessel in programmed breaks in the printing schedule.

In one embodiment the component is a reagent or a catalyst, and at least a portion of the reagent or catalyst is exposed to the reaction space, such that reagents within the space may interact with the reagent or catalyst. In other embodiment, the reagent or a catalyst is alternatively or additionally exposed to a channel or reservoir.

In some embodiments of the invention, the reaction vessel is provided with a plurality of reaction chambers. One or more, such as two or three, of the reaction chambers may be provided with a component, such as a catalyst or reagent.

In this embodiment, the vessel is itself is capable of providing a direct contribution to the reaction that is performed. Thus the reaction and the reaction vessel are intimately linked. Using the methods of the invention, a reaction vessel may be printed that is a catalyst or a reagent for a reaction. Using the methods described herein, the vessel may be designed for a particular reaction and will influence the reaction outcome. Changes to the quantity and kind of reagent or catalyst may there be used to change a reaction outcome.

The reagent or catalyst may be distributed throughout the material, and therefore throughout the vessel. The distribution of the functional component is such that some of the functional component will be located at the surface of the vessel wall, exposed to the reaction space and/or exposed to a channel.

However, it is preferred that the reagent or catalyst is not distributed through the entire vessel. Instead it is preferred that the functional component is located in at least a portion of the walls of the vessel that define the reaction space. The methods of the invention allow such distribution of materials through the vessel.

The reagent or catalyst is not particularly limited, and the choice of reagent or catalyst will be dictated by the type of reaction to be performed in the reaction space. Of course, the reagent or catalyst selected will be substantially unreactive to the material that holds it. In one embodiment, the component is a catalyst.

In one embodiment, a reaction space of the reaction vessel is provided with a purification zone. The zone may include material for the purification of a reaction mixture. This material may be provided in a reaction space that is located downstream and in fluid communication of the reaction space, where a product material is generated (and such a reaction space may be referred to as a purification zone). Thus, in one embodiment, a reaction vessel is provided with a reaction space having a purification zone. In one embodiment, a reaction vessel is provided with a plurality of reaction spaces, such as reaction chambers. A purification zone may be provided downstream of the last of the reaction spaces, for the purification of the final product mixture. Additionally or alternatively, purification zones may be provided after one or more earlier reaction spaces for purification of intermediate compounds.

The material for purification is not particularly limited and may be a material that is suitable for capturing or interacting with by-product material, such as unreacted reagents, catalyst material or alternative (unwanted) side products. The material may be a solid phase material for capturing the by-products. The material used may be a chromatographic material through which the product and the by-products pass at different rates. For example, the material may be silica, alumina, Celite, carbon and the like.

The purification material, if is provided in a reaction space (and not in a wall of the vessel) may be retained in that reaction space by appropriate placement of filters at the inlets and outlets. Such filters may be simple, and take the form of cotton wool, or may be a membrane of some form, such as paper or a glass frit. Membranes for use in reaction vessels are also described elsewhere in this text, and such may be useful in this embodiment.

The material chosen may be a material for capturing a product from the reaction mixture. Once the remaining reaction mixture is removed, the product may then be released for collection and/or for further reaction within the vessel.

A material for use in purification may be incorporated into a wall of a reaction space, such as described above for a catalysts or reagent. Additionally or alternatively, the material may be packed into a reaction space. Such materials may be provided into the reaction vessel during the vessel preparation procedure, for example during scheduled printing pauses.

In one embodiment, the reaction vessel is relatively homogeneous. Thus, the walls of the vessel are of mostly the same type of material. In some embodiments, as noted above, the vessel walls may include portions that are provide with functionality, such as reagents and catalysts. In some embodiments at least the walls defining the reaction space are provided with a coating. The coating may be provided where the vessel walls are intolerant of a reaction material, such as a reagent catalyst or solvent, that is to be used in the reaction space. The coating may be provided during the preparation of the vessel, for example, the coating may be printed with the vessel walls.

In one embodiment, the vessel comprises a viewing window. The window may be provided at the reaction space. The window may be provided to assist the user, who can monitor reaction progression simply by looking at the contents of the reaction space. The window may also be provided to allow light, including visible and ultraviolet light, to be provided into the reaction space. The window may be provided to allow light to exit from the reaction space. The detection of such light, by eye as noted above, or by suitable detectors may assist the analysis of the reaction mixture, including the identity of products and reaction progress.

In one embodiment, the window may be functionalised, for example as a reaction surface. In one embodiment, the window may have a layer that is a substantially transparent electrode. Thus, the window may assist analysis by providing a view of the reaction space, but it may also be functionalised to participate in the reaction itself.

Where a window is provided, it may be located, when the reaction vessel is in use, above the contents of the reaction space. In an alternative embodiment, the window may form a portion of the wall forming the reaction space.

The window may take the form of a glass slide. Described herein is the use of a standard microscope slide as a window.

In one embodiment, the reaction vessel is provided with a reaction surface. The reaction surface is a surface that is suitably functionalised for use in the reaction performed in the reaction space. The surface is therefore typically provided at the reaction space.

The reaction surface may be contrasted with the functionalised material. This latter feature has functionality dispersed within the material making up at least part of the vessel walls. In contrast the reaction surface is a part of the wall that does not include material. The functionalised surface may have a reagent or catalyst bound to its surface. Such surfaces may be used where it is not practical to include the reagent or catalyst in the material. The surface is not particularly limited, and may include glass or metal surfaces. As with other features of the reaction vessel, the reaction surface may be incorporated into the reaction vessel during the printing procedure or may be added once the reaction vessel preparation is complete.

Described herein is the use of a glass slide that is coated with a conducting layer. The conducting layer is suitable for use in electrochemical reactions with a mixture contained within the reaction space.

In one embodiment, the reaction vessel is provided with a membrane in a reaction space, a channel or a reservoir.

In one embodiment, the membrane is suitable for preventing the flow of material across the reaction space or reservoir, or along the channel. The permeable membrane may permit flow of the material through the membrane under certain conditions. In one embodiment, a pressure differential may be provided across the membrane thereby allowing flow of material through the membrane, from the higher pressure side to the lower pressure side. The membrane may therefore be regarded as selectively permeable.

In one embodiment, the membrane is suitable for preventing the flow of certain types of material, whilst allowing the flow of other material. An example is a cation impermeable membrane, such as Nafion membranes.

In one embodiment, a low pressure source may be provided at one side of the membrane to draw material through the membrane. In one embodiment, a high pressure source may be provided at one side of the membrane to push material through the frit.

The membrane may be provided in the reaction space thereby to define two chambers. The first chamber may be a mixture chamber where reagents are permitted to mix. Once mixed, the reagents may be transferred to a reaction chamber where the reaction sequence may be initiated, for example by the addition of a further reagent or a catalyst, or by the application of heat or light, or the initiation of electrochemistry.

In one embodiment, the pore size of the membrane is at least 0.1 µm, at least 1 µm, at least 5 µm, at least 10 µm, or at least 20 µm.

In one embodiment, the pore size of the membrane is at most 100 µm, or at most 200 µm.

In one embodiment, the pore size is in a range where the lower and upper limits are selected from the values given above. For example, the pore size is in the range 20 to 100 µm.

The membrane may take the form of a glass frit. Such a frit is described herein. The membrane may have a porosity value of 2.

The dimensions of the vessel are not particularly limited. At a practical level, the dimensions of the vessel may be dictated by the dimensions of the printer assembly that is used to fabricate the vessel. However, the vessel of the invention may also be assembled from a plurality of pre-printed parts which are brought together to form the final product reaction vessel. Thus, larger vessels may be assembled from a plurality of smaller parts.

The reaction vessel of the invention may be modelled on standard reaction glassware. Thus, the vessel may be adapted such that the reaction spaces, channels and reservoirs correspond to those reaction spaces that are familiar to those of the art. For example, the reaction vessel reaction space may be modelled on a round-bottom flask, a pear-shaped flask or a conical flask. A reservoir may be modelled on a dropping funnel reservoir. A channel may be modelled on a column, an adapter head or the like. The vessel may be adapted to receive taps for controlling material flow from a reservoir and/or through a channel.

In one embodiment, the vessel has a largest cross section of at least 10 mm, at least 20 mm, or at least 40 mm.

In one embodiment, the vessel has a largest cross section of at most 100 mm, at most 200 mm, or at most 500 mm.

A reaction vessel having a cross section within these limits is capable of providing a reaction space having the volumes specified above. The volume of the reaction space, together with the dimension of the reaction vessel, provides a reaction vessel that is suitable for reactions for the preparation of analytical and as well as substantive quantities of material.

The vessel may have walls of a thickness suitable for performing reactions at reduced or increased pressure (relative to atmospheric pressure).

In principle there is no maximum limit for the thickness of a vessel wall. Thick vessel walls may be prepared simply by printing multiple layers of material. In practice there is a minimum thickness for the vessel wall which is determined by, for example, the internal diameter of the printer head nozzle through which material is delivered.

In one embodiment, a wall of the vessel is at least 0.1 mm, at least 0.5 mm, at least 1 mm, is at least 2 mm or is at least 5 mm thick.

In one embodiment, a wall of the vessel is at most 10 mm, at most 15 mm, at most 20 mm or is at most 50 mm thick.

In one embodiment, the wall thickness is in a range where the lower and upper limits are selected from the values given above. For example, the wall thickness is in the range 5 to 15 mm.

Walls having thickness values selected from the values above may have suitable strength for the use of the reaction vessel as such. Walls of such thickness do not use excess material and may be prepared within a reasonable time frame.

The wall thickness may refer to the thickness of a portion of the wall that defines the reaction space. This portion is that part of the wall separating the reaction space from the outer surface of the reaction vessel.

Where a reservoir is present in the reaction vessel, the reservoir may have a volume selected from the values specified for the reaction space. In one embodiment, the reaction space has a larger volume than that of the reservoir.

Where there are multiple reservoirs, the reaction space may have a volume more than the combined volume of the reservoirs. Thus, the reaction space is capable of holding all the material that is present in the reservoirs. In an alternative embodiment, the reaction space may have a volume less than the combined volume of the reservoirs. Here, all of the material present in the reservoirs may be prevented from entering into the reaction space. As described herein, changes in reaction space volume may be used to control the amount of reagent that is permitted in the reaction space. An alteration in the amount of a reagent present in the reaction space may be used advantageously to alter the outcome of a reaction conducted in the reaction space.

Where two reservoirs are present, the flow of material from the two reservoirs may be mixed, for example in a channel, prior to the material entering the reaction space. Such mixing may allow, for example, two reagents to pre-react. The resulting intermediate may then further react in the reaction space where it may be exposed to a catalyst, a reagent, or may be exposed to a service, such as heat, light, or redox.

Where a channel is present in the reaction vessel, its shape and dimensions are not particularly limited. In one embodiment, the cross section of the channel may be such as to limit the flow of material therethrough. The channel may therefore be used to control the rate at which a reagent is permitted to flow through the channel and enter the reaction vessel.

A channel may be provided with a pressure equalising channel, such as present in a dropping funnel, thereby to equalise pressure between the head space in the reaction vessel and the heads space in the reservoir.

The vessel is obtain or obtainable by a 3-D printing method as described herein. The printing method involves the deposition of a printable material onto a surface, layer by layer, thereby to obtain a desired 3-D object. The walls of the vessel are of a material that is printable from a 3-D printer. Alternatively, the walls of the vessel are of a material that is derived from a material, a precursor material, which is printable from a 3D printer. A suitable precursor material is converted to the material after printing, as described below.

As will be clear to the skilled person, the formation of a reaction space, a channel or a reservoir is based upon the deposition of material so as to leave voids within the printed structure. The void is the intended reaction space, channel or reservoir. As described herein the printer is programmed to deposit material at set locations across a particular printing layer. The pattern of printed material may be determined by the user, according to the user's specification or according to a pre-selected program.

The reaction vessel is obtained or is obtainable from a 3-D printing process. Thus, the material that makes up the vessel walls is material that is deliverable from a 3-D printer. Typically the material is a polymeric material, and the material may be an elastomer. Commercially available sealant material such as bathroom sealant is suitable for use.

The walls of the reaction vessel are preferably unreactive to a broad range of chemical reagents, catalyst and solvents. The material that is used to construct the vessel may be selected on the basis for the chemistry to be undertaken.

In one embodiment, reactivity may be measured with regards to a change in one or more of the volume, tensile strength or elongation of the reaction vessel wall material when exposed to a particular reagent, solvent or catalyst. Typically, a sample of vessel wall material will be tested for reactivity.

In one embodiment, the change in volume swell is 5% or less, 2% or less, 1% or less, 0.5% or less, 0.1% or less.

In one embodiment, the change in tensile strength is 15% or less, 10% or less, 5% or less, 2% or less, 1% or less, 0.5% or less, 0.1% or less.

In one embodiment, the change in elongation is 15% or less, 10% or less, 5% or less, 2% or less, 1% or less, 0.5% or less, 0.1% or less.

The change may be an increase or a decrease in the particular property under consideration.

In one embodiment the sample is a 2 mm thick film. In one embodiment, the sample is exposed to the reagent, solvent or catalyst for at least 24 hours, at least 48 hours, at least 240 hours, at least 500 hours, at least 1,000 hours, or at least 5,000 hours. The sample may be exposed to the reagent, solvent or catalyst at room temperature, for example 22° C.

In one embodiment the reaction vessel is unreactive to a solvent selected from water, DMSO, methanol, DMSO and triethylamine.

In one embodiment the reaction vessel is unreactive to acetonitrile.

In one embodiment of the invention, the vessel is healable after a breach of the structure, such as a breach that causes a loss of functional integrity. Functional integrity may refer to the ability of the vessel to hold reagents or solvent within the reaction space. The functional integrity may refer to the ability of the vessel to retain an ability to hold the pressure within the reaction space at above or below atmospheric pressure.

The term healing refers to the ability of a vessel to retain its structural integrity after a wall of the vessel has been breached. Structural integrity may refer to the ability of the vessel to retain its structure, and particularly the ability of the vessel to retain its ability to hold material in the reaction space.

In one embodiment, the vessel of the invention is self-healing. In this embodiment, the vessel of the invention is capable of retaining its structural integrity without input from an outside source. The ability of the vessel to self-heal is derived from the material which forms the vessel. As described herein, a vessel wall obtainable may be breached with a syringe needle. After removal of the needle, the wall material is capable healing around the point of needle entry, thereby to prevent material passing through the wall.

In one embodiment, a vessel is self-healing where it retains its integrity after disruption by a needle having an external diameter of at most 0.5 mm, at most 0.6 mm, at most 0.7, at most 1.0, at most 1.5 mm, at most 2 mm, or at most 5 mm.

The inventor has established that the preferred self-healing materials are capable of healing completely when disrupted by a needle having an external diameter of up to 2 mm. At needle diameters in the range 2 to 5 mm, the material may partially self-heal. Here, the vessel regains much of its integrity to be used, but some structural loss of integrity is expected.

The ability of a vessel to self-heal may be established by simple tests relating to the structural integrity of the vessel. Thus, a self-healing vessel may retain the ability to hold a volume of solvent over a set time period after re-assembly.

A suitably sealed self-healing vessel may retain the ability to hold a volume of gas, at a pressure above atmospheric pressure, over a set time period after ma-assembly.

Described above is the basic architecture for a vessel of the invention. It will be appreciated that the printing techniques describe herein are such as may be adapted to print reaction vessels of greater complexity than those described above.

The reaction vessels of the present invention may be provided with multiple reaction spaces for use in performing parallel chemical or biological reactions. The reaction spaces may be identical, and the reactions may be performed use differing reaction conditions, such as reagent ratios and amounts, to conduct a particular reaction. Additionally or alternatively, the reaction spaces may be different, either in shape or volume or some other parameter, or may have different components present on the surface of the walls defining the reaction space (e.g. different catalysts). Such changes in reaction conditions and reaction space architecture may be used to a means for optimising a reaction.

The reaction vessel may also be provided with multiple reaction spaces that are in fluid communication. Such may be useful in a multistage or flow reaction system, where a product produced in one reaction space may be transferred to another reaction space for further reaction. Additional reservoirs may be provided in fluid communication with each of these reaction spaces in order to provide additional reagents.

In one embodiment, the reaction vessel is obtainable from a plurality or reaction vessel parts, wherein at least one, for example all, of the reaction parts is obtained or obtainable by a 3-D printing method. These parts may be brought together to form a reaction vessel of the invention. Such a strategy may be useful for the assembly of a large, or complex, reaction vessel.

The parts may be joined together to form an appropriate seal, thereby to limit or prevent material exiting from the reaction vessel, and particularly from the reaction space. Suitable adhesive material may be used to hold the parts together. In one embodiment, the precursor material used in the printing procedure may be used to join parts together.

In one embodiment, the reaction vessel of the invention is separable. Thus the reaction vessel may be separated into a plurality of parts. The parts may be reassembled. The parts may be joined as described above. In one embodiment, the reaction vessel is separable along preformed joins in the reaction vessel. In another embodiment, the reaction vessel is simply broken into a plurality of parts, for example two, three of four parts, which are suitable for reassembly.

In one embodiment, the reaction vessel material is selected for the ease with which it may be separated and reassembled.

The present inventor has shown that a reaction vessel prepared from a polymer, such as silicone polymer, may be readily separated and reassembled for later use. Such reassembly does not produce a significant loss in the integrity of the reaction vessel.

The user may wish to separate the reaction vessel in order to access the reaction space, for example to retrieve product material, or for the purposes of cleaning the reaction vessel for later reuse.

3-D Printing

Printers suitable for use in printing objects in three dimensions are available commercially and are also available, in part at least, through open access and collaborative projects such as that run through the Fab@home project (www.fabathome.org). Such open access projects may alternatively provide freely available and detailed instructions for the construction of a 3-D printer. Typically, the project will also list suppliers for the various parts that are required for the constructions of a 3-D printer. The emphasis of such collaborative projects is the use of readily available, cheap, reliable and robust components. Such technology is used by the inventor in the present case, and is adapted as described herein for use in the preparation of reaction vessels, particularly those methods in which a reagent is provided to the vessel by the printer.

Printing devices will be well known to those of skill in the art, and 3-D printing devices for the preparation of objects ranging from statuettes to food products have previously been reported.

Typically, a 3-D printer will comprise a controllable printer head and a substrate (or build surface) onto which a material may be printed. The printer head is moveable relative to the substrate in a 3 axis motion (referred to in the art as x, y and z, where x and y represent the horizontal motion, and z the vertical motion). Either the printer head or the substrate or both may be moveable to achieve the required relative 3 axes of movement.

As used herein, the term print and other related terms refer to the step of delivering a substance from a printer head to the vicinity of the substrate. In the initial stages of the printing process the substance is delivered onto the substrate surface, thereby forming a layer of substance on that surface. Subsequently, the substance may be delivered onto a previously deposited layer, thereby forming another layer of substance.

A 3-D object may be prepared by printing successive layers of material. The shape and dimension of the object, and its precise architectural form are discussed in detail below.

The vessel is removable from the substrate. The substrate is chosen for its relative inertness to the material that is printed onto it. In one embodiment, the substrate does not form part of the vessel.

The substrate is not particularly limited and may be selected based on the type of printing material to be used. The printer may be supplied with a particular substrate material which may be covered as required with film or sheet or material for the particular printing process in mind. Typically, the substrate is paper or the substrate is the platform provide with the printer.

In principle the substrate may form part of the vessel, for example the substrate may form part of a base for the vessel. However, this is less preferred. For example, it is foreseeable that the join between the substance and the substrate would be a potential source of weakness in a vessel.

The printer head is adapted to print a precursor material. Typically, the printer head is provided with a printer nozzle which is in fluid communication with a reservoir for holding the printable precursor material. The printable material may be delivered from the reservoir to the nozzle as required, and the material may be dispensed from the nozzle to the vicinity of the substrate. Typically the reservoir is a syringe chamber provided with a controllable plunger. The nozzle may be a needle tip, and such are readily available in a variety of sizes from commercial sources.

The movement of the plunger may be controlled by an operating system running on an associated computer. The operation of the plunger is coordinated with the relative movement of the printer head with respect to the substrate to deliver a layer of printed material.

In one embodiment, a printer nozzle has an internal diameter of at least 0.20 mm, at least 0.25 mm, at least 0.30 mm, or at least 0.40 mm.

In one embodiment, a printer nozzle has a diameter of at most 1.0 mm, at most 1.5 mm, at most 2.0 mm or at most 2.5 mm.

Where the nozzle is a needle, the gauge of the needle is at least 10, at least 12, at least 14, or at least 16.

Where the nozzle is a needle, the gauge of the needle is at most 22, at most 23, at most 25 or at most 27.

In one embodiment, the gauge of the needle is 18.

Suitable printer nozzle sizes may be selected based on the material to be printed and the dimensions of the reaction vessel to be prepared.

In one embodiment, the nozzle and/or the reservoir may be heatable in order to maintain the precursor material at a suitable temperature for printing. The printer may also be provided with a heat source in order to cure printed material.

In some embodiment, the printer may be provided with a light source, such as a UV light source, suitable for irradiating printed material. The light source may be used to set a UV-curable precursor material.

The deposition of material from the nozzle may be controlled such that individual drops of material are printed (which may be referred to as droplet jetting). The deposition of multiple drops in close proximity can provide a desired continuous line of material that is required to form a vessel wall. The material may also be deposited from the nozzle as a continuous flow of material (which may be referred to as continuous filament writing).

The nozzle diameter may be used to influence the dimensions of the material deposited at the vicinity of the surface. The properties of the material will also influence the final dimensions of the material, as the deposited material may have some flow characteristics that cause it to spread once printed.

The rate at which precursor material is printed will depend on the precursor material in question and its setting characteristics. In turn, this will dictate the build rate i.e. the rate at which each $cm^3$ of vessel may be printed. In general, the present invention allows a reaction vessel to be prepared quickly, for example in less than a day, or in less than an hour.

The printer of the invention may be used to print one or more, such as two, different materials. In embodiments of the invention the printer is used to deliver a reaction vessel material, and the printer is used to deliver a reagent, solvent or catalyst to the reaction vessel.

In a simple adaptation of the printer, a first material is printed to a desired schedule. The reservoir containing that material is then replaced, optionally together with the nozzle, with a reservoir containing a different material to be printed, optionally together with a different nozzle, and that material is then printed to a desired schedule. Thus, the user may manually change the printer head components when additional materials are require to be printed. As necessary, the printer head components may be changed again later, when further changes in the Print material are required.

In one embodiment, the printer may be adapted to deposit two or more different materials, either simultaneously or separately. The printer may be adapted to deposit the same material, at different locations simultaneously.

Thus, the printer head may have two or more printer nozzles, where each nozzle is in fluid communication with a separate reservoir. Material may be delivered independently from each reservoir to each nozzle, thereby to allow material to be printed simultaneously or separately.

A printer head may be provided with two reservoirs in fluid communication with one nozzle. In this embodiment material from each reservoir may be printed separately. If necessary the material may be provided simultaneously, with the material mixing in or prior to the nozzle.

It is foreseeable that a printer may have an additional print head, such as a second print head, for the delivering of additional material. This second print head may be used independently of the (first) print head. In one embodiment, the second print head may be used to construct a second vessel, or a second vessel part. In one embodiment, the second print head may be used together with the first print head to print out a reaction vessel. The first and second print heads may be used to construct different portions of the same vessel. Alternatively, the second print head may follow the first print head in order to accelerate the laying down of material. The second print head may be used to print material different to that delivered from the first print head. Thus, the second print head may be used to print material having a specific function at a specific location within the vessel.

However, it is preferred that that the printer comprise a single print head, as this simplifies the printer set up and the printing procedures. As noted above, a used may change the reservoir, if necessary to allow the printing of different materials.

The printer may be in communication with and under control of a suitably programmed computer. As described herein, commercially available programs for 3-D printing are available and may be used to design and print vessels according to the present invention. Such programs allow a user to control the rate of printing as appropriate for a particular material to be printed.

In one embodiment the printer, together with the material selected, is suitable for direct writing assembly. Here, the printer is capable of delivering precursor material which sets without the need for any further intervention. Thus, it is not necessary to set the precursor using a heat or chemical treatment.

In one embodiment, the printer, or an apparatus associated with the printer, is provided with a curing system for use in the curing of a precursor material. The system is capable of curing the precursor by appropriate means, such as by heat, light or chemical means.

In one embodiment, the material comprises a reagent or catalyst that is provided for interaction with a reagent added to the reaction vessel.

The printing schedule and the printer set up may be adapted to allow the printing of a vessel where a functional component, such as a reagent or catalyst, is provided at a desired portion of the wall. For example, the printer head may be adapted to provide two sources of vessel material, where one source is the material for the vessel walls and the other is material that is mixed with the reagent or catalyst. The latter may be printed at the locations where it is desirable to have that that reagent or catalyst exposed to a space in the vessel, such as a reaction space, and/or a reservoir or channel also.

The printer may be similarly adapted to allow a coating material to be provided to the vessel walls.

In one embodiment, a reaction vessel, including reaction space components, such as reagents or catalysts, where present, may be prepared using a plurality of printers. Each printer may be set up for printing particular materials, and the reaction vessel as it is prepared may be moved from one printer to another as the construction progresses.

Material

The vessel walls comprise a material that is derived from a printable precursor. The printable precursor is printed by the printer, and once printed the precursor material sets to give the material of the vessel wall. In this step, the viscosity characteristics of the printable precursor are changed to provide a solid material that is suitable for use as wall material in a 3-D structure. The setting step, which may be regarded as the solidification of the precursor material may be achieved through solvent evaporation, gelation, or a temperature or solvent-induced phase change, amongst others.

In one embodiment, the precursor material sets at room temperature.

Thus, a precursor material has suitable rheological properties to allow it to be delivered from a printing head to a surface. The precursor material has suitable physical or chemical reactivity to form a hardened material that is suitable for forming the walls of a reaction vessel. The change from precursor material to vessel material must also be sufficiently rapid as to limit or prevent spread of a printed shape. The material product which is derived from the precursor material must have sufficient strength to act as a wall material. Thus, the material should have suitable rheological properties to act in this way.

It is preferable that the material, which provides the gross structure for the vessel, be unreactive to the reagents and solvents that are intended for use in the vessel. In some embodiments a material that has undesirable reactivity may be provided with a coating which protects the gross structure from the effect of a reagent or a solvent. This is less preferred however, as the application of a coating to the material may complicate the vessel preparation procedure.

The printable precursor may be referred to as an ink, in common with the nomenclature used in printing methods.

The precursor material is preferably a material that sets soon after printing. In this way, a printed shape is retained and with minimal flow of the printed precursor. Preferably, the setting step does not result in a substantial change, such as shrinkage, in the dimensions of the printed material. In one embodiment, the change in a dimension of a reaction vessel wall on setting is at most 10%, at most 5%, at most 2%, at most 1%, at most 0.75%, or at most 0.5%.

In one embodiment, the precursor material is suitable for printing a spanning structural element. Thus, the precursor material and the set material should be self-supporting. Thus, the printing precursor material has suitable setting characteristics and the resulting vessel material has suitable bridging strength to provide spanning structural elements.

In one embodiment, the printable material has a viscosity of a east 1, at least 5, at least 10, or at least 50 Pa s.

In one embodiment, the printable material has a viscosity of at most 100, at most 150, at most 200, or at most 250 Pa s.

In one embodiment, the printable material has a viscosity in a range with the lower and upper values selected from the minimum and maxim values given above. For example, the printable material has a viscosity in the range 5 to 150 Pa s. The viscosity of the material is at room temperature (for example 20° C.) at ambient pressure (for example 101.325 kPa).

In one embodiment, the precursor material has an extrusion rate of at least 1, at least 5, at least 10, at least 50, or at least 100 g/min.

In one embodiment, the precursor material has a flow, as measured according to ISO 7390, in the range 1 to 5 mm, or 1 to 10 mm, or 0.1 to 10 mm.

In one embodiment, the precursor material has a flow of about 2 mm.

In one embodiment, the material is cured to a depth of 1 mm within at least 1 hour, at least 3 hours, or at least 6 hours of printing.

In one embodiment, the material has a shore hardness of at least 15, at least 20 or at least 25.

In one embodiment, the material has a shore hardness of at most 50, at most 75 or at most 100.

In one embodiment the shore hardness is in a range selected from the minimum and maximum values above. For example the shore hardness is in the range 20 to 50. The shore hardness is measure according to ISO 868, Durometer Type A.

In one embodiment, the material has an elongation at break of at least 150%, at least 200%, at least 400% or at least 500%.

In one embodiment, the material has an elongation at break of at most 600%, at most 700& or at most 800%.

In one embodiment, the material has an elongation at break of about 530%.

The elongation is measured according to ISO 37.

In one embodiment, the material has a tensile strength of at least 1, or at least 2 $N/mm^2$.

In one embodiment, the material has a tensile strength of at most 5, at most 10, or at most 20 $N/mm^2$.

In one embodiment, the material has a tensile strength of about 2.5 $N/mm^2$. The tensile strength is measured according to ISO 37.

In one embodiment, the material has a lap shear strength of at least 0.1, at least 0.5, or at least 1.0 $N/mm^2$.

In one embodiment, the material has a lap shear strength of at most 5, at most 10, at most 15, at most 20 or at most 50 $N/mm^2$.

In one embodiment, the material has a lap shear strength of 2 $N/mm^2$.

The lap shear strength is measured according to ISO 4587 on aluminium (1 mm sand-blasted thick bondline).

The rheological properties of the material may be tested on a cured test film 7 days after initial curing at 25° C./50% RH for a 0.5 mm thick film.

Many different materials have been described for use in printing 3-D objects. Materials that are suitable for use in a reaction vessel include those derived from highly shear thinning colloidal suspensions, colloidal gels, polymer melts, dilute colloidal fluids, waxes, and concentrated polyelectrolyte complexes. As noted above, such materials solidify by a process of solvent evaporation, gelation, or a temperature or solvent-induced phase change.

Particular examples of colloidal materials for use in vessel printing include those based on silica, lead zirconate titanate, barium titanate, alumina, mullite, silicon nitride, and hydroxyapatite.

Examples of materials for use in the 3-D printing include those described by Cohen et al. (*Tissue Engineering* 2006, 12, 1325), Malone et al. (*Rapid Protatyping Journal* 2004, 10, 58) and Malone et al. (available via www.creativemachines.cornell.edu), which are incorporated by reference herein.

Examples of materials described therein include alginate-based materials, including those containing biological material.

Other examples of material for use in vessel printing include thermoplastics, low-melting point alloys, and materials having gelling properties and slurries. In one embodiment, the material is polypropylene. As shown herein polypropylene may be printed using a thermal printing head.

For printing, a surfactant or thinner may be added to the precursor material. The surfactant may be added to control, limit or prevent phase separation during storage in the reservoir or during the printing process. The thinner may be added to reduce the viscosity of the precursor material to a suitable level for printing. Such considerations are well known to those with familiarity with 3-D printing.

As described herein, the present inventor has used commercially available polymerisable material as the precursor material. In one embodiment, the precursor material is a silicone polymer, for example an acetoxy silicone polymer. Suitable for use in the present invention are those commercial products that find use as sealant materials for waterproof joins in bathrooms and kitchens and the like. This is a particular advantage of the present invention: readily available and relatively cheap starting materials may be used to construct the vessels described herein.

In one embodiment, the precursor material is a polymer that is solid at room temperature. The precursor may be heated to or above a temperature at which the polymer begins to flow. The polymer may be printed, and upon cooling the polymer sets.

In other embodiments the precursor material is a UV-curable epoxy resin. The resin is printed and then set by incident UV light.

The present invention provides vessels where at least a part of the vessel comprises a functional component such as a reagent or catalyst. Such reagents and catalysts may simply be incorporated into the precursor material and may be printed directly from the printer. The skilled person will appreciate that the rheological characteristics of the precursor material may change after incorporation of another material therein. The skilled person will recognise that additional components may be added to the precursor material to ensure that the rheological properties of the precursor material, including the reagent or catalyst, are suitable for printing.

As noted above, a coating may be provided on the material. The coating may be provided as a layer to protect the material underneath. The coating will therefore be unreactive to a particular reagent, product or solvent, whereas the material is. This combination may be used where a material does not have the desired lack of reactivity towards a particular reagent, product or solvent. The coating may be printed onto the surface of the material during the vessel preparation procedure. Alternatively, once the vessel is prepared by the printing process, a separate coating method may be employed.

Vessels of the invention may include components provided on or in the vessel material. Such components may be distinguished from the coating described above. The components are provided in the vessel in order to react with a reagent that is added to the reaction vessel. For example, the component may be a catalyst or an electrode surface. On the other hand a coating is provided as an unreactive coating to protect the material from the reaction species.

Computer and Computer Programme

In the methods of the present invention, the 3-D printer may be linked to and under the control of a suitably programmed computer. The computer can provide the necessary instructions to the printer to mover the printer head relative to the substrate, and the instructions to the printer head to print material. The timings of these events will be dictated by the program to a printing specification determined by the user. The sequence of print timings and locations may be referred to as the printing schedule.

Typically the computer program will be provided with a user interface that allows suitable printing schedules to be uploaded (from the internet, or from another device such as a storage device) or to be planned using the program itself. The user interface may allow the user to provide information regarding the intended use of the reaction vessel and preferred reaction parameters and reaction limitations. The program may then be capable of suggesting reaction ware suitable for the intended reaction, including type of material to be used, and the shape and dimensions of the reaction vessel. Alternatively, these features may be selected by the user. The program may determine a precise printing schedule based on these chosen features. However, the printing schedule may also be determined by the user if required.

The printer and the computer are in communication. This may be wireless communication.

The method of obtaining a suitable printing schedule and providing this schedule to the printer is not particularly limited. The printing schedule may be obtained or obtainable by the user from a third party supplier, for example a 3-D printing website. The printing schedule may be provided directly to the printer, or it may be provided to a computer in communication with the printer. As is apparent, the technique of printing material in 3-D is now established, and many programs for controlling printers are available.

In one aspect of the invention there is provided a computer implemented method of preparing a reaction vessel of the invention. The method may be a method as described herein, where the individual printing steps are controlled by a suitably programmed computer.

Additional apparatus, for use in the analysis of a reaction in a reaction vessel, may also be under the control or in communication with a suitably programmed computer. Thus, the computer may be also be used to analyse reaction outcome for a particular reaction. The computer may also analyse these outcomes, and plan the preparation of further reaction vessels, for example as part of a method to optimise a reaction using changes is reaction vessel architecture.

In a further aspect of the invention there is provided a computer implemented method of performing a reaction in a reaction vessel according to the present invention.

The present invention also provides a program for controlling a method of printing a reaction vessel of the invention. The program may be provided on a memory device such as a disk or flash memory or the like. The program may also be hosted on a website, and it may be downloadable from a website.

The computer may be provided with a user interface to allow a user to control the printing schedule thereby to control the shape, dimensions and optionally also the composition of the reaction vessel and the components that are added to it.

Typically, the user will load the 3-D printer with the material for use in the preparation of the vessel walls. The user may also load the printer with reagents or catalysts or solvents, such as first and second reagents, where such are to be provided by the vessel by the 3-D printer.

Apparatus

The reaction vessel may be adapted to hold or to interact with apparatus for use in analysis of the reaction mixture. The vessel may also be adapted to receive service supplies to the reaction space, for example to supply heat, light or mechanical perturbation to the reaction mixture.

In one aspect of the invention there is provided a reaction set up comprising a vessel of the invention and an apparatus as described herein, wherein the vessel is adapted to hold or to receive the apparatus. Alternatively, the vessel may be in communication with the apparatus. Thus, samples from the reaction space may be deliverable to an apparatus.

In one embodiment, the apparatus is a flow device suitable for controlling the flow of material into and out of the reaction vessel. In one embodiment the flow device may be a vacuum source adapted for interaction with the reaction vessel. Such a device permits material to be drawn through the reaction vessel. Similarly, the apparatus may be a pump, including a syringe, for providing material, such as solvent, into the reaction vessel. The provision of additional material into the reaction vessel may be associated with the outflow of material that was previously contained in the reaction vessel.

It is not essential for the present invention that a flow device be provided. As described herein, a flow device may be operated using gravity to move components through the reaction vessel, for example from one reaction space to another.

In one embodiment, the apparatus is an analytical apparatus. The apparatus may be suitable for use in use in temperature or pH measurements. IR or UV-VIS spectroscopies, mass spectrometry, NMR, HPLC, or redox measurements, amongst others. In some embodiments a fluid channel may be provided between the reaction space and the analytical device. An analytical sample may be taken from the reaction space to the device for analyse via the channel. In other embodiments a probe may be inserted into the reaction space. Where the spectroscopy is the measurement of electromagnetic radiation, for example IR or UV-VIS spectroscopies, an optical fibre may be place between the reaction space and the analytical apparatus.

In one embodiment the vessel is adapted for use together with an electrode system. Such a system may be used to analyse a reaction mixture, or alternatively may be used as an electron source for a particular reaction.

The apparatus may comprise a working electrode, counter electrode and optionally a reference electrode. In one embodiment one or both of the working electrode and the counter electrode is provided within or on a vessel wall. The electrodes are connectable to a power supply, a controller and a current meter.

In one embodiment, the apparatus is a camera. The camera is suitable for recording images from the reaction space. The reaction vessel may be provided with a viewing window through which images may be recorded by a camera placed outside the reaction vessel. In other embodiments, at least part of the camera may be provided in the reaction space. The camera may be in communication with a computer, such as a computer that is analysing or controlling the reaction in the reaction space.

In one embodiment, the reaction vessel is adapted to allow the reaction space to be irradiated, for example with visible or UV light. An optical cable may be provided for this purpose, which may be inserted through preformed holes in the reaction vessel. As noted above, the reaction vessel may also be provided with a window, which may also permit irradiation of a reaction mixture, by placement of the irradiation source in line with the window.

In one embodiment, the source of the irradiation may be an LED device. Such a device is particularly attractive as such are available at high volume and low costs.

Whilst in some embodiments, the light source may be powered by a power supply provided externally from the reaction vessel, it is also envisaged that the light source together with its power source may be incorporated into the reaction vessel itself. For example, during the preparation of the reaction vessel, the printing sequence may be paused to allow insertion of the light source (together with its power source) into the vessel. Printing may then be resumed, to embed the light source into the final reaction vessel. For example, LED lights may be provided at a small scale with a small battery for illumination.

In one embodiment, the reaction vessel is adapted to allow the reaction vessel to be heated or cooled. In one embodiment, the reaction vessel is adapted for placement in a heating or cooling bath. In one embodiment, the reaction vessel is provided with service fluid channels for heating and cooling fluid to pass through, thereby to heat or cool the vessel.

In one embodiment, the reaction vessel is suitable for use with a microwave device. Such a device may be used as a heating element for the reaction vessel and may be used to provide microwaves to a reaction space of the reaction vessel, for example a reaction chamber or a channel, or in one embodiment, more particularly, a region of the chamber or the channel. Microwave-generating devices for use in synthetic chemistry methods are well known, and may be readily incorporated into an apparatus of the invention.

In one embodiment, the reaction vessel is adapted for use with a stirrer. In one embodiment, the reaction set up comprises a vessel of the invention and a stirrer. In one embodiment, the stirrer is a magnetic stirrer plate. The reaction space may be adapted to receive a magnetic stirrer bar, which stirrer bar may be controlled by a suitably place magnetic stirrer plate.

In one embodiment, the stirrer is an overhead stirrer. The reaction space may be adapted to receive the overhead stirrer, which may be controlled by a controllable motor.

In one embodiment, the reaction vessel is adapted for use with a purification system. Thus, material may be moved from a reaction space of a reaction vessel and delivered to a purification device for isolation of the target product. The purification system may be used together with the analytical system to identify the product. The purification system may be a chromatographic device, such as a HPLC, for separation of components of the product mixture.

In other embodiments, the reaction vessel is prepared with a purification system as part of the vessel itself. For example, a reaction space in the reaction vessel may be provided material for capturing by-product material. Product material, which remains in solution, may be separated from the captured by-product material. Alternatively, the material may be suitable for capturing the product. By-product material, which remains in solution, may be separated from the captured product. The product may be subsequently released and isolated in a purer form. Such catch and catch-and-release purification techniques are familiar to those of skill in the art.

Methods

The present invention provides a method for preparing a reaction vessel, such as a reaction vessel described herein. 3-D printing technologies allow reaction vessels to be prepared quickly and with a high degree of design freedom. The use of uncomplicated apparatus, such as a computer and a printer, makes the process of printing a vessel accessible to a wide variety of users, of differing abilities. The preparation of the reaction vessels of the present invention may be contrasted with a traditional technique such as glassblowing, which is also used to produce bespoke reactionware. In this latter approach a highly skilled technician is require to produce a desired system of flasks and reservoirs. In contrast, the user in a 3-D printing process may only be required to load a printer with an appropriate reservoir containing the precursor material and selecting an appropriate printing schedule from a print program.

As will be apparent from the various aspects and embodiments described below, the methods for the invention are highly adapted for automation. Thus, relatively complex reaction vessels may be prepared or used with very little input required from the user. Where the invention relates to methods that involve the preparation of reaction vessel by a 3-D printing method, it is clear that the user may use complicated printing schedules that have been prepared by others and made available, for example via the internet, to users. Such printing schedules may include simple, yet precise, instructions for the user to set up the 3-0 printer, to print the reaction vessel of choice.

Generally, the method comprises the steps of:

(i) providing a programmable 3-D printer, wherein a printing head of the 3-printer is provided with a material for printing;

(ii) printing a vessel according to a printing schedule, thereby to obtain a reaction vessel.

The material for printing may be a precursor material as described herein. Once printed this precursor material may set to yield the material that forms the walls of the reaction vessel. The product of the method is a reaction vessel that is suitable for use in a reaction.

Step (ii) in the method may comprise the step of printing a plurality of vessel parts which may be assembled to give a vessel according to the present invention. However, this is less preferred. It is preferred that the method comprises the step of printing the entire vessel as one part.

The printing step (ii) comprises the step of printing the vessel onto a substrate. The printing procedure may include programmed breaks. Such breaks may be provide to allow additional components to be added to the reaction vessel, such as viewing windows, membranes, reaction surfaces and the like. The break may also be programmed to allow one or more reservoirs to be refilled. The printer may be adapted to detect the level of material in the reservoir.

If the setting requirements of the precursor material require it, the printing procedure may be paused, for example in between the printing of layers, to allow the precursor material to set to a desired level.

During a pause in the delivery of the material for printing (the precursor material), another material may be printed. For example, a reagent, catalyst, or solvent may be printed. However, it may not be necessary to pause the printing of precursor material in order to print other components into or onto the vessel. In some embodiments, multiple materials and components may be printed simultaneously, for example where a printer is provided with multiple nozzles or multiple print heads.

Thus step (ii) also includes the steps of adding to the reaction vessel a component or functional material, and preferably by 3-D printing. Where the reaction vessel has a coating, then step (ii) also comprises the step of providing that coating, and preferably by 3-D printing.

In one embodiment, there is provided the additional step of (iii) providing the vessel with a reagent or catalyst for use in a reaction. This first reagent or catalyst may be printed onto or into a reaction vessel from the 3-D printer. The use of the printer to deliver a reagent or catalyst to the reaction vessel is particularly advantageous as the reaction vessel may be prepared for reaction entirely automatically following a suitably programmed procedure.

In the methods of the invention, the printer is suitably loaded with printing materials before and during, as necessary, the methods of the invention.

Alternatively, the first reagent or catalyst may be provided to the vessel by other means independently of the printer. Additional reagents, such as a second reagent or a catalyst may also be provided, and may be delivered to the vessel by the 3-D printer or otherwise.

In step (iii) the reagent or catalyst may be provided once the preparation of the vessel is complete. Alternatively the reagent may be provided to a partially formed vessel. Such may be particularly suitable where the complexity or nature of the vessel architecture does not permit delivery of the reagent or catalyst to the final reaction vessel structure. This procedure may also be appropriate where the reaction vessel is to be sealed for the reaction to be undertaken. The reagents are added as appropriate to the vessel during assembly. Once added, the reaction vessel is then sealed.

Step (iii) may include delivering an additional reagent to the reaction vessel, and may optionally include delivering a solvent to the reaction vessel. The timing of each delivery may be controlled as appropriate.

The reagents, catalysts and solvents described here are not particularly limited, and are selected based on the reaction to be performed in the reaction vessel. Reagents, catalysts and solvents to be printed into or onto the reaction vessel are typically those that are suitable for printing. Thus, these materials are those that are easily deliverable from a printer head. Thus, these materials may be liquids, or the reagents and catalysts may be solutions or suspensions.

The reagent is not particularly limited, and is selected based on the reaction that is to be performed in the reaction space. The reagent may be an organic compound or an inorganic compound, including the salts thereof.

In one aspect of the invention there is provide a method or performing a reaction, wherein the reaction method includes the steps of preparing a reaction vessel according to steps (i), (ii) and (iii), and the additional step of (iv) reacting the reagent within the reaction vessel.

The reaction performed in the reaction vessel is not limited, and likewise the reagents, catalyst and solvent used are not particularly limited. As noted above, the material of the reaction vessel is not reactive to the components present in the reaction space. As described herein the material may hold a reagent or a catalyst which participates in the reaction. However, the material itself is not reactive to components introduced into the reaction space.

A reference to a reagent is a reference to a chemical that will undergo a change in the reaction. The change may be for example, the formation of a new chemical bond, or the loss (break) of an existing bond. The nature of the chemical bond is not limited, for example the bond may be a covalent or metal-ligand bond.

A reagent may be referred to as a starting material, particularly where that reagent shares many common structural features with the desired reaction product.

The reaction may include the reaction of a first reagent with a second reagent, optionally mediated by other reagents or catalysts. These other reagents may include acids, bases, solvents, coupling reagents, molecular sieves, scavengers, and the like.

The reaction may relate to the formation or loss of one or more bonds selected from the group consisting of a carbon-carbon bond, a carbon-nitrogen bind, a carbon-oxygen bond, a carbon-sulfur bond, a carbon-boron bond, a carbon-halogen bond, a carbon-metal bond, a nitrogen-nitrogen bond, a nitrogen-oxygen bond, a nitrogen-metal bond, an oxygen-oxygen bond, a sulfur-sulfur bond, an oxygen-metal bond, a metal halogen bond, and a metal-metal bond. The bond involved may be single or multiple bonds. The skilled person will recognise that other bond forming and bond breaking reactions may be performed in the reaction vessel of the invention.

Exemplary reactions may include those involving the formation of or transformation of a functional group selected from amide, ester, carbonate, carbamate, aldehyde, ketone, ether, imine, amine, and the like.

The reactions may include those involving the formation of or transformation of a metal complex, for example a polyoxometallate (POM).

The reaction may be a biological reaction, for example an enzyme mediated synthesis or the like. The reaction may involve biologically-derived or biologically related materials such as polypeptides, polynucleotides or polysaccharides. The reaction may involve the use of supramolecuiar assemblies or particles, such as nanoparticles.

The reaction may be a reaction such as a PCR reaction for the synthesis of DNA or RNA. The reaction may include the preparation of polypeptides, such as proteins, including enzymes.

Typically, the reaction is one that is performed at a scale of at least 0.1 mmol, at least 0.5 mmol, at least 1 mmol, at least 10 mmol, at least 100 mmol.

The scale may refer to the amount of 1 equivalent of reagent, such as a starting material, used in a reaction. The scale may refer to the theoretical maximum yield for the reaction.

Typically, the reaction is one that is performed at a scale of at least 1 mg, at least 10 mg, at least 100 mg, at least 1 g, or at least 10 g.

The scale may refer to the amount of a reagent, such as a starting material, used in a reaction. The scale may refer to the theoretical maximum yield for the reaction. In an alternative embodiment, the scale may refer to the combined mass of all the reagents, catalysts and solvent in the reaction space.

The present invention is adaptable for use with reactions at any scale. However, the present invention may usefully be used at large scale. The microfluidic systems that have previously been described for component mixing (such as Therriault et al.) are limited to those apparatus having only very small channels, and are therefore not suitable for the production of significant quantities of material.

Where a reagent or a solvent is delivered to a reaction vessel, whether by printing or otherwise, it may be delivered to a reservoir present in the reaction vessel or it may be delivered directly to the reaction space. Where two or more reagents are to be provided, they may be printed into separate locations of the reaction vessel, for example separate reservoirs.

The reaction vessel may be sealed to the atmosphere. This allows the reaction to be performed in an anhydrous and/or anaerobic atmosphere. The vessel may be suitably purged to obtain the necessary conditions. The seal may be provided by the vessel walls. Alternatively any channels in the vessel that communicate with the reaction space and the atmosphere may be sealed using standard techniques.

The 3-D printer is a printer as described herein. Thus, the printing head has a printing nozzle through which is delivered printable material from a reservoir to onto the substrate or onto a layer of delivered material.

Typically the printing protocol involves the printing of successive layers of material, one layer on top of another. The precise nature of the protocol is determined in advance with knowledge of the reaction in mind. Thus, the reaction vessel may be prepared with an appropriate number of reservoirs and channels, and the nature and number of the spaces within the reaction vessel may be set out such that an appropriate reaction initiation sequence may be used. For example, the arrangement of the reservoirs and the channels may permit the sequential addition of reagents or catalyst to the reaction space. The sequential addition may be important to the control of the reaction outcome, for example to maximise yield, minimise by-product formation and the like. Such sequential addition may also be important for safety reasons, where a particular addition sequence protocol must be followed.

In an alternative aspect the present invention provides a method of preparing a reaction vessel, the method comprising the steps of:

(i) providing a programmable 3-D printer, wherein a printing head of the 3-D printer is provided with material for printing onto a base;

(ii) printing a first reaction vessel part onto a base according to a printing schedule, thereby to obtain a first vessel part;

(iii) printing a second reaction vessel part onto a base according to a printing schedule, thereby to obtain a second vessel part;

(iv) assembling a reaction vessel from at least a first reaction vessel part and a second reaction vessel part.

The reaction vessel described herein may be used in methods of synthesis. As is apparent from the discussion herein, a vessel that is obtained or is obtainable from a 3-D printing method is suitable for use as a reaction vessel in a chemical reaction. Also provided by the present invention is the use of the reaction vessel as a vessel for a chemical reaction.

Thus, in one aspect of the invention there is provided a method of preparing a product compound, the method comprising the steps of:

(i) providing a reaction vessel as described herein or preparing a reaction vessel as described herein:

(ii) providing one or more reagents for use in the synthesis of the product compound; and (iii) permitting the one or more reagents to react in the reaction vessel, thereby to form the product compound.

The reaction vessel is obtainable or obtained by a 3-D printing method.

A product compound may be an organic or inorganic compound or a salt thereof. The product may be a biological molecule, such as a peptide, polynucleotide, or polysaccharide. The compound may also be a polymer. The reagent or reagents from which this product may be made are not particularly limited. Typically, the reaction is performed in a solvent, which is also provided. The reaction may be preformed in the presence of a catalyst.

The reaction may be conducted in a liquid, such as water or an organic solvent.

The reaction of step (iii) may be conducted in a reaction space of the reaction vessel, such as described herein.

The method optionally comprises the further step of (iv) isolating the product compound. The isolation step may separate the product from one or more of a solvent, a by-product, an unreacted reagent, or a catalyst.

In the method above, step (ii) may include the delivery of one or each of the one or more reagents to the reaction vessel by the 3-D printer.

Step (ii) may include the delivery of a catalyst and/or a solvent to the reaction vessel. The catalyst and/or a solvent may be delivered to the reaction vessel by the 3-D printer.

In one embodiment, a reagent or a catalyst, where present, may be provided in a wall of the reaction vessel and exposed to a reaction space in the reaction vessel.

In one embodiment, a reagent or a catalyst, where present, may be provided on a reaction surface provided within the reaction vessel, as described herein.

The use of a controllable reaction vessel production procedure allows a user to change aspects of the reaction vessel architecture rapidly and easily. Such changes may be used to investigate the influence of reaction vessel architectures on the outcome of a reaction. The methods of the invention allow a user to explore the changes that may be made to a reaction outcome, and thereby allows a user to identify what changes may be made to produce a more desirable reaction outcome i.e. allows the user to optimise a particular reaction. In this way, the advantages of 3-D printing technologies may be employed to chemical engineering and process chemistry problems.

According to the present invention, the used can design and optimise reactionware for a specific reaction, and the design of the reactor becomes the synthetic route to a target product. Thus, the bespoke 3-D reactionware described herein beneficially assimilates the apparatus design and chemical design, and overcomes the boundaries that exist between these technological areas.

The present invention also provides a method for analysing the outcome of a reaction, the method comprising the steps of:

(i) performing a reaction in the reaction space of a first reaction vessel, and determining a reaction outcome;

(ii) preparing a second reaction vessel using a 3-D printing method, wherein the second reaction vessel differs from the first reaction vessel;

(iii) performing a reaction in the reaction space of the second reaction vessel, and determining a reaction outcome;

(iv) comparing the reaction outcomes from step (i) and step (ii).

In one embodiment, the first reaction vessel is obtained or obtainable by a 3-D printing method.

In one embodiment, the method further comprises the step of preparing further reaction vessels and performing further reactions in those vessels, and determining the reaction outcomes.

The reaction may include the use of one or more reagents, and optionally a catalyst and/or a solvent. One or more, or each, of these may be delivered by a 3-D printer to the reaction vessel. Reactions such as those described above are suitable for analysis and optimisation in the analysis method.

In one embodiment, the method is an optimisation method for a reaction. Thus, the comparison of reaction outcomes in step (iv) may show that one reaction sequence provides a superior reaction outcome to the other reaction sequence.

The reaction outcome is a parameter that is desirable to optimise. The parameter may be the yield of a product (absolute or relative), the yield of a by-product, the identity of the product, identity of a by-product, product molecular weight (including weight average and number average molecular weights), product polydispersity, product size (for example, particle size), product shape (for example particle shape), surface enhanced resonance effect (particularly for nanoparticles), conductivity, magnetic state, quantum spin state, nuclear spin state, melting point, boiling point, circular dichromism, binding affinity (for a particular ligand, host or guest), the maximum, minimum or average temperature of the reaction; reaction time (the time taken to reach a set amount of product, including maximum product yield); redox potential; wavelengths of absorbance or emission; absorbance maximum; amongst others.

In one embodiment, more than one reaction outcome is measured.

The reaction outcome may be measured in situ by analytical devices that are connected to the reaction vessel or are provided as part of the reaction vessel. Alternatively samples may be removed from the reaction vessel, and may be analysed apart from the reaction vessel.

Reaction product mixtures may be analysed for example using IR spectroscopy, UV-VIS spectroscopy, mass spectrometry, electrochemistry, NMR, HPLC, elemental analysis, thermogravimetric analysis, flame photometry, and elemental analysis, amongst others.

Where a sample is taken from the reaction vessel it may be at least partially purified to assist analysis of the analyte of interest. In other embodiments the sample is analysed without purification.

The second reaction vessel may differ from the first reaction vessel in one or more of the parameters selected from the group consisting of:
  Reaction space volume;
  Reaction space shape;
  Reaction space wall surface area;
  Reaction space wall surface composition;
  Reaction space wall surface roughness;
  Vessel shape;
  Vessel size; and
  Vessel material.

The first and/or the second reaction vessel may be provided with a fluid channel in communication with the reaction space, wherein the fluid channel is suitable for removal of reaction material to or from the reaction space. Accordingly, the second reaction vessel differs from the first reaction vessel in one or more of the parameters selected from the group consisting of:
  channel shape;
  channel cross section; and
  number of channels.

The vessel parameter to be altered may be selected by the user either prior to the first reaction, or after the results of the first reaction are obtained. In some embodiments, the vessel changes may be made in combination with changes to a reagent, a solvent or a catalyst for use in the reaction.

Steps (ii) to (iv) may be repeated with a third reaction vessel, wherein the third reaction vessel differs from the first and second reaction vessel. A reaction may be performed in the third reaction vessel and the outcome compared to that of the first and second reaction vessels. Steps (ii) to (iv) may be repeated for further reaction vessels as often as is required to optimise the reaction architecture for a particular reaction.

The reaction may be repeated many times with many different reaction vessels. Through such a series of reactions, the user may establish an optimised reaction outcome i.e. a reaction that provides highly favourable results. Thus, in one embodiment, the reaction performed in the reaction space of the second, or subsequent, reaction vessel has an optimised reaction outcome.

In alternative aspects of the present invention, there is provided the use of the reaction vessel to prepare a formulation. The formulation may be regarded as a mixture comprising a plurality of components. Typically a component is not reactive to another component held within the mixture. Examples of formulations include polymer blends or pharmaceutical compositions. The former may comprise a plurality of polymers that differ in one or more of their molecular weight, polydispersity, composition, and Tg amongst others. The latter may comprise a pharmaceutical and one or more pharmaceutically acceptable excipients. In one embodiment, the formulation has two or more components, excluding a solvent.

The formulation may be a mixture of dry components. The formulation may be a mixture of components that are miscible or immiscible. Thus, the formulation encompasses colloids, where one component may be dispersed in a continuous phase of another component.

The reaction vessel of the invention may be used in a method to combine two or more components thereby to yield a formulation.

In one aspect there is provided a method for preparing a formulation, the method comprising the steps of:

(i) providing a reaction vessel that is obtained by a 3-D printing method, wherein the reaction vessel has a reaction space;

(ii) providing two or more components for incorporation into a formulation; and (iii) permitting the two or more components to intermix within the reaction space, thereby to form the product formulation.

In this method, one or more of the components may be delivered to the reaction by a 3-D printer.

The present invention also provides methods for analysing a property of a formulation, the method comprising the steps of:

(i) preparing a formulation in the reaction space of a first reaction vessel, and determining a formulation property;

(ii) preparing a second reaction vessel using a 3-D printing method, wherein the second reaction vessel differs from the first reaction vessel;

(iii) preparing a formulation in the reaction space of the second reaction vessel, and determining a formulation property;

(iv) comparing the reaction outcomes from step (i) and step (ii).

The first reaction vessel may be obtained by a 3-D printing method. In one embodiment, the method further comprises the step of preparing further reaction vessels and performing further formulations in those vessels, and determining the formulation properties.

The formulation property is a parameter of the formulation that is desirable to optimise. The parameter may be the stability of the formulation (including mechanical and thermal stability), melting point, formulation time (the time taken to reach the desired degree of mixing), amongst others.

The formulation property is measured using analytical techniques appropriate for the formulation parameter under consideration.

The second reaction vessel may differ from the first reaction vessel in one or more of the parameters selected from the group consisting of:
 Reaction space volume;
 Reaction space shape;
 Reaction space wall surface area;
 Reaction space wall surface composition;
 Reaction space wall surface roughness;
 Vessel shape;
 Vessel size; and
 Vessel material.

The first and/or the second reaction vessel may be provided with a fluid channel in communication with the reaction space, wherein the fluid channel is suitable for removal of reaction material to or from the reaction space.

Accordingly, the second reaction vessel differs from the first reaction vessel in one or more of the parameters selected from the group consisting of:
 channel shape;
 channel cross section; and
 number of channels.

The vessel parameter to be altered may be selected by the user either prior to the first formulation, or after the results of the first formulation are obtained. In some embodiments, the vessel changes may be made in combination with changes to a component for incorporation into the formulation.

Steps (ii) to (iv) may be repeated with a third reaction vessel, wherein the third reaction vessel differs from the first and second reaction vessel. A formulation may be performed in the third reaction vessel and the outcome compared to that of the first and second reaction vessels. Steps (ii) to (iv) may be repeated for further reaction vessels as often as is required to optimise the reaction architecture for a particular formulation.

The formulation may be repeated many times with many different reaction vessels. Through such a series of formulations, the user may establish an optimised formulations outcome i.e. a formulation that provides highly favourable results. Thus, in one embodiment, the formulation performed in the reaction space of the second, or subsequent, reaction vessel has an optimised formulation property.

Also provided is a formulation obtained or obtainable by the methods described herein.

In a further aspect of the invention there is provided a hydrothermal or solvothermal method, the method comprising the steps of:

(i) providing a reaction vessel as described herein, where the reaction vessel has a reaction space, and the reaction space holds one or more materials in a solvent, wherein the reaction space is sealed;

(ii) heating the one or more materials in the reaction space, optionally allowing the materials to react;

(iii) subsequently allowing the contents of the reaction space to cool; and (iv) optionally accessing the reaction space by breaking the seal;

(v) optionally isolating a material from the reaction space.

The method may be suitable for use in the preparation of crystalline products. In this embodiment, there is no reaction in step (ii).

The present inventor has found that the materials for use in preparing 3D-printed reactions vessels are suitable at withstanding relatively high temperatures and relatively high and low pressures. In this way they are suitable for use in hydrothermal or solvothermal synthetic techniques, including crystallisation.

OTHER PREFERENCES

Each and every compatible combination of the embodiments described above is explicitly disclosed herein, as if each and every combination was individually and explicitly recited.

Various further aspects and embodiments of the present invention will be apparent to those skilled in the art in view of the present disclosure.

"and/or" where used herein is to be taken as specific disclosure of each of the two specified features or components with or without the other. For example "A and/or B" is to be taken as specific disclosure of each of (i) A, (ii) B and (iii) A and B, just as if each is set out individually herein.

Unless context dictates otherwise, the descriptions and definitions of the features set out above are not limited to any particular aspect or embodiment of the invention and apply equally to all aspects and embodiments which are described.

Certain aspects and embodiments of the invention will now be illustrated by way of example and with reference to the figures described above.

EXPERIMENTAL AND RESULTS

General Experimental

All chemical reagents and solvents were purchased from Sigma Aldrich and used without further purification except for 98% dimethylamine hydrochloride, carbon black super conductive (99%) and phosphomolybdic acid (all Alfa Aesar) and the acetoxy-silicone polymer (LOCTITE® 5366 bathroom sealant, Loctite Corp.). Pd/C (10% b/w) was supplied by Lancaster. The synthesis of 5-(2-bromoethyl) phenanthridinium bromide has been reported previously (see Parenty et al. *J. Org. Chem.* 2004, 69, 5934-5946).

3D-printing was achieved on a Fab@Home Version 0.24 RC6 freeform fabricator assembled from a kit by the authors. Labware was designed digitally using Rhino3d and uploaded to the freeform fabricator for printing.

Crystallisations were monitored using a Keyence VHX-600 (Gen II) digital microscope with a 20-200× lens.

Carbon, nitrogen and hydrogen content were determined by the microanalysis services within the Department of Chemistry, University of Glasgow using an EA 1110 CHNS, CE-440 Elemental Analyzer. Flame Photometry (FP) analyses to determine sodium content were performed at the Environmental Chemistry Section, School of Chemistry, University of Glasgow on a Corning Flame Photometer 410. Thermogravimetric analysis was performed on a TA Instruments Q 500 Thermogravimetric Analyzer under nitrogen flow at a typical heating rate of 5° C. $min^{-1}$. Fourier-transform infrared (FT-IR) spectroscopy: unless stated otherwise, the materials were prepared as KBr pellets and FT-IR spectra were collected in transmission mode using a JASCO FT-IR 4100 spectrometer. Wavenumbers are given in $cm^{-1}$; intensities are denoted as w=weak, s=sharp, m=medium, br=broad, s=strong.

Electrochemistry was performed using a CH Instruments CHI760D potentiostat, with a Pt wire counter electrode and Ag/AgCl reference electrode at room temperature and pressure, under ambient atmospheric conditions. The active area of the glass ITO slide (working electrode) in contact with the electrolyte was 2.0 $cm^2$. All NMR spectra were recorded on a Bruker Advanced 400 MHz machine at 298 K, and chemical shifts are reported in ppm relative to residual solvent. All coupling constants (J) are given in Hz and standard peak descriptions are abbreviated as follows: s; singlet, d; doublet, t; triplet.

UV-Vis spectra were collected on a TIDAS 100 spectrophotometer (J&M Analytik AG), illuminating with a 150 W Newport Hg arc lamp (Oriel Instruments, USA) equipped with a fibre optic cable. All spectra are normalised to the absorbance recorded at 500 nm. Mass spectra were obtained on a JEOL JMS 700 spectrometer operating in fast atom bombardment (FAB) mode.

Printer and Control Program
Design Software

The 3D-printed labware used in this work was designed on the commercial 3D CAD software Rhino 3D (available as of January 2012 from http://www.rhino3d.com/) although in principle any 3D modelling/CAD software with the ability to export models in a .STL file format would suffice for this, and there are a number of suitable alternative free/open source candidates available on the internet.

Device Design

The devices were designed to accommodate two pre-mixing reactant chambers and an initial mixing chamber which is separated by a sintered glass frit (porosity 2) from a final reaction chamber which incorporates a viewing port composed of a glass cover slip or ITO-coated glass slide. The sintered glass frit and viewport represent the non-printed sections of the labware. Each of the reactant holding chambers has a volume of 2 mL; the mixing chamber has a volume of 4.4 mL; and the final reaction chamber has a volume of 4.3 mL.

The device design was exported as a .STL file which was then interpreted by the Fab@Home software and transmitted to the printer. The device was printed using commercially available acetoxy silicone polymer as an inexpensive, robust and quick-curing material which was inert to the chemicals to be used in the subsequent experiments. After printing and curing at room temperature for 12 hours, the reactionware was repeatedly washed with distilled water until all traces of acetic acid (released during curing) had been removed. Using this approach, no serious adverse effects were noted from acetic acid seepage into solution (which would lower the solution pH) during the subsequent reactions.

The printing was conducted in a layer-by-layer fashion by the Fab@Home printer with pre-programmed pauses in the printing process to allow the insertion of the non-printed sections of the design. Overhanging regions of the device were supported by filling the printing device with distilled water upon which the overhanging layers were printed. This water was removed and the completed device washed with water prior to use.

The primary material printing material of choice (acetoxy-silicone polymer, LOCTITE® 5366 bathroom sealant) was found to be compatible with a number of solvents suitable for use in organic, inorganic and biological syntheses. It was established that the reaction vessel was not suitable for use with other solvent systems. For example, in acetone, toluene (vide infra), dichloromethane and chloroform, the polymer was found to swell considerably (especially in the chlorinated solvents) when placed in contact with these solvents for more than a few minutes. Some swelling was also observed with acetonitrile. The immediate effect of this was to close the internal channels within the reactionware. However, there was no noticeable swelling when water, methanol, DMF or DMSO were used as solvents, and in all these cases internal channels remained open and tight seals were formed with the vacuum needles inserted through the walls of the reaction chambers.

Active (conductive or catalytic) materials for printing were prepared by first thinning the original silicone polymer with toluene (30% by mass) followed by the addition of the appropriate active material. For example, a conductive printing material was achieved by adding 0.5 g of carbon black to 6 g of a silicone/toluene mixture. This mixture gave a conductive paste of sufficient viscosity to print in a similar manner to the original silicone polymer. Commercially available conductive silicone materials are also available. An example catalytically active material was obtained by mixing 0.5 g Pd/C (10% Pd why) to 6 g of a silicone/toluene mixture. This mixture gave a conductive paste of sufficient viscosity to print in a similar manner to the original silicone polymer. Upon curing the materials experienced some shrinking due to the evaporation of the toluene thinning agent. Once devices prepared with these materials had cured in a similar manner to the silicone only devices, they were placed under vacuum for 18 hours to ensure complete removal of the toluene and subsequently washed with water before use.

Figure 7:
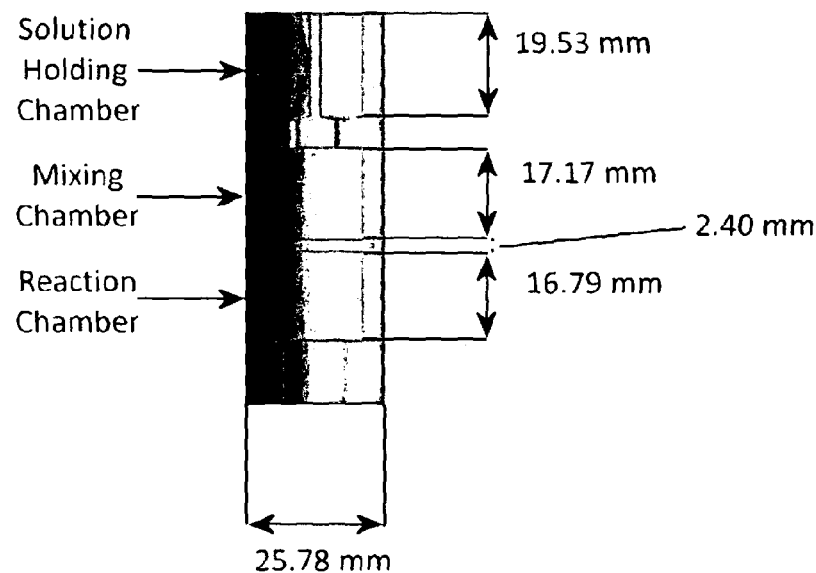
FIG. 7 is a schematic illustrating the 3-D printed device used for inorganic and organic synthesis, with dimensions given (actual measured dimensions given in brackets).
Figure 8:
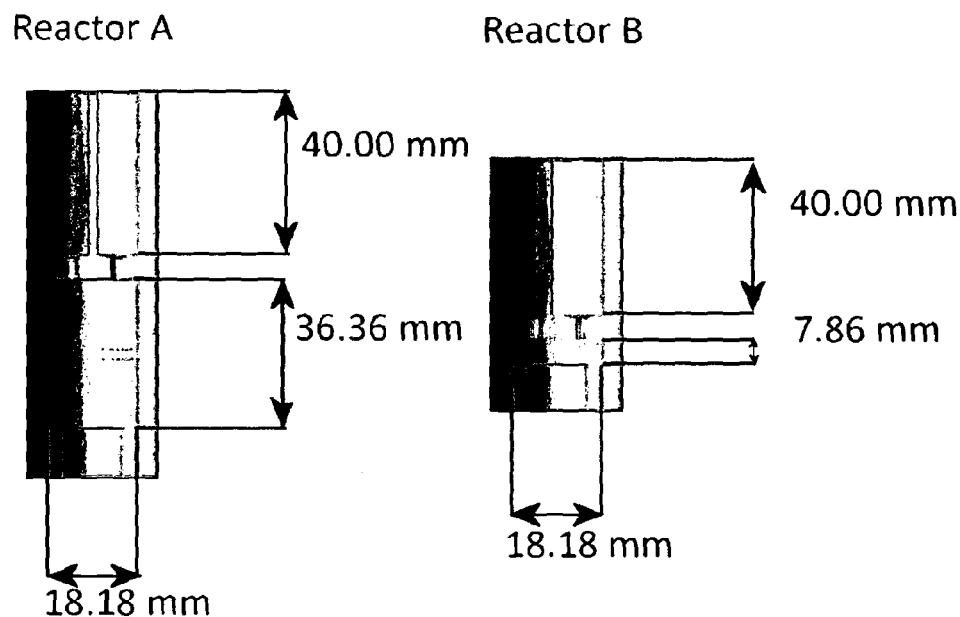
FIG. 8 is a schematic illustrating reactors A and B as used for selective heterocycle syntheses, with dimensions given (actual measured dimensions given in brackets).

The printed devices conformed to the CAD design dimensions with less than 5% difference in any dimension, indicating a high degree of accuracy in the printing process (see FIGS. 7 and 8). The size of the lines of silicone polymer printed by the device is dependent on the exact dispensing nozzle used in the printing process (the Fab@Home software allows the user to specify nozzle sizes so that products of a consistent size can be printed). In this work, reactors were printed using a tapered dispensing tip with an internal diameter of 0.838 mm, with a corresponding printed polymer bead size. The choice of dispensing tip depends largely on the material properties of the material to be printed. Various tapered dispensing tips are commercially available with internal diameters ranging from 0.37-1.60 mm. The 3D-printer utilized in this work was configured with two syringe tools which were filled with the appropriate printing materials, allowing the printer to deposit two materials without changing the device configuration. Changing this configuration and refilling the printable materials was achieved via a facile process during which the software automatically paused the print process and the syringe in question was replaced with a new one. These syringe tools are fully reusable.

Reactions in a 3-D Reaction Vessel
Inorganic Synthesis

Figure 2:
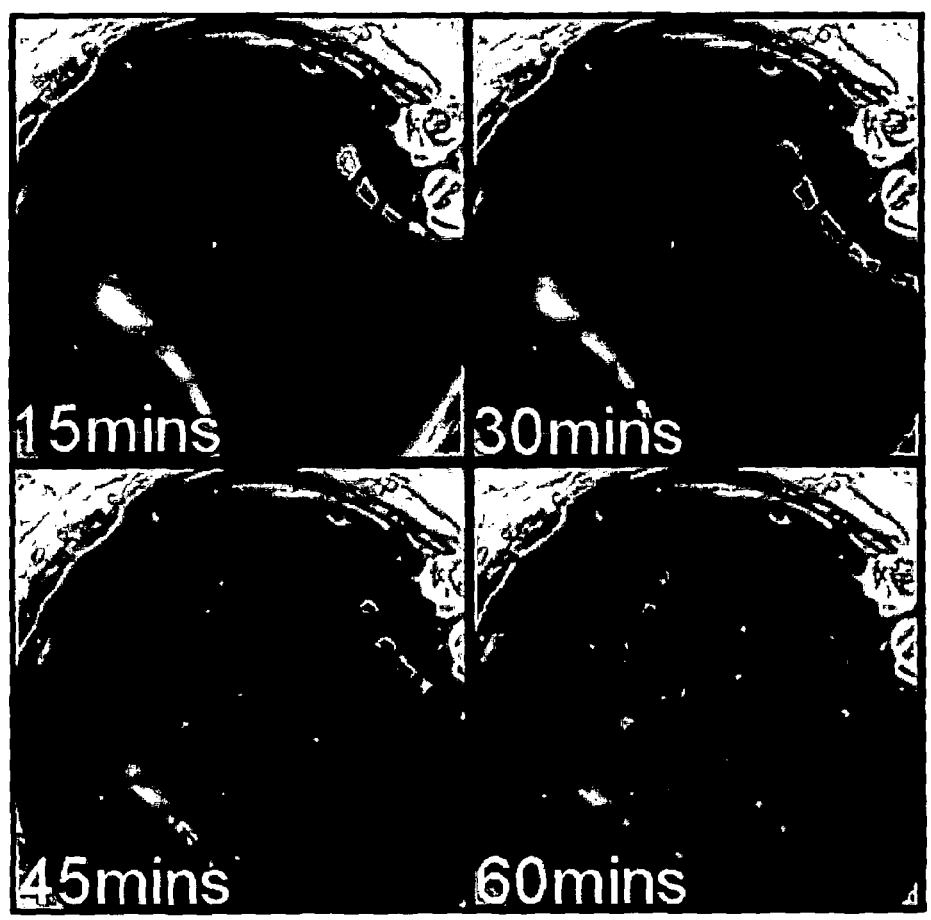
FIG. 2 is a series of photographs showing the crystallisation of $(C_2H_8N)_7Na_4[W_{19}Co_2O_{61}Cl(SeO_3)_2(H_2O)_2]$ $Cl_2.6H_2O$ at various times (at 15, 30, 45 and 60 minutes) after initial mixing of the starting materials in a vessel of the invention.

The vessel was used in the preparation of an inorganic nanocluster assembly. An aqueous solution of $CoCl_2$ was printed into one solution reservoir, and an acidic solution of the dilacunary polyoxotungstate $[Se_2W_{19}O_{66}(H_2O)]^{12-}$ (prepared using an adaptation of the procedures described by Kortz et al. *Angew. Chem. Int. Ed.* 2001, 40, 3384-3386) was loaded into another reservoir. The two solutions remained in their respective reservoirs and did not flow into the mixing chamber (reaction space) until induced to do so. To this end, a needle attached to a vacuum source was inserted through the wall of the reaction chamber to suck the two solutions into the mixing chamber, through the frit and thence into the lower reaction chamber at a controlled rate. Upon removal of the needle, the walls of the reaction chamber spontaneously re-sealed, making the chamber watertight. The subsequent crystallisation events were monitored via the transparent viewing window incorporated into the device. FIG. 2 shows this crystallisation process at various time intervals of 15, 30, 45 and 60 minutes from reaction start.

Figure 3:
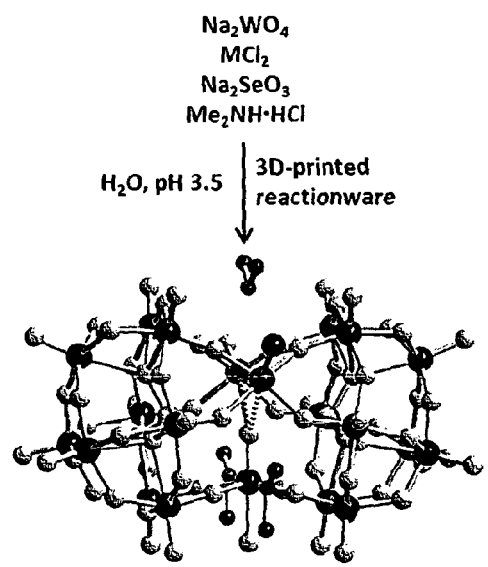
FIG. 3 is a reaction scheme for the preparation of the polyoxymetallate having the structure $\{(C_2H_8N)_3[W_{19}M_2O_{61}Cl(SeO_3)_2(H_2O)_2]\}^{6-}$. The product structure is represented in ball and stick mode with the protons omitted for clarity (M=Co(II) or Mn(II).

Importantly, once the precursor solutions had passed into the mixing chamber, the whole vessel could be held upside-down and shaken repeatedly without leakage of the solutions. When crystals of a suitable size had formed (typically within 10-60 minutes) the vessel was cut in half with a scalpel, and the crystals were removed and analysed by X-ray crystallography, FT-IR, thermogravimetric analysis and elemental analysis. The crystal structure of 1 (FIG. 3) contains a classic sandwich type anionic cluster $[W_{19}CO_2O_{61}Cl(SeO_3)_2(H_2O)_2]^{9-}$ which is formed of two tri-lacunary $[W_9O_{30}(SeO_3)]^{8-}$ building blocks (average Se—O bond length=1.70(2) Å) and a central trigonal planar core (see Kortz et al. ibid). This core contains an octahedral $\{WO_6\}$ unit and two $(CoO_6)$ centres. One terminal oxo ligand of the $\{WO_6\}$ coordinates to both the $\{CoO_6\}$ units, whilst the terminal water ligand on one Co centre is substituted by a chloride. It is interesting to note that, in addition to a certain number of amines acting as cations and hydrogen bonding to the cluster, there are also extra dimethyl ammonium ions disordered around the cluster in the crystal structure. It is possible that an excess of dimethyl ammonium hydrochloride accelerates the crystallisation process (allowing single crystals to form in only a few minutes) whereas no single crystalline product can be isolated after a week when such amines are absent.

The cleaved 3D-printed vessel was then washed with water and reconstituted by simply applying a thin layer of acetoxy-silicone polymer to the cut edges, pressing the two halves of the vessel together by hand and then leaving it to set for an hour. It was subsequently successfully reused as before, this time using aqueous solutions of $MnCl_2$ and $[Se_2W_{19}O_{66}(H_2O)]^{12-}$ to prepare $(C_2H_8N)_8Na_3[W_{19}Mn_2O_{61}Cl(SeO_3)_2(H_2O)_2]Cl_2.6H_2O$ (2). Crystallographic unit cell checks established that this compound had the same structure as compound 1.

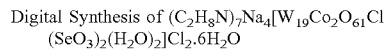
Digital Synthesis of $(C_2H_8N)_7Na_4[W_{19}Co_2O_{61}Cl(SeO_3)_2(H_2O)_2]Cl_2.6H_2O$ (1)

$CoCl_2.6H_2O$ (0.50 g, 2.10 mmol) was dissolved in water (20 mL) and loaded into one syringe on the freeform fabricator. Meanwhile, dimethylamine hydrochloride (2.00 g, 24.5 mmol), $Na_2SeO_3$ (0.40 g, 2.31 mmol) and $Na_2WO_4.2H_2O$ (5.00 g, 15.2 mmol) were dissolved in water (30 mL), and the pH of the solution made to 3.5 with 37% hydrochloric acid. 20 mL of this tungstate solution was placed in the second syringe of the freeform fabricator. The 3D-printed labware was then positioned appropriately, after which a fabricator program was put in train, whereby the printer filled one holding chamber with the cobalt solution (1 mL) and filled the other holding chamber with the tungstate solution (1.5 mL). Video recording was then initiated and a needle-line inserted through the wall of the reaction chamber. Upon application of a vacuum to this needle-line, the two solutions were sucked into the mixing chamber and thence through the frit into the reaction chamber at a controlled rate. The solution in the reaction chamber was observed to turn green (from pink) over the course of a few minutes, and green crystals of compound 1 were seen to crystallise out from around this time. Crystallisation was monitored via video for an hour, after which time the 3D-printed device was cut in half through the wall of the reaction chamber, and then dark green crystals of 1 recovered. Yield: 61% based on tungsten (0.14 g, 0.025 mmol). I.R. (KBr disk, v/cm$^{-1}$): 3335.1, 3155.6, 1618.3, 1465.9, 951.2, 858.3, 825.6, 727.2, 695.4, 628.8. Elemental analysis, calc. for $C_{14}H_{72}Cl_3Co_2N_7Na_4O_{75}Se_2W_{19}$: C, 3.05; H, 1.32; N, 1.78; Na, 1.67. Found C, 3.24; H, 1.35; N, 1.88; Na, 1.4. TGA water and amine loss from 20 to 200° C. calculated (found) %: 5.34 (5.24).

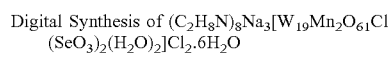
Digital Synthesis of $(C_2H_8N)_8Na_3[W_{19}Mn_2O_{61}Cl(SeO_3)_2(H_2O)_2]Cl_2.6H_2O$ (2)

Compound 2 was synthesised in an analogous fashion to compound 1, with the exception that the cobalt solution was substituted for a manganese solution as follows: $MnCl_2$ (0,200 g 1.60 mmol) was dissolved in water (20 mL) and loaded into one syringe of the freeform fabricator. Printing then followed the same schedule as that for compound 1. Upon mixing, orange-brown crystals of 2 formed from the brown solution over 1 hour. Yield: 53% based on tungsten (0.12 g, 0.021 mmol). I.R. (KBr disk, v/cm$^{-1}$): 3330.2, 1620.3, 1461.3, 954.2, 856.3, 821.6, 725.2, 695.7, 628.6. Elemental analysis, calc. for $C_{16}H_{60}Cl_3Mn_2N_6Na_8O_{75}Se_2W_{19}$: C, 3.48; H, 1.46; N, 2.03; Na, 1.26. Found C, 3.44; H, 1.23; N, 2.01; Na, 1.2. TGA water and amine loss from 20 to 200° C., calculated (found) %: 6.01 (6.07).

Organic Synthesis

Figure 4:
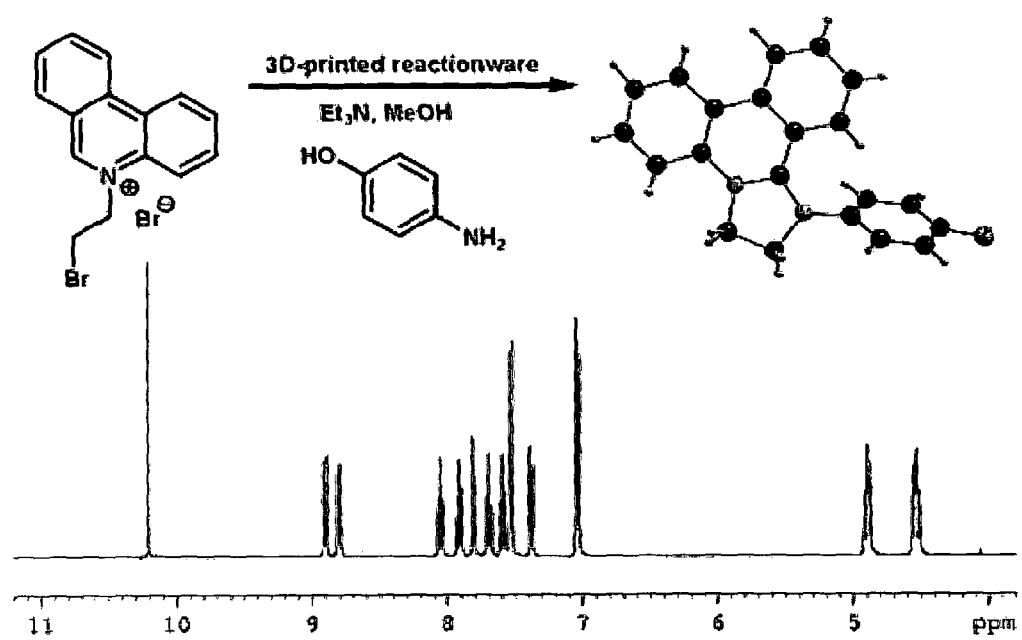
FIG. 4 shows a reaction scheme for the preparation of phenanthridine-based heterocycle 3 from 4 and 5 as prepared in a reaction vessel according to an embodiment of the invention.

The vessel was used in an organic synthesis. Specifically, the phenanthridine-based heterocycle 3 was synthesised by the reaction of 4-aminophenol, $Et_3N$ and 5-(2-bromoethyl)phenanthridinium bromide in methanol (see FIG. 4 also). Upon mixing in the 3D-printed labware, the reaction mixture turned an amber colour, and crystals of 3 suitable for X-ray diffraction were obtained from the liquor after 96 hours. The structure thus obtained is shown in FIG. 4, along with the $^1$H NMR of compound 3 in $d_6$-DMSO. In particular, the formation of a new 5-membered ring was noted, created by the nucleophilic attack of the amine group of 4-aminophenol at the α-position to the pyridyl nitrogen (see Parenty et al. *J. Org. Chem.* 2004, 69, 5934-5946). The two triplets at 4.9 and 4.5 ppm in the $^1$H NMR (FIG. 4, bottom) correspond to the two —$CH_2$— units in this 5-membered ring, and the compound evidently has a high bulk purity by $^1$H NMR.

Synthesis of 1-(4-Hydroxy-phenyl)-2,3-dihydro-1H-imidazo[1,2-f]phenanthridin-4-ylium bromide; $C_{21}H_{17}BrN_2O$ (3)

A solution of 5-(2-bromoethyl)phenanthridinium bromide (50 mg, 0.14 mmol, 2.0 eq) in MeOH (1.5 mL) was loaded into one solution holding chamber of the 3D-printed labware and a solution of 4-aminophenol (7.4 mg, 0.070 mmol, 1.0 eq) and TEA (29 μL, 0.20 mmol, 3.0 eq) in MeOH (0.5 mL) was placed in the other holding chamber. The two solutions were then induced to flow into the mixing chamber and thence into the lower reaction chamber under the influence of a vacuum line inserted through the wall of the reaction chamber as before. After the two solutions had been sucked into the lower chamber, the reaction mixture was shaken vigorously for 1 min then left to stand for 96 h. Brown needle-like crystals were harvested by cutting open the labware. These were washed with MeOH and diethyl ether before drying under vacuum to give a brown crystalline solid, m.p. 350° C. (dec.); 19 mg, 0.049 mmol, (69% based on 4-aminophenol). $^1$H NMR ($d_6$-DMSO, 400 MHz) δ: 10.21 (s, 1H), 8.90 (d, 1H, J=8.0), 8.80 (d, 1H, J=8.0), 8.05 (t, 1H, J 8.0), 7.91 (t, 1H, J=8.0), 7.79 (d, 1H, J=8.0), 7.69 (t, 1H, J=8.0), 7.59 (t, 1H, J=8.0), 7.53 (d, 2H, J=9.2), 7.38 (d, 1H, J=8.0), 7.03 (d, 2H, J=9.2), 4.90 (t, 2H, J=10.6), 4.53 (t, 2H, J=10.6); $^{13}$C NMR ($d_6$-DMSO, 100 MHz) δ: 158.4 (C), 152.5 (C), 135.2 (CH), 134.9 (C), 132.7 (C), 131.5 (CH), 129.9 (C), 128.6 (CH), 128.1 (2×CH), 126.9 (CH), 125.5 (CH), 124.2 (CH), 124.0 (CH), 120.2 (C), 117.1 (2×CH), 116.0 (CH), 115.4 (C), 54.6 ($CH_2$), 46.6 ($CH_2$); IR (KBr, $cm^{-1}$) 3448 (w), 3108 (s), 3021 (m), 1609 (s), 1595 (s), 1576 (s), 1547 (s), 1513 (s), 1494 (s), 1446 (s), 1391 (m), 1303 (s), 1262 (s), 1227 (s), 1166 (s), 845 (s), 788 (s), 751 (s), 718 (s), 666 (s); MS (FAB) m/z (%) 313 (14) (M), 232 (17), 157 (32), 79 (100); Anal. Calcd for $C_{21}H_{17}BrN_2O$; C, 64.13; H, 4.36; N, 7.12. Found: C, 63.96; H, 4.33; N, 7.08.

Heterogeneous Catalysis

Figure 9:
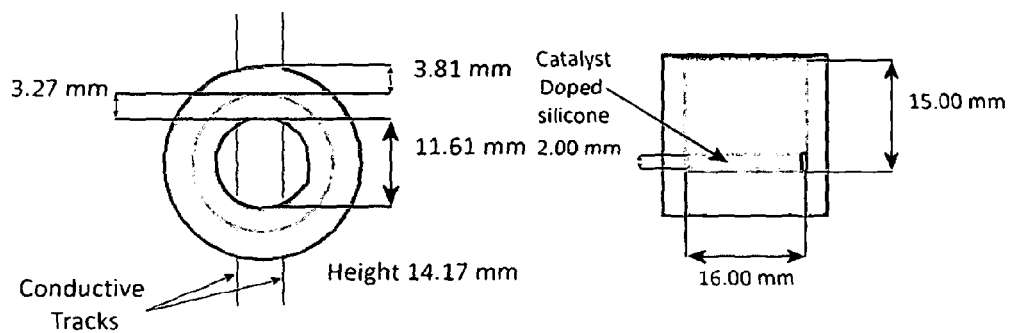
FIG. 9 is a schematic of a device used for electrochemical synthesis (left) and catalytic reduction of styrene (right), with dimensions given (actual measured dimensions given in brackets). The designed and measured thickness of the catalyst-doped silicon vary by more than 5% due to shrinkage upon removal of the toluene thinner. The difference in this case is 7%.
Figure 10:
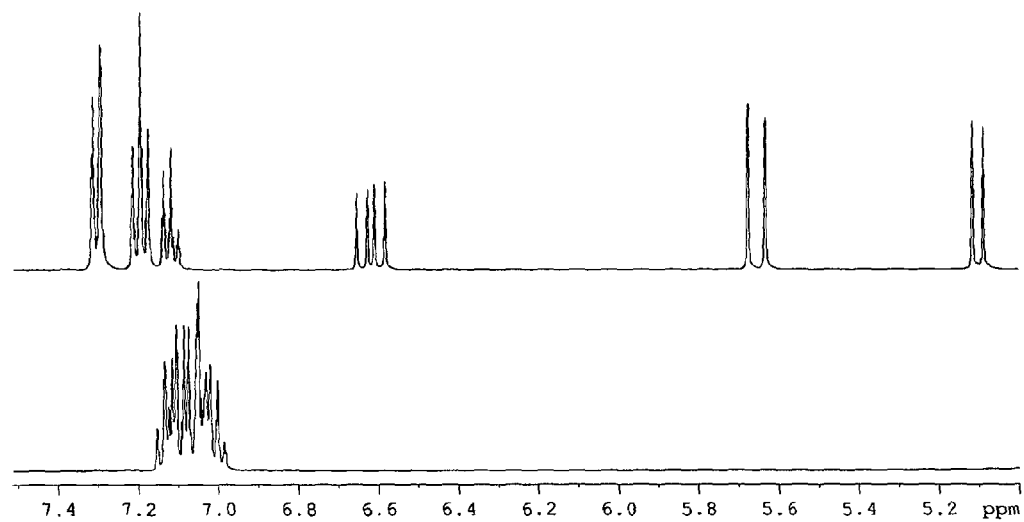
FIG. 10 is a series of $^1H$ NMR spectra of a product (in $d_4$-MeOD) collected after the catalytic reduction of styrene by Pd/C doped silicone polymer in a 3-D printed reaction vessel (bottom) and a product collected under similar conditions in the absence of the Pd/C doped silicone catalyst (top). Aliphatic signals are not shown as they are obscured by peaks arising from the triethylsilane reagent. The complete disappearance of the signals from the protons attached to the carbon-carbon double bond (multiplet at 6.6 ppm and doublets at 5.7 and 5.1 ppm) in the lower spectrum shows complete reduction of the C=C bond.
Figure 11:
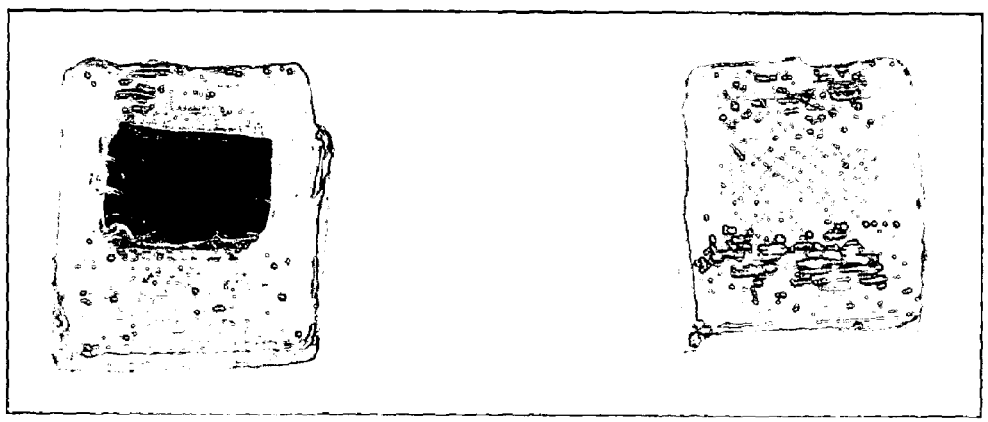
FIG. 11 is a photograph of a 3-0 printed reaction vessel according to an embodiment of the invention, wherein the vessel was printed using a Pd/C doped silicone section (left) and a 3-D printed reaction vessel printed using only inert silicone polymer (right).

The catalytic reduction of styrene in a 3D-printed reaction chamber was achieved via a modified literature procedure (see Mandel et al. *J. Org. Chem.* 2007, 72, 6599-6601). A solution of styrene (15 mg, 0.14 mmol) and triethylsilane (0.251 g, 2.1 mmol, 15 eq.) in $d_4$-MeOD was introduced into a 3D printed reactor chamber (see FIGS. 11 and 9) containing a Pd/C/silicone polymer catalyst section and stirred slowly for 30 mins. During this time bubbles of hydrogen were seen to be generated on the surface of the catalyst-containing section of the printed labware. After 30 mins of stirring, no further bubbles were formed. The MeOD solution was removed by pipette and analysed by $^1$H NMR. This analysis (see FIG. 10), revealed that the styrene had been completely reduced to ethyl benzene, leaving no trace of the starting material. A similar experiment performed in a 3D-printed reactor chamber of similar design, but without the Pd/C catalyst-doped silicone section was allowed to stir for 2 hours, after which time a $^1$H NMR spectrum was collected which showed no conversion of styrene to ethyl benzene.

The 3D-printed catalytic reactor could be washed with appropriate solvent and reused.

Analysis

Labware suitable for analytical and spectroscopic techniques could also be produced, showcasing the potential to monitor reactions in situ using such reaction vessels prepared by 3-D printing techniques. The reaction vessel of the invention was adapted for electrochemical analysis.

To this end, an adapted version of the reaction vessel shown in FIG. 1C was printed, whereby the frit was omitted and the microscope cover-slip viewing port was replaced by a glass slide coated in a thin layer of the transparent conductor indium tin oxide (ITO), such that the ITO-coated surface faced into the reaction space. Initially, the central chamber of the device was charged with 2 mL of an aqueous 5 mM solution of phosphomolybdic acid (PMA) in 0.1M $H_2SO_4$. A thin Ag/AgCl reference electrode (the middle left cable in FIG. 5A) and a Pt wire counter electrode (upper left cable) were then inserted into this solution through the pre-printed apertures between the solution holding chambers and the reaction chamber, whilst the ITO slide was connected to a potentiostat as the working electrode (lower left cable, see FIG. 5A). Cycling from −0.2 V to +1.0 V and back to −0.2 V (vs. Ag/AgCl) in this three-electrode set-up then produced the cyclic voltammogram show in FIG. 5D, which shows four reversible redox processes centered at +0.45, +0.30, +0.10 and −0.10 V vs. Ag/AgCl, in agreement with literature values (see Tanaka et al. *Inorg. Chem.* 1982, 21, 1662-1666).

Upon termination of potential cycling at −0.2 V, the initially yellow solution had taken a slightly blue hue, characteristic of reduced polyoxomolybdates. The colour change could be monitored in situ using the configuration shown in FIGS. 5B and 5C, by inserting a fibre-optic cable through one of the pre-printed holes in the top of the reaction vessel (the Pt counter electrode was moved and pushed through the re-sealable lid to make this possible), which was connected to the input port on a TIDAS UV-visible spectrophotometer. The input light source was provided by a 150 W broad-spectrum Hg arc lamp, which was clamped underneath the apparatus, such that the sample was irradiated from below, through the ITO window, during acquisition of the spectra. Comparison of the spectra obtained before and after the cyclic voltammogram (FIG. 5E) shows the appearance of a new broad peak centred around 750 nm, consistent with the slight blue tinge now visible in the solution and with previous spectroelectrochemical studies on this compound (Tanaka et al. ibid.).

Figure 5:
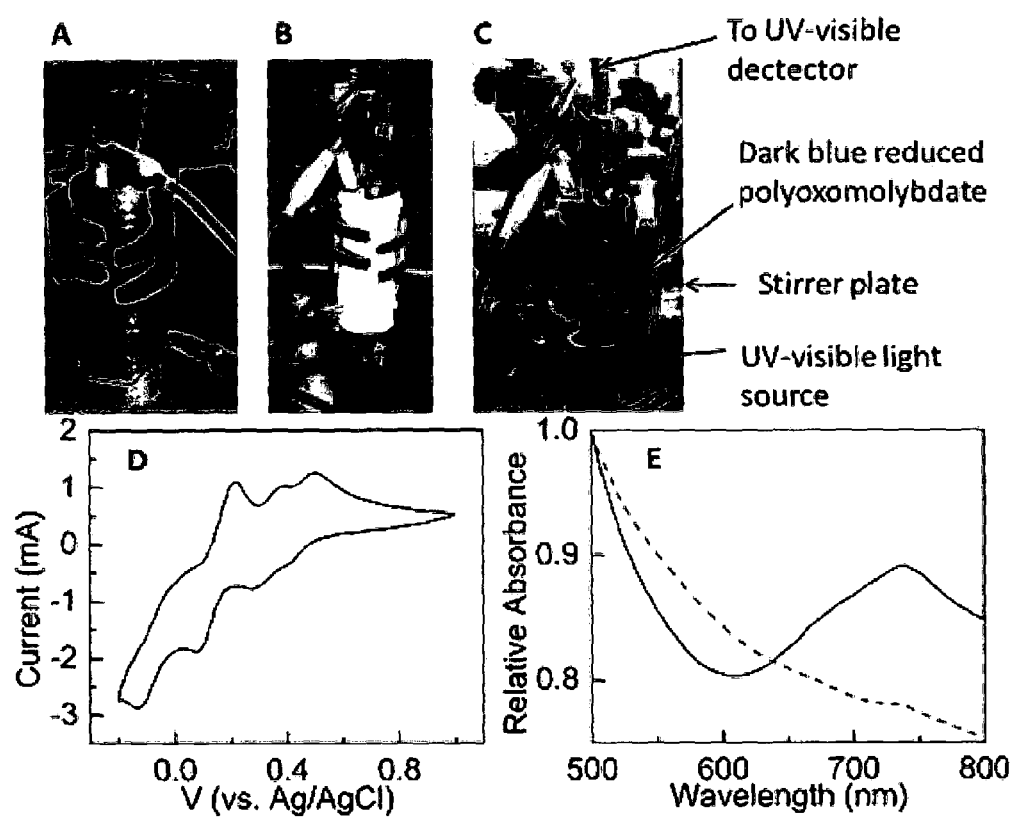
FIGS. 5 (A)-(C) are photographs of reactionware using in situ spectroscopies as part of an embodiment of a vessel of the invention, where (A) is a cell for electrochemistry in a three-electrode configuration; (B) and (C) show the reactionware used for spectroelectrochemistry.

By equipping the reaction vessel with a small stir-bar, the solution could be stirred magnetically (the stir-plate was held to the side of the cell, see FIG. 5C). Hence bulk electrolysis on the sample could be performed (the ITO working electrode was poised at −0.2 V vs. the reference electrode), leading to the entire solution turning dark blue within a few minutes. This colour change was clearly visible with the naked eye (see FIG. 5C). This study shows that 3D-printed reaction vessel is suitable for both spectroscopic analyses and bulk synthetic/electrosynthetic processes.

Figure 12:
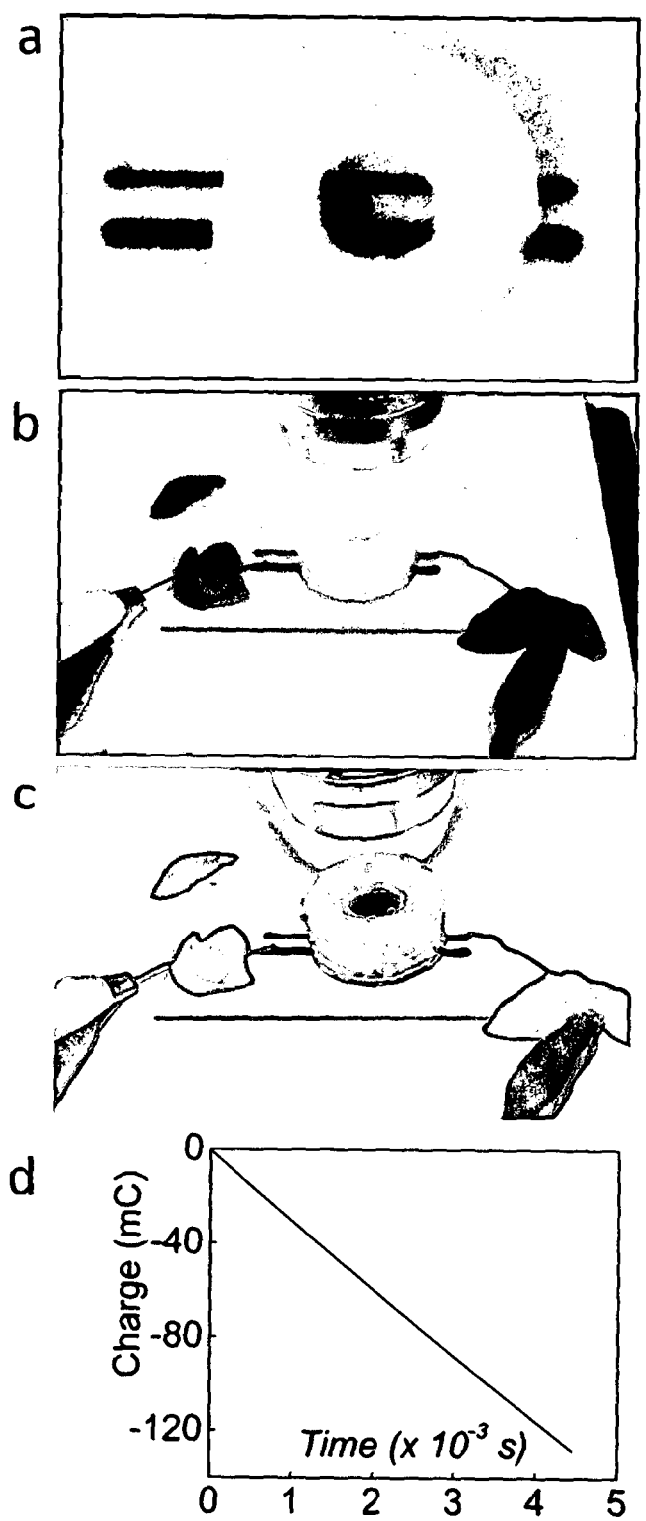
FIG. 12 (A) to (C) is a series of photographs showing a 3D-printed electrochemical cell and electrodes according to an embodiment of the invention, where.

In addition to utilizing traditional electrodes within a 3D-printed cell, it is also possible to 3D-print an entire electrochemical cells. To this end, an acetoxy-silicone polymer (before curing) was mixed with toluene to make a thinner gel. This gel was then mixed with conductive carbon black to produce a conductive paste suitable for loading into the 3D-printer (see FIG. 9). A basic vessel having an electrochemical cell was then printed, whereby two parallel lines of the conductive paste were printed onto a glass slide about 0.5 cm apart, with the remaining portion of the watertight cell housing formed from unmodified acetoxy-silicone bathroom sealant (see FIG. 12A). The glass slide was solely employed to aid visualization of the ensuing electrochemical reactions, and various functional architectures for electrochemical cells can be envisioned using solely printed components.

Figure 6:
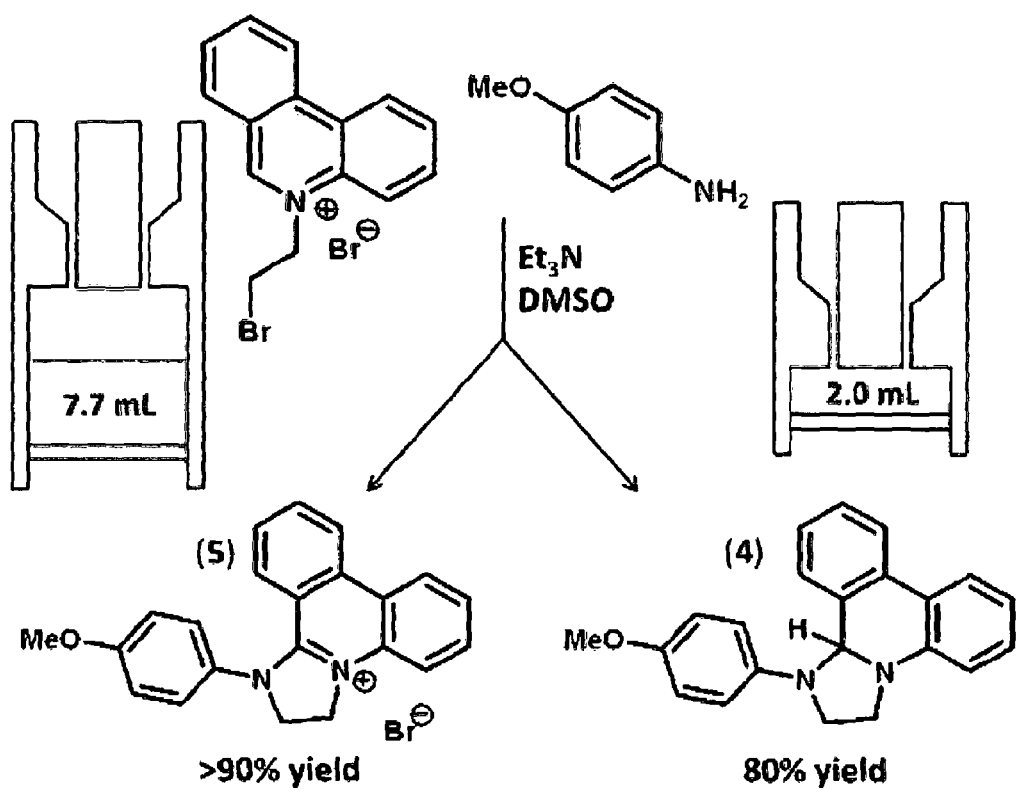
FIG. 6 is a schematic illustrating the different reaction outcomes recorded for the reaction of 4 and 5 as influenced by the reactor architecture.

The two electrodes of the cell were then connected to a three-electrode potentiostat as shown in FIGS. 6B and 6C: the working electrode was connected to one rail of conductive paste using a copper wire whilst the reference and counter electrodes were both attached to the other rail of conductive paste, giving a "floating" reference configuration. The vessel was then filled with a 5 mM aqueous solution of PMA in 0.1M $H_2SO_4$, and a voltage of −2.5 V applied to the working electrode rail. Within a few minutes, the yellow polyoxometalate solution had started to turn blue around the working electrode as it was reduced. The reaction was followed visually and coulombmetrically (see FIG. 12D): the observed linear relationship between charge and, time that indicates that the cell was capable of supplying a constant current over the course of the experiment (>1 hour). This indicates that there was no apparent degradation in the conductivity of the cell over this time period.

Vessel and Reaction Evolution

Given the vast number of possible materials that can be 3D-printed, for use as vessel material or for use as reagents for reactions held within the vessel, and the countless different architectures that can be created by robocast-3D-printing, the synergy between vessel geometry and the chemistry taking place inside could become an important new reaction parameter to be optimised and utilised in 3D-printed reactors. Accordingly reaction evolution was investigated using changes in vessel architecture.

A vessel architecture similar to that shown in FIG. 1C was assembled. The vessel was prepared with no frit; the volume of each of the two reservoirs was 4.7 mL and the volume of the reaction chamber was 7.7 mL (see FIG. 10 and "Reactor A" in FIG. 6). The reaction was performed with 1 equivalent of 4-methoxyaniline and 3 equivalents of 5-(2-bromoethyp-phenanthridinium bromide in $d_6$-DMSO, in the presence of excess $Et_3N$ (see Parenty et al. J. Org. Chem. 2004, 69, 5934-5946).

After reaction initiation, the product distribution was monitored by $^1H$ NMR, giving a conversion of 4-methoxyaniline starting material to heterocycle 5 of >90% after 21 hours. No heterocycle 4 was observed in this reaction mixture (Richmond et al. (Org. Chem. 2009, 74, 8196-8202). The reactor architecture was then changed ("Reactor B") so that the size of the combined mixing/reaction chamber was reduced to 2 mL, whilst keeping all other parameters constant (concentrations, solution volumes, etc.). This meant that only 1 mL of each solution could enter the reaction chamber. i.e. the reactor architecture enforced a 1:1 ratio of 4-methoxyaniline to 5-(2-bromoethyl)phenanthridinium bromide, with the residual 2 mL of the 5-(2-bromoethyl)phenanthridinium bromide solution remaining unreacted in the upper chamber (from which it could theoretically be siphoned off for other reactions). Using this reactor design, the ratio of 4 to 5 obtained after 21 hours was 80:20, indicating a complete reversal of selectivity by simply and solely altering the reactionware architecture. This simple example demonstrates how altered reactor geometry can be used to influence reactant stoichiometry and hence the outcome of a chemical reaction. Thus product identity and/or product quantity may be controlled with digitally designed and 3D-printed labware. Accordingly, 3-D printing technology may be used to optimize reaction conditions.

Crystallographic Data

Suitable single crystals were selected and mounted onto the end of a thin glass fibre using Fomblin oil. X-ray diffraction intensity data were measured at 150(2) K on an Oxford Diffraction Xcalibur Gemini Ultra diffractometer using MoKα radiation [λ=0.71073 Å] for compounds 1 and 3 or a Bruker Apex II diffractometer for compound 2. Structure solution and refinement were carried out with SHELXS-97 and SHELXL-97 via WinGX (see Sheldrick et al. *Acta Crystallogr.*, Sect. A 1998, A46, 467-473; Sheldrick *Acta Crystallogr.*, Sect. A 2008, A64, 112-122; Farrugia *J. Appl. Cryst.* 1999, 32, 837-838). Corrections for incident and diffracted beam absorption effects were applied using analytical[7] methods for compounds 1 and 3 and empirical methods for compound 2.

Crystal data for $(C_2H_8N)_7Na_4[W_{19}CO_2O_{61}Cl(SeO_3)_2(H_2O)_2]Cl_2 \cdot 6H_2O$ (1)

$M_r$=5506.03 g $mol^{-1}$; block crystal: 0.20×0.13×0.05 $mm^3$; T=150 (2) K. Monoclinic, space group C2/m, a=34.9972(18), b=20.8610(10), c=18.0161 (10) Å. β=108.602(3)°, V=12466.0 (11) $Å^3$, Z=4, ρ=2.934 $cm^{-3}$, μ(Mo—Kα)=18.448 $mm^{-1}$, F(000)=9712, 44468 reflections measured, of which 12155 are independent ($R_{int}$=0.0672), 669 refined parameters, $R_1$=0.0368 and $wR_2$=0.0779 (all data).

Crystal data for $(C_2H_8N)_8Na_3[W_{19}Mn_2O_{61}Cl(SeO_3)_2(H_2O)_2]C_2 \cdot 6H_2O$ (2)

$M_r$=5521.15 g $mol^{-1}$; block crystal: 0.12×0.12×0.10 $mm^3$; T=150(2) K. Monoclinic, space group C2/m, a=36.022(3), b=20.6218(13), c=17.8132 (13) Å. β=110.322 (5)°. V=12408.7(16) $Å^3$, Z=4, ρ=2.955 $cm^{-3}$, μ(Mo—Kα)= 18.467 $mm^{-1}$, F(000)=9760, 90225 reflections measured, of which 12561 are independent ($R_{int}$=0.0616), 582 refined parameters, $R_1$=0.0515 and $wR_2$=0.1713 (all data).

Crystal data for $C_2H_{17}BrN_2O$ (3)

$M_r$=393.28 g $mol^{-1}$; needle crystal: 0.16×0.10×0.08 $mm^3$; T=150(2) K. Monoclinic, space group P2(1)/n, a=9.0792(3), b=13.8548(4), c=13.5655 (4) Å. β=101.341 (3)°, V=1673.09(9) $Å^3$, Z=4, ρ=1.561 $cm^{-3}$, μ(Mo—Kα)= 2.468 $mm^{-1}$, F(000)=800, 8241 reflections measured, of which 3059 are independent ($R_{int}$=0.0438), 294 refined parameters, $R_1$=0.0316 and $wR_2$=0.0834 (all data).

Additional Experimental and Results

The following examples demonstrate the use of 3-D printing techniques to prepare and use a multi-chamber (multi-reaction space) reaction vessel in the preparation of a product compound. The chambers are in series and a plurality of the chambers are provided with reagents, specifically catalysts, that are printed onto the surfaces of the reaction vessel and are exposed to the chamber for interaction with the chamber contents.

Described below is a multi-step organic synthesis achieved in a 3D-printed reaction vessel which incorporates specific chemically active regions (in this case the montmorillonite K10 Lewis acid, which is known to catalyse Diels-Alder reactions, and a Pd/C reduction catalyst), which are components contained in the reaction vessel walls. These active regions may be printed during the reactor fabrication by a simultaneous 3D-printing process of both the vessel and catalysts.

To demonstrate the potential of 3D-printed reaction vessel, a multi-stage synthetic organic reaction sequence was performed, in which successive transformations were separated spatially by the design of the device. Two device designs were realised: one in which the reactor was open to the environment, allowing the introduction of reaction starting materials and reagents at various points in the process, and one in which all the necessary materials were introduced into the device during the fabrication process, producing a self-contained chemical reactor (see FIG. 13). The reaction sequence in each case proceeded in a controlled fashion and in the correct order upon rotation of the device, such that the products of one step only flowed into the next chamber for further reaction if the orientation of the device was correct.

The reaction system was made up of three different standard organic reactions performed in sequence. The reactions chosen represent classes of reactions which are used in a vast range of chemical syntheses: a Diels-Alder cyclization, followed by the formation of an imine and finally a hydrogenation step to the secondary amine using triethyl silane (TES) as an in situ hydrogen source. As such, the reactors were designed with three reaction chambers, one for each of the successive stages in the sequence (see FIG. 13). During the synthesis, the reaction mixture was transferred from chamber to chamber upon the completion of each reaction step simply by rotating the device and allowing gravity to pull the reaction mixture into the next chamber.

The device was designed in such a way that the solutions will only flow into the subsequent chamber upon rotation of the device. The first and third reactions in the synthetic sequence require catalysts for effective completion of the reactions. These catalysts were introduced into the reaction vessel walls during the printing of the reaction vessel device, resulting in a functional reactor which was specific to this reaction sequence.

The fabrication of the device is described in detail below.

The reactions exemplified here show that a bespoke-designed reactor vessel can be fabricated for a specific reaction sequence using 3D-printing technology, and this vessel may be used to perform a multi-step synthetic procedure. By "sealing-in" the reagents and catalysts necessary for these transformations, the present inventor was able to obtain the same products as could be obtained using standard glassware, but without having to handle any chemicals or specialist equipment during the synthesis itself.

The present work demonstrates the compatibility of relatively low cost 3D-printing technologies with synthetic organic chemistry, and it points towards applications where chemistry can be performed in 3D-printed devices in places where there is no laboratory apparatus and by people who have no detailed knowledge of liquid handling in chemistry.

Figure 13:
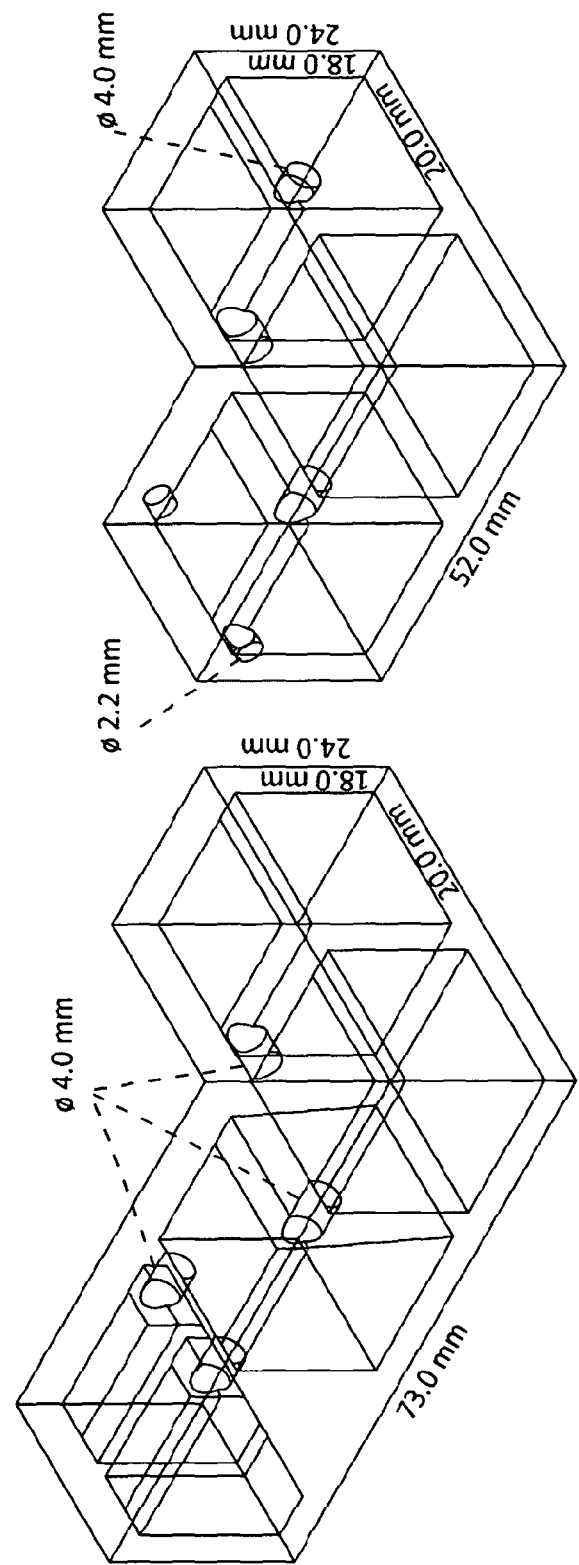
FIG. 13 shows two reaction vessel designs according to certain embodiments of the invention, where each reaction vessel has a plurality of reaction chambers that are in fluid communication. The reaction chambers are in series. The left-hand reaction vessel is a sealed unit, where the first reaction chamber is in fluid communication with a plurality of reservoirs, which are also sealed in. The right-hand reaction vessel is an unsealed unit, where the first reaction chamber has inlets that allow material to be added to chamber from outside the vessel, and the third reaction chamber has an outlet that allows material to exit the reaction vessel.

The present inventor has also found that a reaction vessel having multiple reaction spaces may incorporate a purification zone, for the purification of the final product synthesised in the third reaction chamber of the devices of FIG. 13. The device of FIG. 18 has a silica plug contained within a fourth reaction space (which is the purification zone) provided downstream of the third reaction space. The third and fourth reaction vessels may in fluid communication. However, the inventor has found that the purification of the product from the third reaction chamber is simplified if the fluid communication is made only once the reaction in the third chamber is deemed complete. A seal may be provided between the third reaction space and the purification zone, and this seal may be pierced at an appropriate time to allow material to move from the third reaction space into the purification zone. The seal may simply be an internal wall of the reaction vessel which may be pierced by e.g. a syringe needle.

Figure 18:
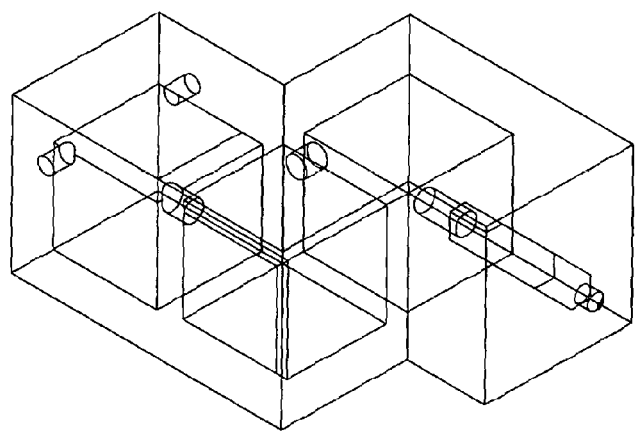
FIG. 18 is a reaction vessel design according an embodiment of the invention, which based on the reaction vessel of FIG. 13 (right). The reaction vessel of FIG. 18 incorporates a fourth reaction space that is downstream of the third reaction space. The fourth reaction space is a provided with a plug of material, such as silica, for purifying the outflow from the third reaction space.

The device of FIG. 18 is prepared in the same manner as the device of FIG. 13 (right) with appropriate changes to the printing schedule to accommodate a fourth reaction chamber, and appropriate timetabling of the printing sequence to accommodate delivery of the purification material, in this case silica with cotton wool plugs to contain the material, into the reaction vessel.

General Experimental

All chemical reagents and solvents were purchased from Sigma Aldrich and used without further purification except for 1,2,3,4,5-pentamethylcyclopentadiene (94%), (Alfa Aesar) and the acetoxy-silicone polymer (LOCTITE® 5366 bathroom sealant, Loctite Corp.). Pd/C (10% b/w) was supplied by Lancaster. 3D printing was achieved on a Bits from Bytes (BfB) 3DTouch™ 3 extruder 3D printer supplied by Bits from Bytes, and a Fab@Home Version 0.24 RC6 freeform fabricator assembled from a kit by the authors. Labware was designed digitally using Autodesk123D free CAD software distributed by Autodesk Inc. (http://www.123dapp.com/) and uploaded to the freeform fabricator for printing. $^1$H NMR and crude $^{13}$C NMR spectra were recorded on a Bruker Avance 400 MHz machine at 298 K, and chemical shifts are reported in ppm relative to residual solvent (multiplicities are given as s: singlet, d: doublet, t: triplet, q: quartet, m: multiplet, with coupling constants reported in Hz). Final product $^{13}$C and two dimensional NMR spectra were recorded on a Bruker Avance III 500 MHz machine at 298K. Mass spectra were obtained using a Q-trap, time-of-flight MS (MicroTOF-Q MS) instrument equipped with an electrospray (ESI) source supplied by Bruker Daltonics Ltd. All analysis was carried out in MeOH, collected in positive ion mode, unless otherwise stated. The spectrometer was calibrated with the standard tune-mix to give a precision of ca. 1.5 ppm in the region of m/z 100-3000.

Design Software

The 3D-printed reactionware used in this work was designed on the freely distributed 3D CAD software Autodesk123D (http://www.123dapp.com/). Other 3D modelling/CAD software with the ability to export models in a .STL file format may be used.

General Reactor Design

The reactor design in this example incorporates three reaction chambers, one for each of the successive steps in a planned reaction sequence. The device design included the printing of active Lewis acid montmorillonite K10 and Pd/C catalysts in specially prepared 'ink' materials suitable for introduction into the reactor during the fabrication process by a 3D printing device. These catalytically active areas were present in the first (montmorillonite K10 Lewis acidic clay) and third (Pd/C 10%) reaction chambers of the designed device. The chambers were designed such that reactant transfer from chamber to chamber could be achieved by rotation of the reactor to allow the reaction mixture to flow from one chamber to another under gravity. To allow fluid communication between chambers, 4.0 mm internal channels were provided between chambers, and these channels were positioned so that through any of the envisioned 90° rotations of the device, the reaction mixture would flow through only one of the available channels thereby allowing the reaction mixture to be controllably maneuvered between the reaction chambers. The device design was achieved in two parts: one part representing the main architecture of the reactor, and a second part containing the regions into which the catalytically active inks were to be incorporated into the fabricated device.

Open and Sealed Reactor Design

Two different reaction vessels were prepared: an open reactor into which reactants and reagents could be introduced during the course of the synthetic procedure, and a sealed vessel into which all the necessary reactants and reagents must be introduced during the fabrication of the vessel itself: thus providing a self-contained reactor. Whilst the key features of the two devices (i.e. the three reaction chambers for the three stages of the synthetic sequence) remained the same, the different intended purpose required two different architectures to be designed.

The open reaction vessel required the presence of apertures in the first chamber through which the initial starting materials could be provided into the internal space of the vessel. The first chamber was designed with two apertures on either side of the chamber through which reagents could be introduced. The final chamber was provided with an aperture through which the final reaction mixture could be collected by a final 90° rotation of the device.

The sealed reaction vessel design called for chambers into which all the starting materials and subsequent reagents and solvents could be deposited during the printing process. It was necessary for these reagents to be kept separate until the reaction was initiated by the user. To achieve this, a section of the device was created to house two reactant chambers (reservoirs), oriented such that a rotation of 45° would induce the two reactant solutions contained within to flow together into the initial reaction chamber.

Figure 14:
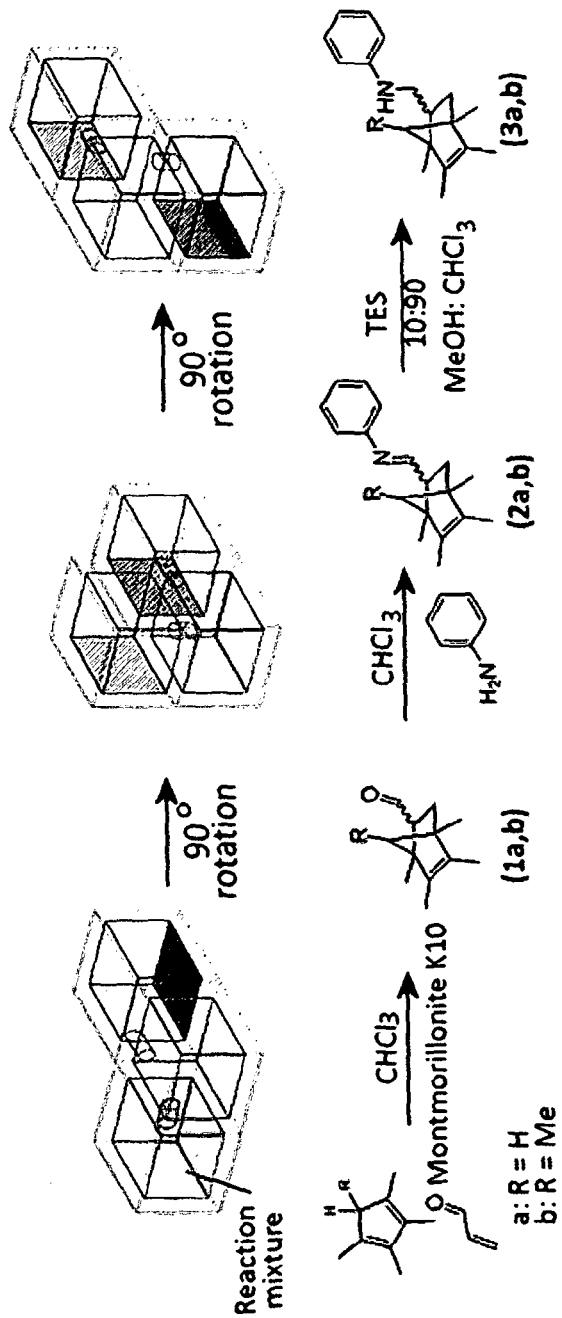
FIG. 14 is a schematic of a multi-step reaction sequence in both open and sealed reaction vessels, once the sequence has been initiated by mixing the starting materials. Only the main (reaction) chambers are shown for clarity. The reagents can be induced to flow into subsequent reaction chambers by rotation of the device through 90° intervals (as shown).

The reactor designs are shown in FIGS. 13 and 14.

Device Fabrication

Both device design parts were exported from the design software as .STL files. The main architecture component .STL file was then interpreted by Bits from Bytes Axon 2 software which produces a 3D printer instruction file (.bfb file) which was subsequently transferred to the 3DTouch™ 3D printer. The catalyst area of the reaction vessel was provided as .STL file that was interpreted by Fab@Home software and transmitted to a Fab@Home Version 0.24 RC6 freeform fabricator.

The main device architecture was printed using commercially available polypropylene in the form of 3 mm diameter welding rod which was automatically fed into the 3DTouch™ machine. The polypropylene was suitably inert to the reagents, solvents and conditions used in the experiments described herein.

After printing, the reactor was allowed to rest at room temperature for 12 hours to allow the complete curing of the silicone polymer mixture (see below) and the reactionware was repeatedly washed with distilled water until all traces of acetic acid (released during curing of the catalyst containing inks) had been removed. The reactor was subsequently dried under vacuum for 18 h. No serious adverse effects from acetic acid seepage into solution (which would lower the solution pH) was observed during the subsequent reactions.

The printing was conducted in a layer-by-layer fashion by the 3DTouch™ printer with pre-programmed pauses in the printing process to allow the printing of the catalytically active regions by the Fab@Home device. During the pauses the partially printed device was transferred from the 3DTouch™ machine to the Fab@Home device, where the catalyst regions were deposited from 10 mL syringes via a tapered dispensing tip with an internal diameter of 0.838 mm.

Catalytic materials for printing were prepared by first thinning silicone polymer with toluene (30% by mass) followed by the addition of the appropriate active material. The Pd/C reduction catalyst ink was prepared from 0.5 g Pd/C (10% Pd w/w) with 6 g of a silicone/toluene mixture. The montmorillonite K10 Lewis acid catalyst was prepared from 0.5 g montmorillonite K10 powder with 6 g of a silicone/toluene mixture. These mixtures gave pastes of sufficient viscosity to print in a similar manner to the original silicone polymer. The Fab@Home 3D printer utilized in this work was configured with two syringe tools which were filled with the appropriate printing materials, allowing the printer to deposit two materials without changing the device configuration. The printed (pre-curing) mass of catalyst-containing material is given in the table below.

Mass of Catalyst Printed into Reaction Chambers of 3D Printed Reaction Vessel

| Catalyst | Printed Mass (g) | Catalyst Mass (g) |
| --- | --- | --- |
| Montmorillonite K10 | 0.419 | 0.035 |
| 10% Pd/C | 0.230 | 0.019 |

Once printing of the catalytic regions was complete, a small magnetic stirrer bar was placed in each of the three reaction chambers and the partially printed device was returned to the 3DTouch™ printer (aligned to the original reaction vessel printing position) and printing of the reactor architecture was resumed. During the printing of the sealed device, the printing was resumed after 24 hours to give the catalyst regions sufficient time to cure before the addition of reagents, and paused once again towards the end of the print program to allow the introduction of starting materials and other reagents into their appropriate chambers.

The printed devices conformed to the CAD design dimensions with less than 5% difference in any dimension, indicating a high degree of accuracy in the printing process.

General Procedure for Sequential Synthesis in the 3D Printed Reactor

Open Reactor

Solutions of acrolein (1 mmol, 66 mg, 47 µL) and either 1,2,3,4-tetramethyl-1,3-cyclopentadiene (1 mmol, 122 mg, 99 µL) or 1,2,3,4,5-pentamethylcyclopentadiene (1 mmol, 136 mg, 118 µL) in chloroform (1 mL each) were simultaneously injected into a 3D printed multi chamber vessel via the apertures (inlet ports) provided in the first reactor chamber.

The reaction mixture was stirred in the first chamber (in contact with the montmorillonite K10 Lewis acid catalyst region) for 5 hours. The reactor was then rotated through 90° to allow the reaction mixture from the first chamber to flow into the second reaction chamber. In order to ensure maximum transference of reaction mixture into the second reaction chamber, the reactor was returned to its original orientation and a small aliquot of chloroform (0.5 mL) was added to the first chamber via the inlet ports, where it was briefly stirred before being transferred into the second chamber.

Once the reaction vessel was in its second orientation a solution of aniline (1 mmol, 93 mg, 95.1 µL) in chloroform (1 mL) was injected into the reactor through one of the inlet ports and was allowed to flow directly into the second reaction chamber via the first chamber. The reaction was then allowed to stir for a further 2 hours to allow complete imine formation.

A mixture of triethyl silane (TES, 10 mmol, 1.16 g, 844 μL) and methanol (0.875 mL) was then introduced via one of the initial inlet ports and allowed to flow directly into the second reaction chamber, where it mixed with the reaction mixture. This solution was then transferred to the third reaction chamber by a further 90° rotation of the vessel.

Upon contact of the reaction mixture with the Pd/C in silicone catalyst, hydrogen gas was evolved. The reaction mixture was stirred in the final reaction chamber for 20 min. before the reaction mixture was decanted by another 90° rotation of the reactor, which allowed the reaction mixture to flow out of the outlet port designed into the third chamber. The third reaction chamber was washed with choloroform (3×2 mL) and the collected washings were combined with the final reaction mixture.

The solvent was than removed under vacuum and the crude product was purified by silica gel chromatography, eluting with 10% EtOAc-Hexane to give the product as a mixture of structural isomers.

Sealed Reactor

During the reactor fabrication process solutions of acrolein (1 mmol, 56 mg, 47 μL) and either 1,2,3,4-tetramethyl-1,3-cyclopentadiene (1 mmol, 122 mg, 99 μL) or 1,2,3,4,5-pentamethylcyclopentadiene (1 mmol, 136 mg, 118 μL) in chloroform (1 mL each) were introduced into the starting material chambers of the sealed device and a mixture of the reagents necessary for the second and third reactions in the sequence, i.e. a solution of aniline (1 mmol) in a mixture of TES (10 mmol) and MeOH (0.875 mL), were added into the second reaction chamber.

The reaction sequence is initiated by the rotation of the reactor by 45° to induce the starting material solutions to flow into the initial reaction chamber. Thereafter a similar set of rotations to those described above are performed on the sealed reactor device to affect the desired reaction sequence. Upon completion of the process the reaction mixture is retrieved by pushing a needle through the wall of the final reaction chamber and drawing the contents out with a syringe. The same syringe was then used to wash the final reaction chamber with chloroform (3×2 mL) and collect the washings, which were combined with the final reaction mixture.

The solvent was then removed under vacuum and the crude product was purified by silica gel chromatography, eluting with 10% EtOAc-Hexane to give the product as a mixture of structural isomers.

Traditional (Glassware) Procedure for Sequential Synthesis

To a stirred solution of and either 1,2,3,4-tetramethyl-1,3-cyclopentadiene (1 mmol, 122 mg, 99 μL) or 1,2,3,4,5-pentamethylcyclopentadiene (1 mmol, 136 mg, 118 μL) in chloroform (1 mL) was added montmorillonite K10 (30 mg) followed by a solution of acrolein (1 mmol, 56 mg, 47 μL) in chloroform (1 mL). The reaction mixture was allowed to stir at room temperature for 5 hours. The reaction mixture was then filtered to remove the montmorillonite catalyst and the reaction mixture transferred to a new round bottomed flask, into which was added solution of aniline (1 mmol, 93 mg, 95.1 μL) in chloroform (1 mL). The reaction mixture was then stirred for a further 2 hours to allow complete imine formation. To the stirred reaction mixture was then added 10% Pd/C (20 mg) followed by the addition of a mixture of triethyl silane (TES, 10 mmol, 1.16 g, 844 μL) and methanol (0.875 mL). The reaction mixture was then stirred for 20 minutes, and the resulting reaction mixture filtered to remove the Pd/C catalyst. The solvent was then removed under vacuum and the crude product was purified by silica gel chromatography, eluting with 10% EtOAc-Hexane to give the product as a mixture of structural isomers (3a, yield: 102.8 mg 40.0% based on original starting materials; 3b, yield 105.5 mg 38.9% based on original starting materials).

NMR Comparison Between Glassware and Printed Reaction Vessel

In order to ascertain the suitability of 3D-printed reactors for carrying out synthetically useful transformations it was necessary to compare the results of each stage in the reaction sequence with the corresponding stage in the traditionally carried out reaction procedure (i.e. carried out in traditional glassware). The sequential reaction was followed by $^1$H NMR in a series of experiments carried out in accordance with the above general procedures in deuterated solvents where the reaction mixture at each stage of the synthesis was extracted from the reactor by pushing a needle through the side of the device and removing the contents.

1,4,5,6-Tetramethyl-bicyclo[2.2.1]hept-5-ene-2-carbaldehyde (1a)

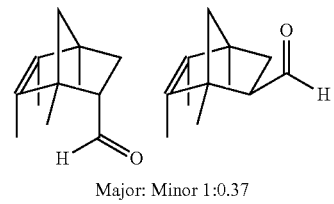

Major: Minor 1:0.37

$^1$H NMR (CDCl$_3$, 400 MHz): (Major product): δ9.15 (d, 1H, J=4.2 Hz), 2.57 (dt, 1H, J$_1$=8.8 Hz, J$_2$=4.2 Hz), 1.60-1.65 (m, 2H), 1.53 (s, 3H), 1.45 (s, 3H), 1.37-1.41 (m, 2H), 1.25 (s, 3H), 1.16 (s, 3H). (Minor product): δ 9.58 (d, H, J=5.0 Hz), 1.99-2.03 (m, 1H), 1.69-1.73 (m, 2H), 1.49 (s, 3H), 1.48 (s, 3H), 1.33-1.39 (m, 2H), 1.19 (s, 3H), 1.13 (s, 3H). $^{13}$C NMR (CDCl$_3$, 100 MHz): (Major+Minor products): δ 8.9 (CH$_3$), 9.3 (CH$_3$), 9.6 (CH$_3$), 11.2 (CH$_3$), 15.4 (CH$_3$), 16.7 (CH$_3$), 17.0 (CH$_3$), 17.2 (CH$_3$), 25.9 (CH$_2$), 30.7 (CH$_2$), 36.2 (C$_q$), 37.5 (C$_q$), 50.9 (CH), 55.4 (CH$_2$), 55.8 (CH), 60.8 (C$_q$), 61.1 (CH$_2$), 61.2 (C$_q$), 134.4 (C=C), 137.5 (C=C), 138.4 (C=C), 140.3 (C=C), 205.5 (C-aldehyde), 205.7 (C-aldehyde).

Phenyl-(1,4,5,6-tetramethyl-bicyclo[2.2.1]hept-5-en-2-ylmethylene)-amine (2a)

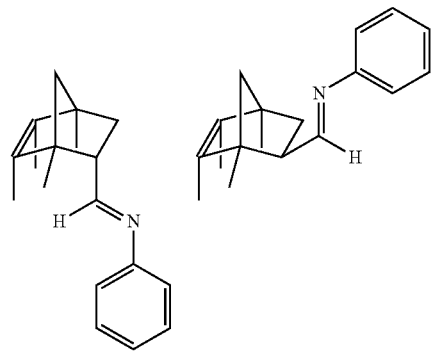

Major: Minor 1:0.37

¹H NMR (CDCl₃, 400 MHz): (Major product): δ 7.39-7.26 (m, 5H), 6.99 (d, 1H, J=7.9 Hz), 2.69-2.64 (m, 1H), 2.91-2.86 (m, 4H), 1.61 (s, 3H), 1.59 (s, 3H), 1.32 (s, 3H), 1.28 (s, 3H). (Minor product): δ 7.77 (d, 1H, J=7.8 Hz), 7.39-7.26 (m, 5H), 2.55-2.50 (m, 1H), 2.91-2.86 (m, 4H), 1.64 (s, 3H), 1.56 (s, 31-1), 1.26 (s, 3H), 1.21 (s, 3H). ¹³C NMR (CDCl₃, 100 MHz): (Major+Minor product) δ 9.2 (CH₃), 9.9 (CH₃), 11.5 (CH₃), 12.5 (CH₃), 16.2 (CH₃), 17.0 (CH₃), 17.1 (CH₃), 17.9 (CH₃), 39.7 (CH₂), 40.8 (CH₂), 50.7 (CH), 50.9 ($C_q$), 51.9 ($C_q$), 52.6 ($C_q$), 55.5 ($C_q$), 55.6 (CH), 56.3 (CH₂), 60.7 (CH₂), 114.7 (C=C), 115.8 (C=C), 118.4 (C=C), 119.0 (C=C), 120.6 (CH—Ar), 120.8 (CH—Ar), 125.3 (CH—Ar), 125.4 (CH—Ar), 129.5 (CH—Ar), 129.7 (CH—Ar), 139.5 (CH—Ar), 134.9 (CH—Ar), 140.4 (CH—Ar), 140.6 (CH—Ar), 152.3 ($C_q$—Ar), 152.4 ($C_q$—Ar), 170.6 (C-Imine), 170.8 (C-Imine).

1,4,5,6,7-Pentamethyl-bicyclo[2.2.1]hept-5-ene-2-carbaldehyde (1b)

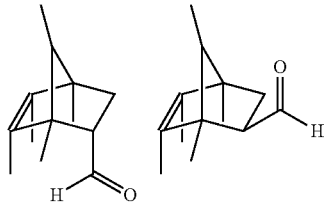

Major: Minor 1:0.2

¹H NMR (CDCl₃, 400 MHz): (Major product): δ9.17 (d, 1H, J=4.2 Hz), 2.45 (dt, 1H, J₁=4.2 Hz, J₂=8.6 Hz), 1.56 (d, 2H, J=8.6 Hz), 1.48 (s, 3H), 1.41 (s, 3H), 1.28 (q, 1H, J=6.4 Hz), 1.11 (s, 3H), 1.02 (s, 3H), 0.50 (d, 3H, J=6.4 Hz); (Minor product): δ 9.63 (d, 1H, J=4.6 Hz), 2.45 (dt, 1H, J₁=4.6 Hz, J₂=8.9 Hz), 1.58 (d, 2H, J=8.9 Hz), 1.44 (s, 3H), 1.43 (s, 3H), 1.29 (q, 1H, J=6.5 Hz), 1.11 (s, 3H), 1.05 (s, 3H), 0.53 (d, 3H, J=6.5 Hz). ¹³C NMR (CDCl₃, 100 MHz): (Major+Minor product) δ7.2 (CH₃), 7.9 (CH₃), 9.4 (CH₃), 9.9 (CH₃), 10.1 (CH₃), 11.7 (CH₃), 13.5 (CH₃), 14.1 (CH₃), 14.7 (CH₃), 15.1 (CH₃), 36.3 (CH₂), 37.4 (CH₂), 52.7 (CH), 56.3 ($C_q$), 56.9 ($C_q$), 58.6 (CH), 61.0 (CH), 61.7 ($C_q$), 61.9 ($C_q$), 62.2 (CH), 130.7 (C=C), 134.8 (C=C), 136.6 (C=C), 137.3 (C=C), 206.3 (C-aldehyde), 206.5 (C-aldehyde).

(1,4,5,6,7-Pentamethyl-bicyclo[2.2.1]hept-5-en-2-ylmethylene)-phenyl-amine (2b)

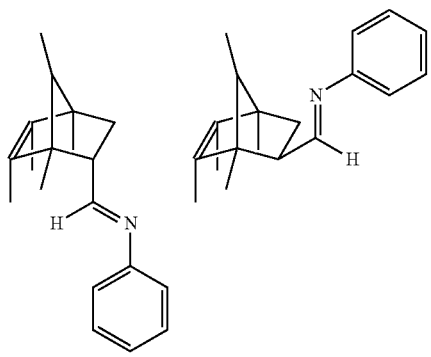

Major: Minor 1:0.2

¹H NMR (CDCl₃. 400 MHz): (Major product): δ 7.83-7.28 (m, 5H), 7.00 (d, 1H, J=8.0 Hz), 2.65 (dt, 1H, J₁=8.0 Hz, J₂=8.7 Hz), 1.76 (d, 2H, J=8.7 Hz), 1.56 (s, 3H), 1.28 (s, 3H), 1.44 (q, 1H, J=6.5 Hz), 1.18 (s, 3H), 1.12 (s, 3H), 0.63 (d, 3H, J=6.5 Hz). (Minor product): δ 7.81 (d, 1H, J=8.0 Hz), 7.83-7.28 (m, 5H, Ar), 2.29 (q, 1H, J=6.26 Hz), 2.22-2.15 (m, 1H), 1.79 (d, 2H, J=8.3 Hz), 1.59 (s, 3H), 1.55 (s, 3H), 1.14 (s, 3H), 1.09 (s, 3H), 0.65 (d, 3H, J=6.3 Hz); ¹³C NMR (CDCl₃, 100 MHz): (Major product) δ 7.8 (CH₃), 7.9 (CH₃), 8.0 (CH₃), 8.1 (CH₃), 9.5 (CH₃), 9.7 (CH₃), 14.9 (CH₂), 15.4 (CHA 40.55 (CH₃), 44.2 (CH₃), 53.4 (CH), 53.6 (CH₃), 55.1 (CH₃), 58.4 (CH), 57.1 (CH), 58.9 (CH), 61.1 ($C_q$), 61.4 ($C_q$), 61.8 ($C_q$), 62.1 ($C_q$), 114.5 (C=C), 114.7 (C=C), 115.7 (C=C), 115.8 (C=C), 120.4 (CH—Ar), 120.5 (CH—Ar), 120.7 (CH—Ar), 120.9 (CH—Ar), 125.3 (CH—Ar), δ125.4 (CH—Ar), 129.5 (CH—Ar), 129.7 (CH—Ar), 135.2 (CH—Ar), 136.5 (CH—Ar), 152.3 ($C_q$—Ar), 152.4 ($C_q$-AO, 170.7 (C-Imine), 170.8 (C-Imine).

Phenyl-(1,4,5,6-tetramethyl-bicyclo[2.2.1]hept-2-ylmethyl)-amine (3a)

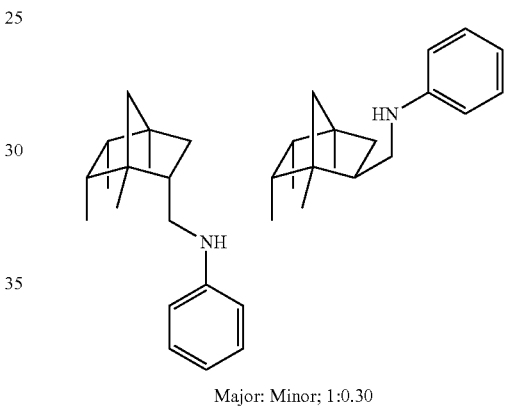

Major: Minor; 1:0.30

¹H NMR (CDCl₃, 400 MHz): (Major product): δ 7.19-7.16 (m, 2H) 6.71 (tt, 1H, J₁=7.2 Hz J₂=1.0 Hz), 6.56 (dt, 2H, J₁=8.5 Hz J₂=1.0 Hz), 3.4 (broad s, 1H), 3.14 (dd, 1H, J₁=11.0 Hz J₂=4.6 Hz), 2.44 (dd, 1H, J₁=11.0 Hz J₂=9.9 Hz), 2.22-2.15 (m, 1H), 1.79 (m, 1H), δ 1.64 (d, 3H, J=1.0 Hz), 1.60 (d, 3H, J=1.0), 1.31 (s, 3H), 1.23-1.21 (m, 2H), 1.19 (s, 3H), 1.18-1.16 (m, 1H), 1.09-1.04 (m, 1H), 0.87-0.83 (m, 1H). (Minor product): δ 7.21-7.19 (m, 2H) 6.72 (tt, 1H, J₁=7.3 Hz J₂=1.1 Hz), 6.64 (dt, 2H, J₁=8.6 Hz J₂=1.0 Hz), 3.32 (dd, 1H, J₁=11.0 Hz J₂=5.0 Hz), 2.90 (dd, 1H, J₁=11.1 Hz J₂=10.1 Hz), 1.75-1.70 (m, 1H), 1.61-1.60 (m, 3H), 1.63-1.58 (m, 3H), 1.56 (s, 3H), 1.52-1.47 (m, 1H), 1.46-1.45 (m, 1H), 1.38-1.35 (m, 1H), 1.26-1.24 (m, 1H), 1.20 (s, 3H), 1.15-1.13 (m, 1H), 0.95-0.90 (m, 1H); ¹³C NMR (CDCl₃, 100 MHz): (Major product) δ9.2 (CH₃), 11.9 (CH₃), 16.6 (CH₃), 17.7 (CH₃), 40.5 (CH₂), 42.3 (CH), 47.4 (CH₂), 48.9 (CH), 49.7 ($C_q$), 53.1 ($C_q$), 61.3 (CH₂), 61.6 (CH), 112.6 (CH—Ar), 117.0 (CH—Ar), 129.1 (CH—Ar), 135.2 ($C_q$—Ar). (Minor product) δ 9.0 (CH₃), 9.4 (CH₃), 15.0 (CH₃), 17.7 (CH₃), 42.2 (CH₂), 44.8 (CH), 48.1 (CH₂), 49.9 ($C_q$), 52.5 ($C_q$), 55.3 (CH₂), 55.7 (CH), 64.6 (CH), 112.7 (CH—Ar), 117.1 (CH—Ar), 129.2 (CH—Ar), 135.7 ($C_q$—Ar). HMRS (MH+) calcd. for C₁₈H₂₈N: 258.2216. found: 258.2240. Isolated yield: Open reactor: 96.2 mg (37.4%, based on original starting materials), Sealed Reactor: 82.0 mg (31.9%, based on original starting materials).

(1,4,5,6,7-Pentamethyl-bicyclo[2.2.1]hept-2-ylm-ethyl)-phenyl-amine (3b)

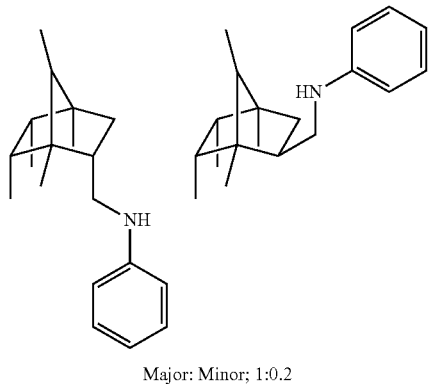 [SMILES: CC1C(C)C2(C)C(CNc3ccccc3)CC1(C)C2C ; CC1C(C)C2(C)C(CNc3ccccc3)CC1(C)C2C]

Major: Minor; 1:0.2

$^1$H NMR (CDCl$_3$, 400 MHz): (Major product) δ 7.10-7.06 (m, 2H), 6.59 (tt, 1H, J$_1$=7.3, J$_2$=1.0 Hz), 6.48 (dt, 2H, J$_1$=8.6, J$_2$=1.0 Hz), 3.4 (broad s, 1H), 3.05 (dd, 1H, J$_1$=11.0, J$_2$=4.6 Hz), 2.38-2.34 (m, 1H), 1.99-1.94 (m, 1H), 1.63-1.58 (m, 1H), 1.56-1.51 (m, 1H), 1.48 (d, 3H, J=1.0 Hz), 1.44 (d, 3H, J=1.2 Hz), 1.43-1.40 (m, 1H), 1.24 (q, 1H, J=6.4 Hz) 1.05 (s, 3H), 0.98-0.93 (m, 1H), 0.94 (s, 3H), 0.50 (d, 3H, J=6.4 Hz). (Minor product) δ7.11-7.08 (m, 2H), 6.60 (dt, 1H, J$_1$=7.3, J$_2$=1.1 Hz), 6.52 (dt, 2H, J$_1$=8.6, J$_2$=1.1 Hz), 3.20 (dd, 1H, J$_1$=11.3, J$_2$=5.0 Hz), 3.01 (dd, 1H, J=11.1, J$_2$=4.1), 2.83-2.78 (m, 1H), 2.41-2.36 (m, 1H), 1.77-1.73 (m, 1H), 1.48-1.47 (m, 3H), 1.43-1.44 (m, 3H), 1.39-1.37 (m, 1H), 1.21-1.18 (m, 1H), 1.06 (s, 3H), 0.96 (s, 3H), 0.68-0.64 (m, 1H), 0.52 (d, 3H, J=4.5); $^{13}$C NMR (CDCl$_3$, 125 MHz): (Major product) δ7.9 (CH$_3$), 9.6, (CH$_3$), 9.7 (CH), 12.2 (CH$_3$), 14.8 (CH), 14.3 (CH$_3$), 15.4 (CH$_3$), 40.6 (CH$_2$), 47.1 (CH$_2$), 48.6 (CH), 52.5 (C$_q$), 55.9 (C$_q$), 61.8 (CH), 112.7 (CH—Ar), 117.0 (CH—Ar) 129.1 (CH—Ar), 134.9 (C$_q$—Ar). (Minor product) δ8.0 (CH$_3$), 9.3 (CH$_3$), 9.4 (CH), 12.04 (CH), 12.8 (CH$_3$), 13.8 (CH$_3$), 15.3 (CH$_3$), 42.1 (CH$_2$), 45.6 (CH), 47.6 (CH$_2$), 52.6 (C$_q$), 55.2 (C$_q$), 61.7 (CH), 112.8 (CH—Ar), 117.1 (CH—Ar), 129.1 (CH—Ar), 135.3 (C$_q$—Ar). HMRS (MH+) calcd. for C$_{19}$H$_{29}$N: 272.2373. found: 272.2399. Isolated yield: Open Reactor: 85.0 mg (31.3%, based on original starting materials), Sealed Reactor: 75.6 mg (27.9%, based on original starting materials).

Multi-Component Reaction Vessels

The methods of the invention may be used to prepare multicomponent reaction vessel. The reaction vessels comprise a plurality of reaction spaces, and these reaction spaces are in fluid communication. As described herein, the components of the multicomponent reaction vessel may be separate, with each component having a reaction space. The fluid communication between the reaction spaces (and between the components) may be provided by components that are not prepared by 3D printing techniques.

Described below is a method of preparing organic compounds, using flow techniques with an in-line ATR-IR flow cell to monitor the reactions in real-time. An in-house designed and 3D-printed reaction vessel was employed for the synthesis of imines from a combination of aldehyde and primary amine reagents. Once the reaction conditions were optimized, a second 3D-printed reaction vessel was connected in series to conduct a reductive amination of the imines. The integration of the 3D-printed flow reactor was very easy and convenient due to the simplicity of designing and building the device employing 3D printing techniques, with the connection of the reactors to the system also being effortless. This represents a very attractive way to build new continuous-flow rigs for organic synthesis.

Reaction Vessel Set-Up

Figure 15:
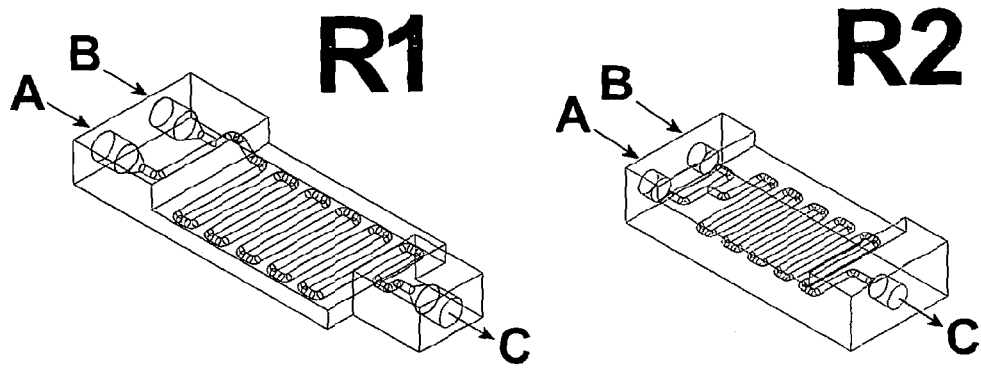
FIG. 15 is a schematic representation of two 3D-printed reaction vessels according to certain embodiments of the invention. Both vessels have two inputs (A and B) and one output (C). The main difference between the reaction vessels is the length of the inlets/outlets: in R2 the dimension of the inlets/outlet is modified for use together with check-valves.

The 3D-printed devices used to carry out the organic syntheses were designed using 3D Computer Aided Design (CAD) software package (Autodesk123D®). This 3D printer heats a PP thermopolymer through the extruder, depositing the material in a layer by layer fashion, converting the design into the desired 3D reactionware. Each device has two inlets, followed by a mixing point, a length of reaction space to ensure a controlled residence time and one outlet (see FIG. 15). The approximate volume of the first reactor (R1, see FIG. 15, left) is ca. 0.4 mL and was employed in the imine synthesis, while the second reactor (R2, FIG. 15, right) had a volume of ca. 0.35 mL and was employed connected to another R2 for the reductive amination process.

| Entry | Characteristics | R1 | R2 |
|---|---|---|---|
| 1 | Printing time (min) | 248 | 367 |
| 2 | PP mass (g) | 24.01 | 33.74 |
| 3 | Dimensions (mm) | 30 × 80.2 × 10 | 70 × 30 × 15 |
| 4 | Internal diameter (mm) | 1.5 | 1.5 |
| 5 | Theoretical volume* (mL) | 0.54 | 0.51 |
| 6 | Reactor volume | 0.4 | 0.35 |

*The theoretical internal volumes of the devices are lower than the measured volumes. This is due to the printing-process, where the internal channel diameter will be always slightly smaller than the designed one.

The 3D-printed devices were connected to the flow system employing 1/16" outer diameter (OD) polytetrafluoroethylene (PTFE) tubing with an internal diameter of 0.5 mm. Standard connectors were fitted into the tailored inlets and outlets of each device. The fittings employed are made of polyfluoroelastomer (FPM) and Polyether Ether Ketone (PEEK), the latter a harder plastic than PP, allowing for boring into the PP plastic and thus resulting in a tight seal to the device. The device inlets were connected to the syringe pumps containing the starting material solutions, whilst the outlet was connected to the in-line ATR-IR flow cell. This set-up improves the range of pressures that can be handled by the system and enables the use of accessory equipment, such as check valves in the inlets (made of, PEEK with an O-ring in Chemraz®), which prevent backflow.

Described here is an imine syntheses monitored using an in-line ATR-IR flow cell. The flow set-up used for these syntheses consists of two syringe pumps, each connected to one of the inlets of the 3D-printed device R1. The syringe pumps were filled with the starting materials; a carbonyl compound (1a-c) in the first syringe pump and a primary amine (2a-d) into the second syringe pump. The device output was connected with a length of tubing with a volume 0.1 to the IR flow cell. Hence, the total flow reactor volume (V$_R$) was 0.5 mL.

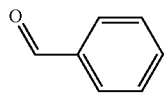

1a

-continued

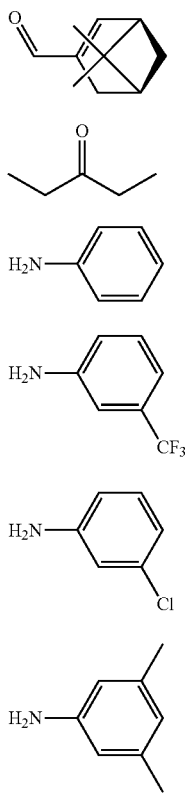

Imines are typically prepared by the condensation of a carbonyl compound and a primary amine [21]. The syntheses of the imines (3a-f) were conducted at a total flow rate of 0.125 mL min$^{-1}$, where two equimolar methanolic solutions (2 M) of 1 and 2 were flowed into R1 at the same flow rate. Each experiment was monitored by ATR-IR. The residence time for the reactions was set to 4 minutes, as this was enough to allow the reactions to go to completion. The choice of this short residence time is due to a more reliable comparison of the imines synthesized and also to avoid the formation of the Michael addiction adduct (the thermodynamic compound) in the reaction between compounds 1b and 2a.

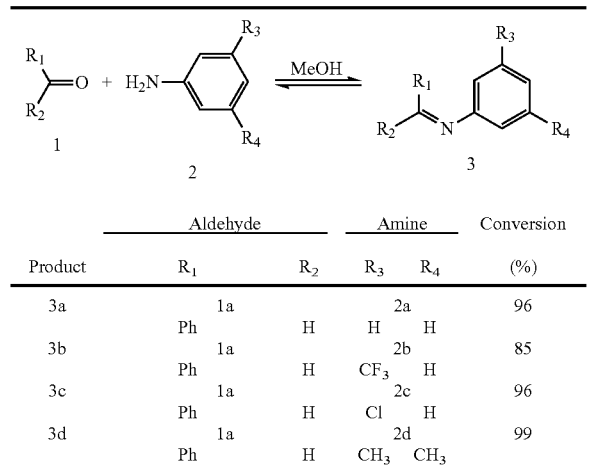

| Product | Aldehyde | | Amine | | Conversion (%) |
|---|---|---|---|---|---|
| | $R_1$ | $R_2$ | $R_3$ | $R_4$ | |
| 3a | 1a | | 2a | | 96 |
| | Ph | H | H | H | |
| 3b | 1a | | 2b | | 85 |
| | Ph | H | $CF_3$ | H | |
| 3c | 1a | | 2c | | 96 |
| | Ph | H | Cl | H | |
| 3d | 1a | | 2d | | 99 |
| | Ph | H | $CH_3$ | $CH_3$ | |

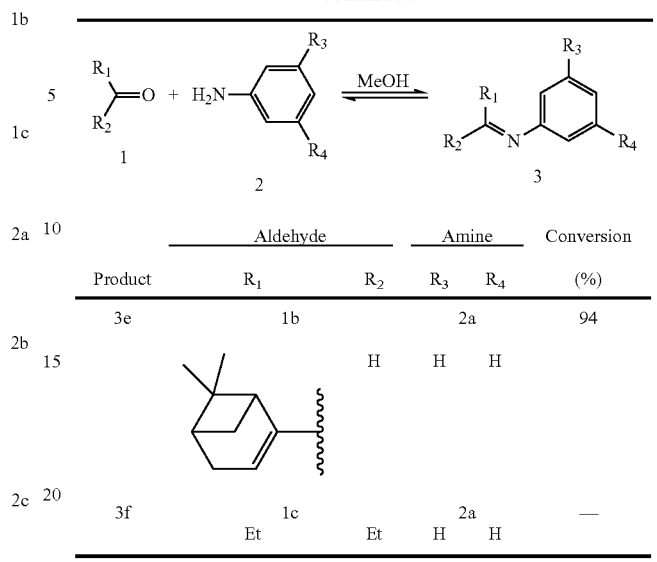

| Product | Aldehyde | | Amine | | Conversion (%) |
|---|---|---|---|---|---|
| | $R_1$ | $R_2$ | $R_3$ | $R_4$ | |
| 3e | 1b | | 2a | | 94 |
| | | | H | H | |
| 3f | 1c | | 2a | | — |
| | Et | Et | H | H | |

$^1$H NMR spectra were used to calculate the conversion rate of the amines 3a-e

Figure 16:
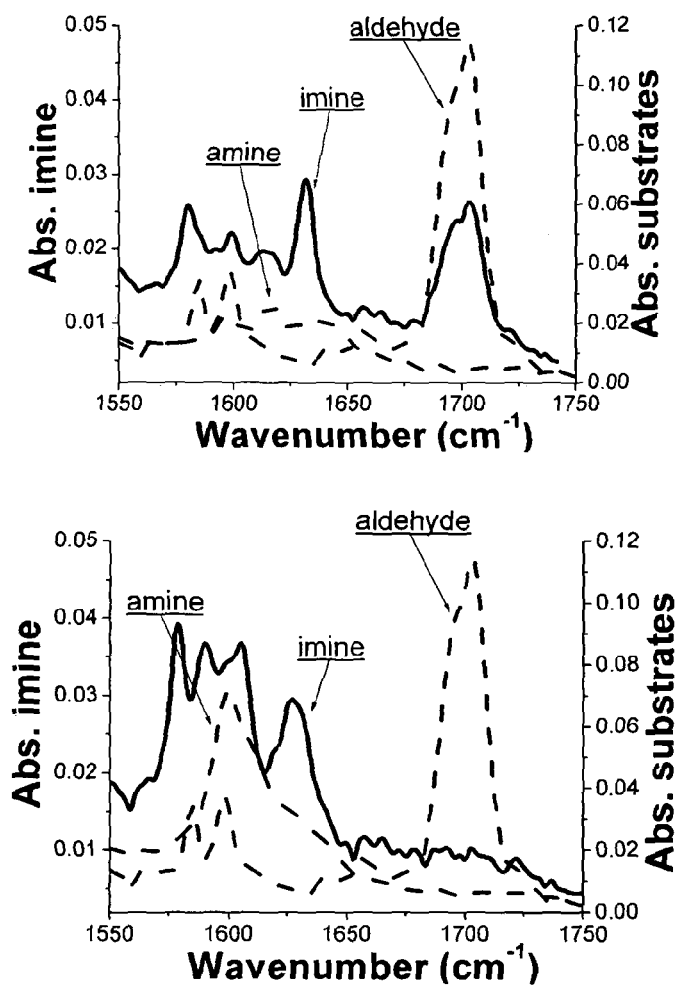
FIG. 16 shows ATR-IR spectra of the synthesis of the compounds 3d (top) and 3b (bottom) prepared in the reaction shown in FIG. 14. The spectrum on the top shows a reaction that does not go to completion due to an electron withdrawing substituent on the meta-position of the primary amine 2b.

First, we studied the reaction of benzaldehyde (1a) with aniline derivatives (2a-d), which have different substituents in the meta-positions to synthesize the imines 3a-d. The different substituents on the amine compounds have an electronic effect on the reactive centre, thus influencing the observed conversion. As expected, when the substituent in the meta position of the aniline derivatives is an electron donating group (EDG), such as the two $CH_3$ in meta position in the 3,5-dimethyl-aniline (2d), the aldehyde band disappears, while it is diminished when using an electron withdrawing group (EWG), such as $CF_3$ in the 3-trifluoromethyl-aniline (2b) is still present. This results in a different reactivity in terms of conversion; with an EDG in the meta-position of the aniline ring the conversion is higher than with an EWG. The IR spectra of the compound 3b (on top) and 3d (on bottom) are reported. In both graphs the imine spectrum (solid line) is compared with the spectrum of the starting materials (dashed line): the aldehyde peak of the benzaldehyde (1a) at 1704 cm$^{-1}$ (in black) disappears when it reacts with compound 2d (FIG. 16, on the left), while it is still present when combined with compound 2b (FIG. 16, on the right).

Imines 3a and 3b were synthesized by reacting aniline (2a) and 3-chloro-aniline (2c) with benzaldehyde (1a), respectively. As expected, complete conversion was observed for the synthesis of compound 3a, where there was no effect from the hydrogen substituent in the meta-position. Complete conversion was also observed in the synthesis of compound 3c, with this being because the chloro-substituent on aniline derivate 2c is neither a strong EWG nor EDG. However, the inductive effect ensures full conversion with $^1$H-NMR spectroscopy and MS spectrometry being used to confirm the presence of the benzyliden-phenylamines 3a-d. $^1$H-NMR spectroscopy was also used to calculate the conversion and yields of the reactions, since the only products detected in each of the 5 reactions were the respective imines 3a-d.

After studying the effect of the amine substituent on the reaction progress, benzaldehyde (1a) was substituted with a chiral and aliphatic compound, R-(−)-myrtenal (1b), and with an aliphatic ketone, pentanone (1c) and reacted with 2a. The experiments were conducted using 2 M methanolic solutions of the different substrates. This is convenient from a processing point of view, since high concentrations favours increased reaction kinetics whilst minimizing the amount of waste generated during the downstream work-up of the solutions. The residence time was calculated from the mixing point inside the 3D-printed reactors until the analytical device, thus taking into account the subsequent pieces of tubing employed. The results of these reactions are summarized in Table 2. The reaction with the α,β-unsaturated aldehyde (compound 1b) continued to give the imine 3e (94%), whilst with the ketone compound 1c) no product was observed, due to its lower reactivity.

To calculate the conversion of the benzaldehyde (1a) into the imines 3a-d when combined with the amines 2a-d, a calibration of the IR spectra of benzaldehyde at known concentrations was employed. The different concentrations of the substrates analysed do not significantly affect the area of the solvent band at 1022 cm$^{-1}$ ($A_{1022}$). Hence, it is possible to use the solvent peak to normalise the different spectra and obtain comparable results. Five methanolic solutions of benzaldehyde (0.125 M, 0.25 M, 0.5 M, 1 M, 2 M) were measured, and the relative band area at 1704 cm$^{-1}$ ($A_{1704}$) were used to build the calibration curve. The relative areas were calculated using the formula $A_{1704}/(A_{1022}+A_{1704})$ in order to minimize the slight change of $A_{1022}$ with the concentration of the benzaldehyde.

Different flow rates were assayed to elucidate the effect of reaction time. To synthesize the imine 3a, equimolar amounts of benzaldehyde (1a) and aniline (2a) were mixed in ratio (1:1) (v:v) at different flow rates in the range 0.25-1.5 mL min$^{-1}$. The observed conversion range found was between 94% and 97%. Under the studied conditions, very high conversions were obtained with residence times as low as 20 seconds.

Reductive Amination

Figure 17:
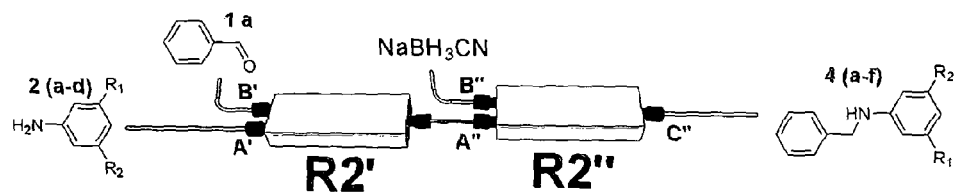
FIG. 17 is a representation of a multicomponent reaction vessel according to an embodiment of the present invention, utilising a reaction vessel as illustrated in FIG. 15 (R2). The first component is used to synthesise an imine compound under previously optimised conditions. The imine product is then directly introduced into the second component of the reaction vessel and is mixed with a reducing agent to produce a secondary amine product (4a-f).

After optimising the conditions to produce imines with nearly quantitative conversion under flow conditions, efforts were focussed on conducting two consecutive reactions. To this end, two R2 devices were connected in series (FIG. 17), to monitor the formation of the final product using the in-line IR flow cell. The imine synthesis was run in the first of the two devices (R2'), and once formed the imine was subsequently reduced in the second device (R2"). R2' was connected to the syringe pumps containing the starting materials (compounds 1a and 2a-d) for the imine synthesis as previously described, and in particular the imines 3a-d were re-synthesized with a larger residence time to ensure a complete conversion of the substrates, before they were directly introduced to R2".

The reduction of imines is an interesting strategy to synthesise functionalised secondary amines. The synthesis used a 2M solution of benzaldehyde (1a) in MeOH, which was pumped through inlet B into device R2' at 0.0125 mL min$^{-1}$ and mixed with a 2M solution of aniline (2a-d) derivatives in MeOH introduced through inlet A at the same flow rate, keeping the aldehyde:amine ratio (1:1) (v:v) as described for the imine synthesis. This low flow rate (compared with the imine synthesis discussed above) was selected to have a sufficient residence time ($t_R$=14 minutes) for a full conversion of the aldehydes into imines. Device R2' was connected to the inlet A of a second device (R2") where the freshly formed imine was mixed with the reducing agent, cyanoborohydride (NaBH$_3$CN) in MeOH (1M), introduced through inlet B, where the two equimolar solutions were pumped through R2" at the same flow rate. The molar and volumetric ratios hydride:imine were kept constant (1:1) to produce the corresponding amines with a residence time of 7 min. This reducing agent was selected because it is mild but effective, and it prevents the undesired formation of bubbles or problems related to over-reduction, which could be expected in this range of concentrations when using conventional reducing agents, such as NaBH$_4$. Using this methodology, imines 3a-d were reduced to produce the corresponding secondary amines 4a-d.

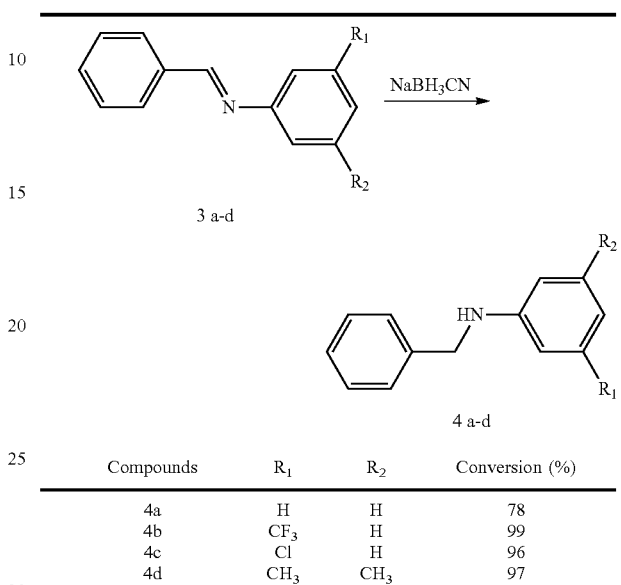

| Compounds | R$_1$ | R$_2$ | Conversion (%) |
|---|---|---|---|
| 4a | H | H | 78 |
| 4b | CF$_3$ | H | 99 |
| 4c | Cl | H | 96 |
| 4d | CH$_3$ | CH$_3$ | 97 |

$^1$H NMR spectroscopy and MS spectrometry confirmed the presence of the amine.
$^1$H NMR spectra were used to calculate the conversion rate of the amines 4a-d.

The reaction was monitored by the absence of the imine and aldehyde bands in the in-line ATR-IR flow cell, focusing the attention to the region of the IR spectrum between 1700 cm$^{-1}$ and 1500 cm$^{-1}$, where the disappearance of the imine band (around 1630 cm$^{-1}$) may be observed. A complete conversion of the aldehyde into the imine can be observed (due to the absence of the aldehyde peak at 1704 cm$^{-1}$). In the case of compound 4b, the imine peak at 1632 cm$^{-1}$ was seen to completely disappear.

In addition to the IR analysis, the compounds 4a-d were collected and analysed by MS spectrometry, HPLC and $^1$H-NMR spectroscopy. In all the studied cases, the absence of imine bands in $^1$H-NMR spectroscopy and the presence of the corresponding secondary amine bond confirmed quantitative conversion of the substrates.

EXPERIMENTAL

All solutions were pumped by means of C-3000 syringe pumps from Tricontinent equipped with 1 mL syringes. An in-house developed Labview application was employed to program the pumps to deliver the desired flow-rates and to control the IR spectroscopy.

IR spectra were collected employing a Nicolet IS-5 from Thermo Scientific and a ZnSe Golden Gate ATR from Specac equipped with a flow cell. The resolution was set at 4 cm$^{-1}$ and 16-80 scans were recorded.

Mass spectra were recorded using a JEOL JMS 700 (EI/CI). The observed ca. m/z values are listed.

NMR data were recorded on a Bruker Advance 400 MHz, in deuterated MeOH from Goss Scientific, at T=300 K. All chemical shifts are given in ppm. The peaks are denoted s=singlet, d=doublet, t=triplet, dt=doublet of triplet, and m=multiplet.

HPLC was performed using a 150×2.00 mm, 3 μm Phenomenex column on a Agilent 1100 Series equipped with UV detector with a source light of 254 wavelength at 25° C. A mixture of Acetonitrile (HPLC gradient grade) and a buffer, made of sodium acetate, tuned to pH-value 3.72, was used in ratio 95:5 as eluent. 10 μL of each samples (1 M) was diluted in 1 mL of Acetonitrile; 1 μL of this solution was injected at a flow rate of 0.5 mL min$^{-1}$.

Imine Formation

A 2 M methanolic solution of carbonyl compound (1a-c) was mixed with a 2 M methanolic solution of primary amines (2a-d) at the same flow rate (0.25 mL using the 3D-printed device R1, with a total reactor volume of 0.5 mL (0.4 mL+0.1 mL), a residence time of about 4 minutes and a total flow rate being 0.1 mL min$^{-1}$. The outlet of the reactor was connected to the flow-cell of a Golden Gate ATR-IR. The products were analysed by flow ATR-IR and $^1$H NMR spectroscopy, EI-MS spectrometry and HPLC.

(3a): this imine was synthesized by reacting compounds 1a and 2a. $^1$H NMR: (400 MHz. CDCl$_3$) (δ, ppm) 8.56 (s, 1H), 8.00-7.97 (m, 2H), 7.58-7.59 (m, 3H), 7.54-7.44 (m, 3H), 7.36-7.31 (m, 2H); MS (EI$^+$): calcd. for C$_{13}$H$_{12}$N (M$^+$) m/z 181.08. found 181.15; HPLC: t$_R$=1.22 min; IR: 1703 cm$^{-1}$ peak from C=O moiety disappeared, 1627 cm$^{-1}$ peak from C=N—C moiety appeared.

(3b): this imine was synthesized by reacting compounds 1a and 2b. $^1$H NMR: (400 MHz, CD) (δ, ppm) 8.48 (s, 1H), 7.96-7.93 (m, 2H), 7.54-7.52 (m, 5H), 7.47 (s, 1H), 7.40 (m, 1H); MS (EI$^+$): calcol. for C$_{14}$H$_{10}$F$_3$N (M$^+$) m/z 249.08. found 249.13. HPLC: t$_R$=1.25 min; IR: 1703 cm$^{-1}$ peak from C=O moiety disappeared, 1632 cm$^{-1}$ peak from C=N—C moiety appeared.

(3c): this imine was synthesized by reacting compounds 1a and 2c. $^1$H NMR: (400 MHz, CD (δ, ppm) 8.32 (s, 1H), 7.95-7.95 (m, 2H), 7.60-7.55 On, 3H), 7.44 (m, 1H), 7.31-7.28 (m, 2H), 7.20-7.17 (m, 1H); MS (CI$^+$): calcd. for C$_{13}$H$_{10}$ClN (M$^+$) m/z 215.05. found 215.12. HPLC: t$_R$=1.30 min; IR: 1703 cm$^{-1}$ peak from C=O moiety disappeared, 1631 cm$^{-1}$ peak from C=N—C moiety appeared.

(3d): this imine was synthesized by reacting the compounds 1a and 2d. $^1$H-NMR: (400 MHz, CDCl$_3$) (δ, ppm) 8.47 (s, 1H), 7.93-7.90 (m, 2H), 7.50-7.48 (m, 3H), 6.91 (s, 1H), 6.87 (s, 2H), 2.38 (s, 6H); MS (EI$^+$): calcd. for C$_{15}$H$_{16}$N (M$^+$) 209.12. found 209.19. HPLC: t$_R$=1.44 min; IR: 1703 cm$^{-1}$ peak from C=N moiety disappeared, 1627 cm$^{-1}$ peak from CH$_2$NH-Ph moiety appeared.

(3e): this imine was synthesized by reacting the compounds 1 b and 2e. $^1$H NMR: (400 MHz, CD) (δ, ppm) 8.03 (s, 1H), 7.38-7.34 (m, 2H), 7.21-7.16 (m, 1H), 7.14 (m, 2H), 6.28-6.27 (m, 1H), 3.20 (td, 1H, Jd=1.3 Hz, Jt=5.6 Hz), 2.58-2.56 (m, 4H), 2.25-2.20 (m, 1H), 1.41 (s, 3H), 1.06 (d, 1H, J=9.3 Hz), 0.87 (s, 3H); MS (EI$^+$): calcd. for C$_{16}$H$_{19}$N (M$^+$) m/z 225.15. found 225.2. IR: 1673 cm$^{-1}$ peak from C=O moiety disappeared, 1586 cm$^{-1}$ peak from C=N—C moiety appeared.

Reductive Amination

Two 2M methanolic solutions of primary amines (2a-d) and benzaldehyde (1a) were pumped in the device R2', at the same flow rate of 0.0125 mL min$^{-1}$, and with the aldehyde: amine ratio (1:1) (1 mL:1 mL). In this second device R2" each of the resulting compounds 3a-d was mixed using a flow rate of 0.025 mL min$^{-1}$ with a 1 M methanolic solution of cyanoborohydride, at the same flow rate, and using a molar and volumetric ratios hydride:imine of (1:1) (1 mL:1 mL): with the total flow rate of 0.05 mL min$^{-1}$ and the residence time in R2" of 7 minutes, a secondary amine (4a-d) was synthesised. The samples were characterised by flow ATR-IR and $^1$H-NMR spectroscopy and MS spectrometry.

(4a): this amine was obtained reducing the compounds 3a. $^1$H NMR: (400 MHz, CD) (δ, ppm) 7.46-7.40 (m, 7H), 6.79-6.69 (m, 3H) 4.38 (s, 2H), 4.36 (s, 1H), MS (EI$^+$): calcd. for C$_{13}$H$_{13}$N (M+) m/z 183.1. found 183.2. HPLC: t$_R$=1.18 min; IR: 1627 cm$^{-1}$ peak from C=N moiety disappeared, 1603 cm$^{-1}$ peak from CH$_2$NH-Ph moiety appeared.

(4b): this amine was obtained reducing the compounds 3b. $^1$H NMR: (400 MHz, CD) (δ, ppm) 7.45-7.40 (m, 5H), 6.99-6.97 (m, 2H), 6.92 (s, 1H), 6.85-6.82 (m, 2H) 4.42 (s, 2H), 4.25 (s, 1H); MS (EI$^+$): calcd. for C$_{14}$H$_{12}$F$_3$N (M$^+$) m/z 251.09. found 251.1.

HPLC: t$_R$=1.15 min; IR: 1632 cm$^{-1}$ peak from C=N moiety disappeared, 1617 cm$^{-1}$ peak from CH$_2$NH-Ph moiety appeared.

(4c): this amine was obtained reducing the compounds 3c. $^1$H NMR: (400 MHz, CD) (δ, ppm) 7.42-7.38 (m, 5H), 7.11 (t, J=7.8 Hz, 3H), 6.73 (s, 1H), 6.72-6.70 (dd, J=7.8 Hz, J=2.3 Hz, 1H), 8.59-0.53 (dd. J=7.8 Hz, J=2.3 Hz, 1H) 4.36 (s, 2H), 3.82 (s, 1H); MS (CI$^+$); calcd. for C$_{13}$H$_{12}$ClN (M$^+$) m/z 218.07. found 218.1. HPLC: t$_R$=1.11 min; IR: 1631 cm$^{-1}$ peak from C=N moiety disappeared, 1600 cm$^{-1}$ peak from CH$_2$NH-Ph moiety appeared.

(4d): this amine was obtained reducing the compounds 3d. $^1$H NMR: (400 MHz, CD) (δ, ppm) 7.45-7.36 (m, 5H), 6.43 (s, 1H), 6.34 (s, 2H), 4.34 (s, 2H), 4.03 (s, 1H) 2.27 (s, 6H); MS (EI$^+$): calcd. for C$_{15}$H$_{18}$N (M$^+$) 211.14. found 211.2. HPLC: t$_R$=1.23 min; IR: 1627 cm$^{-1}$ peak from C=N moiety disappeared, 1603 cm$^{-1}$ peak from CH$_2$NH-Ph moiety appeared.

Plug Purification

Figure 19:
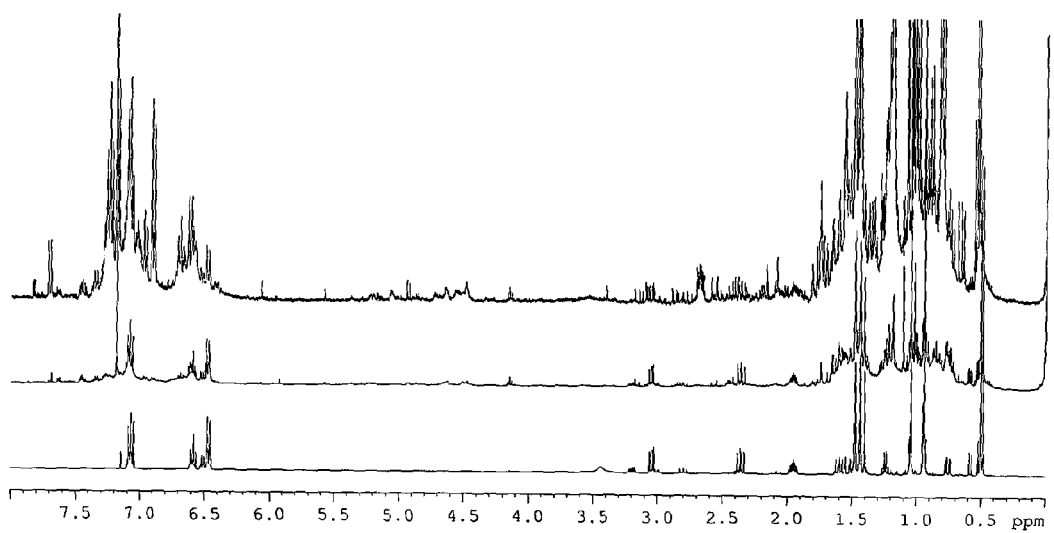
FIG. 19 includes three $^1$H NMR spectra for (top) the unpurified product compound (3a,b) produced from the reaction vessel of FIG. 13 (right); (middle) the product compound (3a,b) produced from the reaction vessel of FIG. 13 after passage through a silica plug of material; and (bottom) the product compound (3a,b) after a full column chromatography.

The product compound 3a,b was obtained as described above from the reaction vessels of FIG. 13 (left) and (right). NMR analysis of the crude product produced using the reaction vessel of FIG. 13 (right) is shown in FIG. 19 (top). The reaction using the vessel of FIG. 13 (right) was repeated with the reaction vessel of FIG. 18, which incorporates a silica plug as part of a fourth reaction space.

Solvothermal Synthesis

The inventor prepared a bomb (a sealed reaction vessel) for use in the preparation of crystalline materials. The bomb was essentially a polypropylene reaction vessel having an internal spherical reaction space (chamber) and the printed wall thickness was at least 3 mm.

Terephthalic acid was crystallised in the bomb from 1:1 Zn(NO$_3$)$_2$ and terephthalic acid in DMF with approx 1% vol HNO$_3$ for 3 days at 80° C.

Terephthalic acid was crystallised in the bomb from AlCl$_3$ and terephthalic acid in water at 150° C. for 5 hours.

The polypropylene-printed reaction vessel (bomb) was found to maintain integrity at temperatures up to 160° C. and at pressures up to 6 bar.

REFERENCES

All documents mentioned in this specification are incorporated herein by reference in their entirety.

Ahn, B. Y. et al. *Science*. 323, 1590-1593 (2009)
Browne, K. P., Walker, D. A., Bishop, K. J. M. & Grzybowski, B. A. *Angew. Chem. Int Ed.* 49, 6756-6759 (2010)
Cohen et al. *Tissue Engineering* 2006, 12, 1325
Cohen, D. L., Malone, E., Lipson, H. & Bonassar, L. J. *Tissue Eng*. 12, 1325-1335 (2006).
Cook, T. R. et al. *Chem. Rev.* 110, 6474-6502 (2010)

Cooper, G. J. T. et al. *Angew. Chem. Int. Ed.* DOI: 10.1002/anie.201105068 (2011)

fab@home, the open-source personal fabricator project, http://www.fabathome.org, accessed Sep. 22, 2011

Farrugla, L. J. WinGX suite for small-molecule single-crystal crystallography. *J. Appl. Cryst.* 32, 837-838 (1999)

Geissler, M. & Xia, Y. *Adv. Mater.* 16, 1249-1269 (2004)

Gershenfeld, N., Samouhos, S. & Nordman, B. *Science*. 327, 1086-1088 (2010)

Gratson, G. M., Xu, M. & Lewis, J. A. *Nature*. 428, 386 (2004)

Hanson Shepherd, J. N. et al. *Adv. Funct. Mater.* 21, 47-54 (2011)

Ilievski, F., Mazzeo, A. D., Shepherd, R. F., Chen, X. & Whitesides, G. M. *Angew. Chem. Int. Ed.* 50, 1890-1895 (2011)

Kortz, U. Savelieff, M. G., Bassil, B. S. & Dickman, M. H. *Angew. Chem. Int. Ed.* 40, 3384-3386 (2001)

Lee, K.-W., Wang, S., Dadsetan, M., Yaszemski, M. J. & Lu, L. *Biomacromolecules*. 11, 682-689 (2010)

Lewis, J. A. *Adv. Funct. Mater.* 16, 2193-2204 (2006)

Maldonado, A, G. & Rothenberg, G. *Chem. Soc. Rev.* 39, 1891-1902 (2010)

Malone et al. available via http://creativemachines.cornell.edu/papers/SFF04_Malone.pdf Malone et al. *Rapid Prototyping Journal* 2004, 10, 58

Malone, E. & Lipson, H. Fab@Home: The personal desktop fabricator kit. *Rapid Prototyping J.* 13, 245-255 (2007)

Marks, P., Campbell, M., Aron, J. & Lipson, H. *New Sci.* 2823, 17-20 (2011)

Martinez, A. W., Phillips, S. T. & Whitesides, G. M. *Proc. Natl. Acad. Sci. U.S.A.* 105, 19606-19611 (2008)

Nakamura, M., Iwanaga, S., Henmi, C., Arai, K. & Nishiyama, Y. *Biofabrication*. 2, 014110 (2010)

Parenty, A. D. C., Smith, L. V., Pickering, A. L., Long, D.-L. & Cronin, L. *J. Org. Chem.* 69, 5934-5946 (2004)

Pearce, J. M. et al. *Journal of Sustainable Development.* 3, 17-29 (2010)

Rhino3D, NURBS modeling for Windows, http://www.rhino3d.com, accessed 22 Sep. 2011

Richmond, C. J., Eadie, R. M., Parenty, A. D. C. & Cronin, L. *J. Org. Chem.* 74, 8196-8202 (2009)

Sheldrick, G. M. *Acta Crystallogr., Sect. A* A46, 467-473 (1998)

Sheldrick, G. M. *Acta Crystallogr., Sect. A* A64, 112-122 (2008)

Stampfl, J. & Liska, R. *Macromol. Chem. Phys.* 206, 1253-1256/2005)

Stoddart, J. F. & Tsang, H.-R. *Proc. Natl. Acad. Sci. U.S.A.* 99, 4797-4800 (2002)

Tanaka, N., Unoura, K. & Itabashi, E. *Inorg. Chem.* 21, 1662-1666 (1982)

Therriault, D., White, S. R. & Lewis, J. A. *Nat. Mater.* 2, 265-271 (2003)

Vilbrandt, T., Pasko, A. & Vilbrandt, C. *Technoetic Arts.* 7, 165-174 (2009)

Yager, P. et al. *Nature*. 442, 412-418 (2006)

The invention claimed is:

1. A method for preparing a product compound, the method comprising the steps of:
   (i) providing a reaction vessel that is obtained by a 3-D printing method, wherein the reaction vessel has a reaction space;
   (ii) providing one or more reagents, optionally together with a catalyst and optionally with a solvent, for use in a synthesis of the product compound; and
   (iii) permitting the one or more reagents to react in the reaction space, optionally in the presence of the catalyst and optionally in the presence of the solvent, in the reaction vessel, thereby to form the product compound, wherein one of the one or more reagents, or the catalyst or the solvent where present, is delivered to the reaction vessel by a 3-D printer.

2. A method according to claim 1, wherein one of the one or more reagents is delivered to the reaction vessel by the 3-D printer.

3. A method according to claim 1, wherein a wall of the reaction vessel comprises a reagent or catalyst for use in the preparation of the product compound, wherein at least a portion of the reagent or catalyst is available for reaction at the reaction space.

4. A method according to claim 1, wherein the reaction vessel is provided with a fluid channel in communication with the reaction space, wherein the fluid channel is suitable for removal of reaction material to or from the reaction space.

5. A method according to claim 4, wherein the reaction vessel is provided with a reservoir which is in fluid communication with the reaction space via the channel.

6. A method according to claim 1, wherein the reaction vessel is provided with a plurality of reaction spaces, and the reaction spaces are in fluid communication.

7. A method according to claim 6, wherein a wall of each of two or more reaction spaces comprises a reagent or catalyst for use in the preparation of a product compound, wherein at least a portion of the reagent or catalyst is available for reaction at each of the two or more reaction spaces.

8. A method according to claim 1, wherein a reaction space is a chamber.

9. A method according to claim 1, wherein a reaction space is a fluid channel.

10. A method according to claim 1, wherein a membrane is provided in a reaction space.

11. A method according to claim 1, wherein the reaction vessel comprises one or more electrodes which are available at the reaction space.

12. A method according to claim 1, wherein the reaction vessel is a multicomponent reaction vessel.

13. A method according to claim 12, wherein each component has a reaction space, and the reaction spaces are in fluid communication.

14. A method according to claim 13, wherein the components are separate.

15. A method according to claim 6, wherein the one or more reagents are permitted to react in a first reaction space, optionally in the presence of the catalyst and the solvent, in the reaction vessel, thereby to form a first product compound;
   subsequently transferring the product formed in the first reaction space to a second reaction space;
   providing one or more further reagents, optionally together with a further catalyst and/or further solvent, for use in the synthesis of a second product compound;
   permitting the one or more further reagents to react with the first product in the second reaction space, optionally in the presence of the further catalyst and/or the further solvent, thereby to form the second product compound.

16. The method of claim 1, wherein the reaction vessel is a second reaction vessel, and a reaction outcome is determined for the reaction in the reaction space of the second reaction vessel, and the method further comprises the steps of:

(a) performing the reaction in the reaction space of a first reaction vessel, and determining a reaction outcome;
(b) comparing the reaction outcomes from the first reaction vessel and the second reaction vessel.

17. The method according to claim 16, wherein the first reaction vessel is obtained by a 3-D printing method and differs from the second reaction vessel.

18. The method according to claim 16, wherein the reaction outcome is a parameter selected from the group consisting of: the yield of a product, the yield of a by-product, the identity of the product, identity of a by-product, product molecular weight, product polydispersity, product size, product shape, surface enhanced resonance effect, conductivity, magnetic state, quantum spin state, nuclear spin state, melting point, boiling point, circular dichromism, binding affinity, the maximum, minimum or average temperature of the reaction, reaction time, redox potential, wavelengths of absorbance or emission, and absorbance maximum.

19. The method according to claim 16, wherein the second reaction vessel differs from the first reaction vessel in one or more of the parameters selected from the group consisting of:
   reaction space volume;
   reaction space shape;
   reaction space wall surface area;
   reaction space wall surface composition;
   reaction space wall surface roughness;
   vessel shape;
   vessel size; and
   vessel material.

* * * * *